US010245369B2

(12) United States Patent
Kelly et al.

(10) Patent No.: US 10,245,369 B2
(45) Date of Patent: *Apr. 2, 2019

(54) SYSTEMS AND METHODS FOR PRIMING HEMODIALYSIS USING DIALYSIS FLUID

(71) Applicants: Baxter International Inc., Deerfield, IL (US); Baxter Healthcare S.A., Glattpark (Opfikon) (CH)

(72) Inventors: Thomas Kelly, Highland Park, IL (US); Robert W. Childers, New Port Richey, FL (US); Don Busby, Thousand Oaks, CA (US); Rodolfo Roger, Clearwater, FL (US); Waleed Mutasem El Sayyid, Dover, NJ (US); Shahid Din, Palm Harbor, FL (US)

(73) Assignees: Baxter International Inc., Deerfield, IL (US); Baxter Healthcare SA, Glattpark (Opfikon) (CH)

( * ) Notice: Subject to any disclaimer, the term of this patent is extended or adjusted under 35 U.S.C. 154(b) by 427 days.

This patent is subject to a terminal disclaimer.

(21) Appl. No.: 15/163,128

(22) Filed: May 24, 2016

(65) Prior Publication Data

US 2016/0263306 A1 Sep. 15, 2016

Related U.S. Application Data

(63) Continuation of application No. 13/749,309, filed on Jan. 24, 2013, now Pat. No. 9,364,602, which is a
(Continued)

(51) Int. Cl.
*A61M 1/36* (2006.01)
*A61M 1/16* (2006.01)
(Continued)

(52) U.S. Cl.
CPC ........ *A61M 1/3621* (2013.01); *A61M 1/1037* (2013.01); *A61M 1/16* (2013.01);
(Continued)

(58) Field of Classification Search
CPC .............. A61M 1/3621; A61M 1/1601; A61M 1/1607; A61M 1/1613; A61M 1/1621;
(Continued)

(56) References Cited

U.S. PATENT DOCUMENTS 3,669,880 A 6/1972 Marantz et al.
3,774,762 A 11/1973 Lichtenstein
(Continued)

FOREIGN PATENT DOCUMENTS

CA 1121738 4/1982
DE 2002033 8/1970
(Continued)

OTHER PUBLICATIONS

Japanese Office Action dated Sep. 30, 2015 for corresponding Japanese Appln. No. 2014-223121 (8 pages).
(Continued)

*Primary Examiner* — Philip R Wiest
(74) *Attorney, Agent, or Firm* — K&L Gates LLP

(57) ABSTRACT

A method for priming a hemodialysis treatment includes: providing a disposable cassette including at least a portion of a dialysate circuit and at least a portion of a blood circuit; placing a dialyzer in fluid communication with the dialysate circuit via a to-dialyzer dialysate line and a from-dialyzer dialysate line; placing the dialyzer in fluid communication with the blood circuit via an arterial blood line and a venous blood line; placing a source of dialysis fluid in fluid communication with the dialyzer; priming the dialysate circuit with dialysis fluid from the source while both the to-dialyzer dialysate line and the from-dialyzer dialysate line are con-
(Continued)

nected at their dialyzer ends to the dialyzer; and priming the blood circuit with dialysis fluid from the source by actuating at least one valve provided by the disposable cassette.

20 Claims, 46 Drawing Sheets

Related U.S. Application Data continuation of application No. 13/222,622, filed on Aug. 31, 2011, now Pat. No. 9,072,830, which is a continuation of application No. 10/982,170, filed on Nov. 4, 2004, now Pat. No. 8,029,454.

(60) Provisional application No. 60/517,730, filed on Nov. 5, 2003.

(51) Int. Cl.
    *A61M 1/34*           (2006.01)
    *A61M 1/28*           (2006.01)
    *A61M 1/10*           (2006.01)
    *A61M 1/26*           (2006.01)

(52) U.S. Cl.
CPC .......... *A61M 1/1601* (2014.02); *A61M 1/166* (2014.02); *A61M 1/1607* (2014.02); *A61M 1/167* (2014.02); *A61M 1/1613* (2014.02); *A61M 1/1621* (2014.02); *A61M 1/1629* (2014.02); *A61M 1/1633* (2014.02); *A61M 1/1635* (2014.02); *A61M 1/1656* (2013.01); *A61M 1/1668* (2014.02); *A61M 1/1672* (2014.02); *A61M 1/1696* (2013.01); *A61M 1/267* (2014.02); *A61M 1/288* (2014.02); *A61M 1/341* (2014.02); *A61M 1/342* (2013.01); *A61M 1/3417* (2014.02); *A61M 1/3427* (2014.02); *A61M 1/3431* (2014.02); *A61M 1/3434* (2014.02); *A61M 1/3437* (2014.02); *A61M 1/3444* (2014.02); *A61M 1/3451* (2014.02); *A61M 1/3458* (2014.02); *A61M 1/3465* (2014.02); *A61M 1/3468* (2014.02); *A61M 1/3472* (2013.01); *A61M 1/3486* (2014.02); *A61M 1/365* (2014.02); *A61M 1/3624* (2013.01); *A61M 1/3626* (2013.01); *A61M 1/3627* (2013.01); *A61M 1/3643* (2013.01); *A61M 1/3644* (2014.02); *A61M 1/3646* (2014.02); *A61M 1/3647* (2014.02); *A61M 1/3649* (2014.02); *A61M 1/3652* (2014.02); *A61M 1/3656* (2014.02); *A61M 1/101* (2013.01); *A61M 1/1006* (2014.02); *A61M 1/1012* (2014.02); *A61M 1/1039* (2014.02); *A61M 1/1062* (2014.02); *A61M 1/1081* (2013.01); *A61M 1/1086* (2013.01); *A61M 2202/0413* (2013.01); *A61M 2205/12* (2013.01); *A61M 2205/13* (2013.01); *A61M 2205/15* (2013.01); *A61M 2205/18* (2013.01); *A61M 2205/276* (2013.01); *A61M 2205/3317* (2013.01); *A61M 2205/3324* (2013.01); *A61M 2205/3327* (2013.01); *A61M 2205/3331* (2013.01); *A61M 2205/3334* (2013.01); *A61M 2205/3337* (2013.01); *A61M 2205/3344* (2013.01); *A61M 2205/3368* (2013.01); *A61M 2205/3379* (2013.01); *A61M 2205/3393* (2013.01); *A61M 2205/3553* (2013.01); *A61M 2205/3561* (2013.01); *A61M 2205/3584* (2013.01); *A61M 2205/502* (2013.01); *A61M 2205/505* (2013.01); *A61M 2205/52* (2013.01); *A61M 2205/75* (2013.01)

(58) Field of Classification Search
CPC .............. A61M 1/1629; A61M 1/1633; A61M 1/1635; A61M 1/166; A61M 1/1668; A61M 1/1672; A61M 1/267; A61M 1/288; A61M 1/341; A61M 1/3417; A61M 1/3427; A61M 1/3431; A61M 1/3434; A61M 1/3437; A61M 1/3444; A61M 1/3451; A61M 1/3458; A61M 1/3465; A61M 1/3468; A61M 1/3486; A61M 1/365; A61M 1/3652; A61M 1/3656; A61M 1/1037; A61M 1/16; A61M 1/1656; A61M 1/1696; A61M 1/342

See application file for complete search history.

(56) References Cited

U.S. PATENT DOCUMENTS

| | | |
|---|---|---|
| 3,946,731 A | 3/1976 | Lichtenstein |
| 4,079,007 A | 3/1978 | Hutchisson |
| 4,096,059 A | 6/1978 | Pinkerton |
| 4,161,264 A | 7/1979 | Malmgren et al. |
| 4,190,536 A | 2/1980 | Grimsrud |
| 4,209,391 A | 6/1980 | Lipps et al. |
| 4,240,408 A | 12/1980 | Schael |
| 4,244,816 A | 1/1981 | Vogler et al. |
| 4,267,040 A | 5/1981 | Schal |
| 4,366,061 A | 12/1982 | Papanek et al. |
| 4,386,634 A | 6/1983 | Stasz et al. |
| 4,464,172 A | 8/1984 | Lichtenstein |
| 4,468,329 A | 8/1984 | Shaldon et al. |
| 4,477,342 A | 10/1984 | Allan et al. |
| 4,530,759 A | 7/1985 | Schal |
| 4,614,590 A | 9/1986 | Rath et al. |
| 4,618,343 A | 10/1986 | Polaschegg |
| 4,650,458 A | 3/1987 | Dahlberg et al. |
| 4,661,246 A | 4/1987 | Ash |
| 4,702,829 A | 10/1987 | Polaschegg et al. |
| 4,708,802 A | 11/1987 | Rath et al. |
| 4,711,715 A | 12/1987 | Polaschegg |
| 4,715,959 A | 12/1987 | Allan et al. |
| 4,747,950 A | 5/1988 | Guinn |
| 4,756,706 A | 7/1988 | Kerns et al. |
| 4,767,399 A | 8/1988 | Bollish |
| 4,769,134 A | 9/1988 | Allan et al. |
| 4,770,769 A | 9/1988 | Schael |
| 4,804,950 A | 2/1989 | Moon et al. |
| 4,828,543 A | 5/1989 | Weiss et al. |
| 4,834,888 A | 5/1989 | Polaschegg |
| 4,838,865 A | 6/1989 | Flank et al. |
| 4,857,199 A | 8/1989 | Cortial |
| 4,873,623 A | 10/1989 | Lane et al. |
| 4,898,578 A | 2/1990 | Rubalcaba et al. |
| 4,914,624 A | 4/1990 | Dunthorn |
| 4,916,441 A | 4/1990 | Gombrich |
| 4,935,125 A | 6/1990 | Era et al. |
| 4,971,700 A | 11/1990 | Tsuii et al. |
| 4,997,570 A | 3/1991 | Polaschegg |
| 5,056,059 A | 10/1991 | Tivig et al. |
| 5,114,580 A | 5/1992 | Ahmad et al. |
| 5,152,671 A | 10/1992 | Harant |
| 5,173,125 A | 12/1992 | Felding |
| 5,211,849 A | 5/1993 | Kitaevich et al. |
| 5,282,783 A | 2/1994 | Lindsay |
| 5,376,263 A | 12/1994 | Fischel |
| 5,421,823 A | 6/1995 | Kamen et al. |
| 5,470,483 A | 12/1995 | Bene et al. |
| 5,522,998 A | 6/1996 | Polaschegg |
| 5,536,412 A | 7/1996 | Ash |
| 5,542,919 A | 8/1996 | Simon et al. |
| 5,578,223 A | 11/1996 | Bene et al. |
| 5,614,677 A | 3/1997 | Wansiedler et al. |
| 5,660,722 A | 8/1997 | Nederlof |
| 5,698,090 A | 12/1997 | Bene et al. |
| 5,702,597 A | 12/1997 | Chevallet et al. |

(56) References Cited

U.S. PATENT DOCUMENTS

| | | |
|---|---|---|
| 5,725,775 A | 3/1998 | Bene et al. |
| 5,730,712 A | 3/1998 | Falkvall et al. |
| 5,776,345 A | 7/1998 | Truitt et al. |
| 5,783,085 A | 7/1998 | Fischel |
| 5,788,846 A | 8/1998 | Sternby |
| 5,836,908 A | 11/1998 | Beden et al. |
| 5,846,419 A | 12/1998 | Nederlof |
| 5,863,421 A | 1/1999 | Peter, Jr. et al. |
| 5,910,252 A | 6/1999 | Truitt et al. |
| 5,919,369 A | 7/1999 | Ash |
| 5,925,011 A | 7/1999 | Faict et al. |
| 5,938,634 A | 8/1999 | Packard |
| 6,077,443 A | 6/2000 | Goldau |
| 6,110,384 A | 8/2000 | Goux et al. |
| 6,126,831 A | 10/2000 | Goldau et al. |
| 6,139,748 A | 10/2000 | Ericson et al. |
| 6,234,991 B1 | 5/2001 | Gorsuch |
| 6,254,567 B1 | 7/2001 | Treu et al. |
| 6,260,715 B1 | 7/2001 | Simard et al. |
| 6,280,632 B1 | 8/2001 | Polaschegg |
| 6,287,516 B1 | 9/2001 | Matson et al. |
| 6,447,491 B1 | 9/2002 | Lord |
| 6,491,656 B1 | 12/2002 | Morris |
| 6,495,366 B1 | 12/2002 | Briggs |
| 6,572,576 B2 | 6/2003 | Brugger et al. |
| 6,572,641 B2 | 6/2003 | Brugger et al. |
| 6,582,385 B2 | 6/2003 | Burbank et al. |
| 6,589,482 B1 | 7/2003 | Burbank et al. |
| 6,607,669 B2 | 8/2003 | Schick |
| 6,620,120 B2 | 9/2003 | Landry et al. |
| 6,638,477 B1 | 10/2003 | Treu et al. |
| 6,638,478 B1 | 10/2003 | Treu et al. |
| 6,649,063 B2 * | 11/2003 | Brugger ............... A61M 1/3462 210/645 |
| 6,702,561 B2 | 3/2004 | Stillig et al. |
| 6,733,676 B2 | 5/2004 | Takai |
| 6,743,201 B1 | 6/2004 | Doenig et al. |
| 6,746,606 B2 | 6/2004 | Pfeil et al. |
| 6,752,928 B2 | 6/2004 | Pfeil et al. |
| 6,780,322 B1 | 8/2004 | Bissler et al. |
| 6,821,441 B2 | 11/2004 | Pedrini et al. |
| 6,830,553 B1 | 12/2004 | Burbank et al. |
| 6,843,779 B1 | 1/2005 | Andrysiak et al. |
| 6,852,090 B2 | 2/2005 | Burbank et al. |
| 6,890,157 B2 | 5/2005 | Pfeil et al. |
| 6,918,886 B1 | 7/2005 | Bauermeister |
| 6,955,655 B2 | 10/2005 | Burbank et al. |
| 6,979,309 B2 | 12/2005 | Burbank et al. |
| 7,008,403 B1 | 3/2006 | Mallett |
| 7,074,332 B2 | 7/2006 | Summerton et al. |
| 7,112,273 B2 | 9/2006 | Weigel et al. |
| 9,072,830 B2 * | 7/2015 | Kelly .................. A61M 1/1696 |
| 9,364,602 B2 * | 6/2016 | Kelly .................. A61M 1/1696 |
| 2001/0032818 A1 | 10/2001 | Nikaido et al. |
| 2001/0035378 A1 | 11/2001 | Nikaido |
| 2001/0045395 A1 | 11/2001 | Kitaevich et al. |
| 2002/0017489 A1 | 2/2002 | Utterberg |
| 2002/0041825 A1 | 4/2002 | Scheunert et al. |
| 2002/0082728 A1 | 6/2002 | Mueller et al. |
| 2002/0103453 A1 | 8/2002 | Burbank et al. |
| 2002/0112609 A1 | 8/2002 | Wong |
| 2002/0147423 A1 | 10/2002 | Burbank et al. |
| 2003/0036719 A1 | 2/2003 | Giacomelli et al. |
| 2003/0105424 A1 | 6/2003 | Karoor et al. |
| 2004/0019313 A1 | 1/2004 | Childers et al. |
| 2004/0158189 A1 | 8/2004 | Tonelli et al. |
| 2004/0024304 A1 | 12/2004 | Brugger et al. |
| 2004/0024305 A1 | 12/2004 | Treu et al. |
| 2004/0024516 A1 | 12/2004 | Treu et al. |
| 2004/0024933 A1 | 12/2004 | Burbank et al. |
| 2004/0243049 A1 | 12/2004 | Brugger et al. |
| 2004/0267184 A1 | 12/2004 | Burbank et al. |
| 2004/0267185 A1 | 12/2004 | Weaver et al. |
| 2005/0000868 A1 | 1/2005 | Weigel et al. |
| 2005/0004502 A1 | 1/2005 | O'Mahony et al. |
| 2005/0010158 A1 | 1/2005 | Brugger et al. |
| 2005/0011823 A1 | 1/2005 | Delnevo et al. |
| 2005/0020958 A1 | 1/2005 | Paolini et al. |
| 2005/0020959 A1 | 1/2005 | Brugger et al. |
| 2005/0020960 A1 | 1/2005 | Brugger et al. |
| 2005/0131332 A1 | 1/2005 | Kelly et al. |
| 2006/0138049 A1 | 6/2006 | Kim et al. |
| 2007/0038191 A1 | 2/2007 | Burbank et al. |

FOREIGN PATENT DOCUMENTS

| | | |
|---|---|---|
| DE | 2901628 | 7/1980 |
| DE | 3122756 | 6/1982 |
| DE | 210425 | 6/1984 |
| DE | 3307830 | 6/1984 |
| DE | 4003452 | 8/1991 |
| DE | 4208054 | 10/1992 |
| DE | 4122754 | 1/1993 |
| DE | 19830928 | 5/1999 |
| DE | 19814695 | 10/1999 |
| DE | 19854338 | 6/2000 |
| DE | 10011208 | 9/2001 |
| DE | 1010146 | 7/2002 |
| EP | 0165751 | 12/1985 |
| EP | 0166920 | 1/1986 |
| EP | 0306241 | 3/1989 |
| EP | 0222709 | 5/1991 |
| EP | 0451429 | 10/1991 |
| EP | 0490212 | 6/1992 |
| EP | 0623357 | 11/1994 |
| EP | 0722744 | 7/1996 |
| EP | 0928615 | 7/1997 |
| EP | 0796998 | 9/1997 |
| EP | 0659091 | 12/2000 |
| EP | 1097724 | 5/2001 |
| GB | 2110564 | 6/1983 |
| GB | 2246718 | 2/1992 |
| JP | S5115360 | 5/1976 |
| JP | S618057 | 1/1986 |
| JP | 62-22658 | 1/1987 |
| JP | 63-95063 | 4/1988 |
| JP | S6462167 | 3/1989 |
| JP | H02336268 | 8/1990 |
| JP | H0735413 | 2/1995 |
| JP | H7-313590 | 12/1995 |
| JP | H08504116 | 5/1996 |
| JP | H09327511 | 12/1997 |
| JP | 11-506962 | 6/1999 |
| JP | H11226120 | 8/1999 |
| JP | 2000-84071 | 3/2000 |
| JP | 2000-107283 | 4/2000 |
| JP | 2002-217908 | 8/2000 |
| JP | 2002119585 | 4/2002 |
| JP | 2003518964 | 6/2003 |
| JP | 2003275301 | 9/2003 |
| JP | 2004-205146 | 7/2004 |
| JP | 2004-209103 | 7/2004 |
| JP | 2006-500968 | 1/2006 |
| JP | 2006512138 | 4/2006 |
| RU | 1001945 | 3/1983 |
| RU | 1821222 | 6/1993 |
| WO | WO9411093 | 5/1994 |
| WO | 9640320 | 12/1996 |
| WO | 98/32477 | 7/1998 |
| WO | 00/09182 | 2/2000 |
| WO | 99/42150 | 2/2000 |
| WO | 00/31967 | 6/2000 |
| WO | 00/57925 | 10/2000 |
| WO | 00/57926 | 10/2000 |
| WO | 00/57927 | 10/2000 |
| WO | 00/64510 | 11/2000 |
| WO | 01/24849 | 4/2001 |
| WO | 01/37786 | 5/2001 |
| WO | 01/37894 | 5/2001 |
| WO | 01/37895 | 5/2001 |
| WO | 01/37900 | 5/2001 |
| WO | 0137895 | 5/2001 |
| WO | WO0137786 | 5/2001 |
| WO | 01/41831 | 6/2001 |

(56) References Cited

FOREIGN PATENT DOCUMENTS

| WO | 01/41832 | 6/2001 |
|---|---|---|
| WO | 01/42758 | 6/2001 |
| WO | 01/45769 | 6/2001 |
| WO | 0141833 | 6/2001 |
| WO | 01/47576 | 7/2001 |
| WO | 01/47581 | 7/2001 |
| WO | 02/070042 | 9/2002 |
| WO | 03011376 | 2/2003 |
| WO | 03041764 | 5/2003 |
| WO | 2004082731 | 9/2004 |
| WO | 2005042065 | 5/2005 |
| WO | 2005044339 | 5/2005 |
| WO | 2005044340 | 5/2005 |
| WO | 06/105605 | 10/2006 |
| WO | 2007074425 | 7/2007 |

OTHER PUBLICATIONS

Japanese Office Action dated Sep. 14, 2015 for corresponding Japanese Appln. No. 12014-21619 (5 pages).
Japanese Office Action dated Jan. 10, 2014 for related Japanese Application No. 2013-000322.
Japanese Office Action dated Sep. 29, 2014 in corresponding Japanese Application No. 2011-163710.
Japanese Office Action dated Jan. 30, 2014 for related Japanese Application No. 2011-163710.
Japanese Office Action dated Apr. 10, 2015 in corresponding Japanese Application No. 2013-169818.
Japanese Office Action dated Jun. 30, 2014 for related Japanese Application No. 2013-169818 (10 pages).
Japanese Office Action dated Sep. 18, 2012 for corresponding Japanese Application No. 2009-527618.
European Office Action dated Mar. 14, 2013 for corresponding European Application No. 11075126.0.
European Office Action dated Nov. 10, 2014 for corresponding European Application No. 111185112.7 (5 pages).
European Office Action dated Jan. 21, 2016 for corresponding European Application No. 11075128.6 (6 pages).
European Office Action dated Jun. 6, 2013 for related European Application No. 11075125.2.
European Office Action dated Feb. 12, 2013 for related European Application No. 11075124.5.
European Office Action dated Aug. 20, 2013 for related European Application No. 11075128.6.
European Office Action dated Apr. 18, 2013 for related European Application No. 11075127.8.
European Office Action dated Oct. 6, 2014 for related European Application No. 11185090.5-1651 (5 pages).
European Office Action received by foreign associate dated Sep. 26, 2013 for related European Application No. 11075129.4.
European Office Action received by foreign associate dated Sep. 30, 2013 for related European Application No. 11075130.2.
European Office Action received by foreign associate dated Sep. 30, 2013 for related European Application No. 11185112.7.
European Office Action received by foreign associate dated Sep. 26, 2013 for related European Application No. 11185090.5.
European Search Report dated Jul. 3, 2015 for corresponding European Application No. 15156422.6 (8 pages).
European Search Report for European Application No. 11 07 5124 dated Mar. 16, 2012.
European Search Report for European Application No. 11 07 5125 dated Mar. 26, 2012.
European Search Report for European Application No. 11 07 5126 dated Mar. 22, 2012.
European Search Report for European Application No. 11 07 5127 dated Mar. 28, 2012.
European Search Report for European Application No. 11 07 5128 dated Apr. 3, 2012.
European Search Report for European Application No. 11 07 5129 dated Mar. 29, 2012.
Mexican Office Action for Application No. PA/a/2006/005045 dated May 17, 2012.
Extended European Search Report for European Application No. 11075130.2 dated Mar. 15, 2012.
Extended European Search Report for European Application No. 11185112.7 dated Dec. 20, 2011.
Extended European Search Report for European Application No. 11185090.5 dated Dec. 22, 2011.
European Office Action dated Aug. 7, 2014 for related European Appln. No. 11075128.6 (5 pages).
International Search Report and the Written Opinion for International Application No. PCT/US2008/064086 dated Jan. 27, 2009.
Manns et al., The acu-menTM: A new device for continuous renal replacement therapy in actue renal failure, Kidney International, 1998, pp. 268-274, vol. 54.
Office Action issued in related Japanese Patent Application No. 2016-37500 dated Jan. 18, 2017.
European Extended Search Report—Appl. No. 16164103.0-1651 dated Jul. 8, 2016—9 pages.
Office Action issued in corresponding Japanese Patent Application No. 2014-223121 dated May 20, 2016.
Mexican Office Action dated May 19, 2016 in corresponding Mexican application No. MX/a/2011/010561 (4 pages).
Office Action issued in related Japanese Patent Application No. 2014-223121 dated Feb. 1, 2017.
Office Action issued in related Japanese Patent Application No. 2016-037500 dated Oct. 2, 2017.
Penultimate Office Action issued in related Japanese Patent Application No. 2016-037501 dated Oct. 2, 2017.
Office Action (along with English translation) issued in related Japanese Patent Application No. 2016-37501 dated Jan. 25, 2017.
European Search Report—Appl. No. 16197425.8-1651—dated Mar. 17, 2017—9 pages.

* cited by examiner

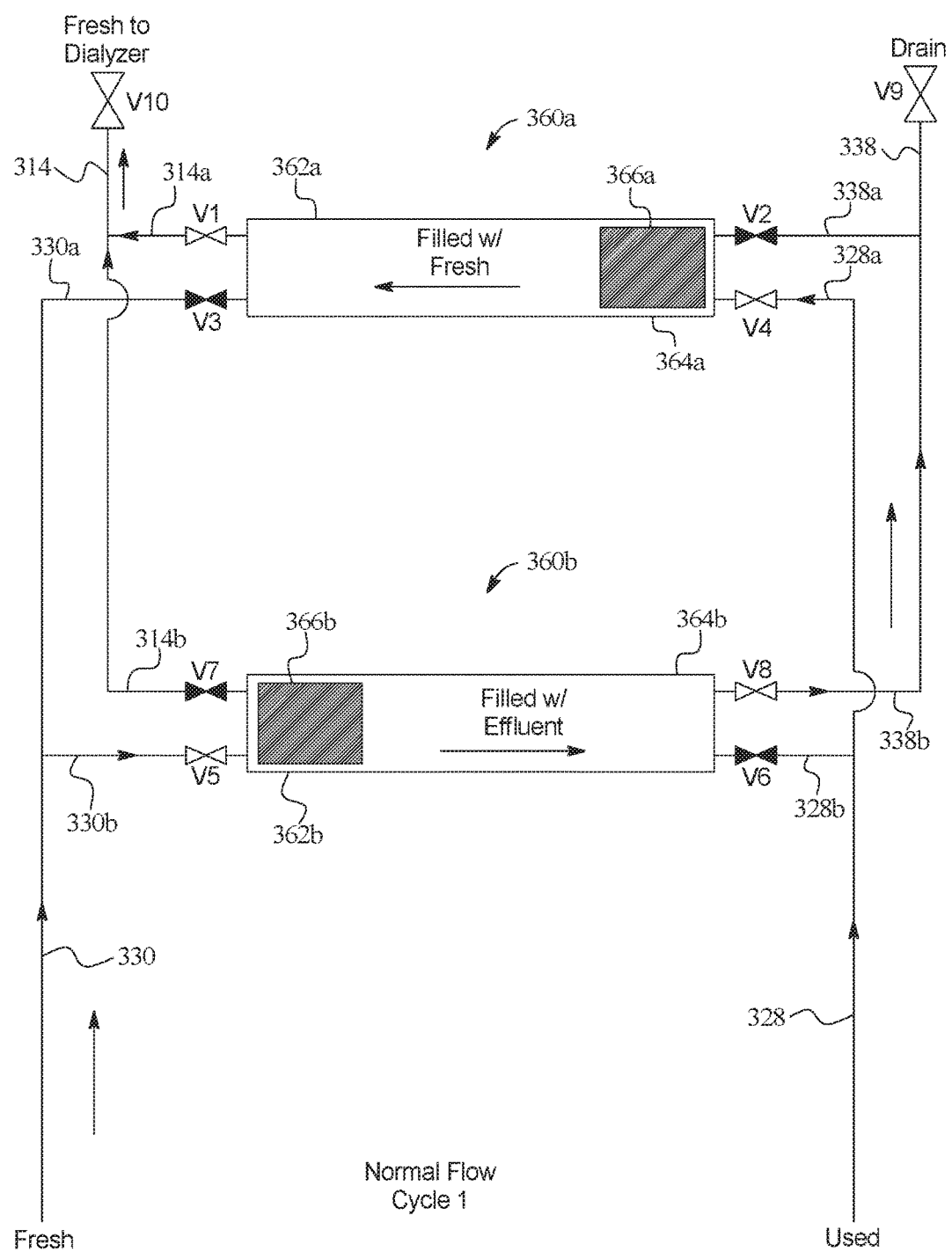

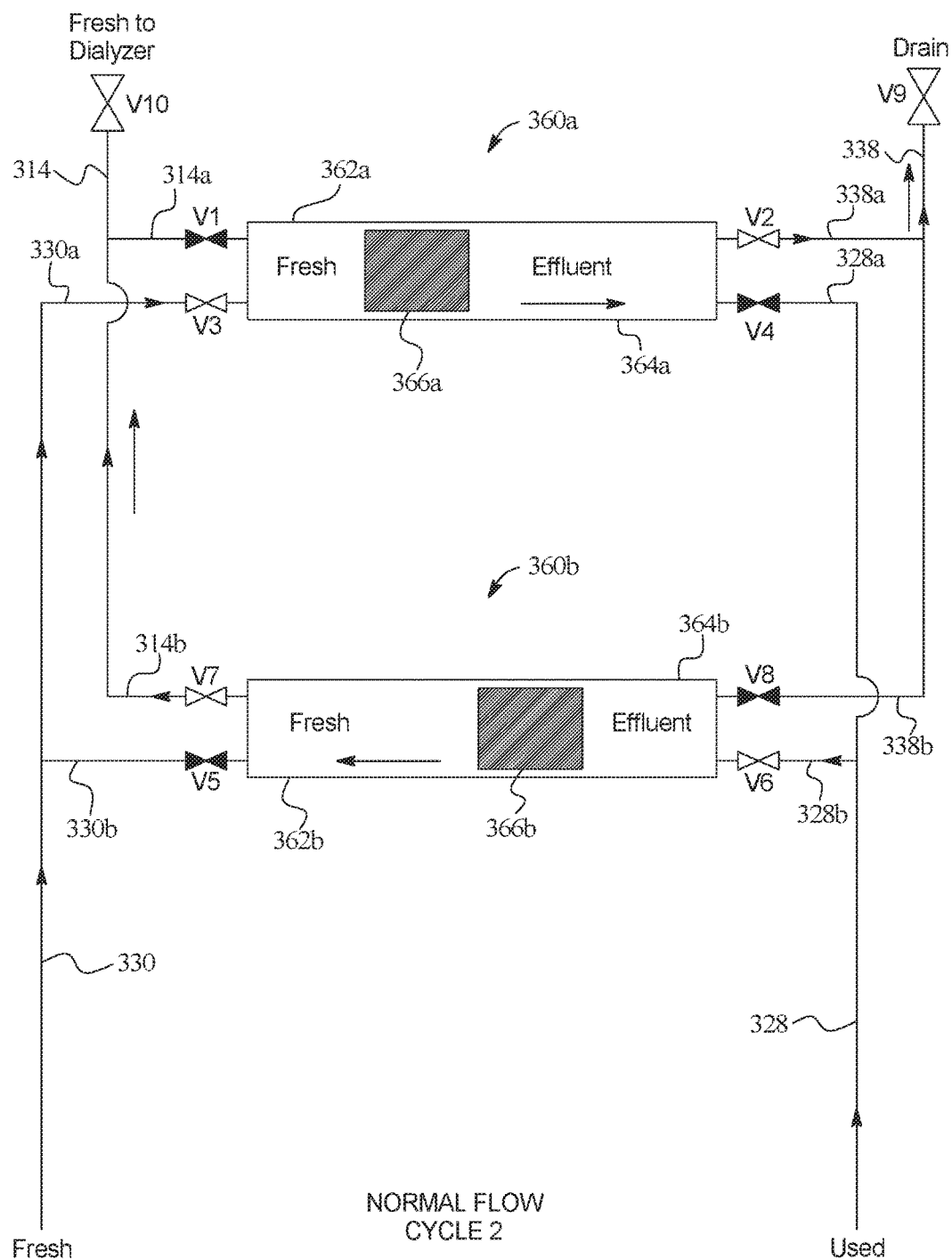

SYSTEMS AND METHODS FOR PRIMING HEMODIALYSIS USING DIALYSIS FLUID

PRIORITY CLAIM

This application claims priority to and the benefit as a continuation application of U.S. patent application Ser. No. 13/749,309, entitled, "Systems and Methods for Priming Sorbent-Based Hemodialysis Using Dialysis Fluid", filed Jan. 24, 2013, which is a continuation application of U.S. patent application Ser. No. 13/222,622, entitled, "Systems And Methods For Priming Sorbent-Based Hemodialysis", filed Aug. 31, 2011, now U.S. Pat. No. 9,072,830, which is a continuation application of U.S. patent application Ser. No. 10/982,170, entitled, "High Convection Home Hemodialysis/Hemofiltration And Sorbent System", filed Nov. 4, 2004, now U.S. Pat. No. 8,029,454, which claims priority to and the benefit of U.S. Provisional Patent Application No. 60/517,730, filed Nov. 5, 2003, entitled, "High Convection Home Hemodialysis/Hemofiltration And Sorbent System", the entire contents of each of which are hereby incorporated by reference and relied upon.

BACKGROUND

The present invention relates generally to medical treatments. More specifically, the present invention relates to medical fluid treatments, such as the treatment of renal failure and fluid removal for congestive heart failure.

Hemodialysis ("HD") in general uses diffusion to remove waste products from a patient's blood. A diffusive gradient that occurs across the semi-permeable dialyzer between the blood and an electrolyte solution called dialysate causes diffusion. Hemofiltration ("HF") is an alternative renal replacement therapy that relies on a convective transport of toxins from the patient's blood. This therapy is accomplished by adding substitution or replacement fluid to the extracorporeal circuit during treatment (typically ten to ninety liters of such fluid). That substitution fluid and the fluid accumulated by the patient in between treatments is ultrafiltered over the course of the HF treatment, providing a convective transport mechanism that is particularly beneficial in removing middle and large molecules (in hemodialysis there is a small amount of waste removed along with the fluid gained between dialysis sessions, however, the solute drag from the removal of that ultrafiltrate is not enough to provide convective clearance).

Hemodiafiltration ("HDF") is a treatment modality that combines convective and diffusive clearances. HDF uses dialysate to flow through a dialyzer, similar to standard hemodialysis, providing diffusive clearance. In addition, substitution solution is provided directly to the extracorporeal circuit, providing convective clearance.

Home hemodialysis ("HHD") has declined in the last twenty years even though the clinical outcomes of this modality are more attractive than conventional hemodialysis. One of the drawbacks of home hemodialysis is the need for a dedicated water treatment, which includes equipment, water connection and drainage. Installing and using those components is a difficult and cumbersome task that can require a patient's home to be modified. Nevertheless, there are benefits to daily hemodialysis treatments versus bi- or tri-weekly visits to a treatment center. In particular, a patient receiving more frequent treatments removes more toxins and waste products than a patient receiving less frequent but perhaps longer treatments.

SUMMARY

The present invention provides a system, method and apparatus that performs a daily renal replacement therapy, which combines both diffusion and convection transport from the patient. In hemodialysis, high flux membranes can in some cases backfilter fluid from the dialysate to the blood even though, on balance, net fluid flow is from the patient. That backfiltration is due to a pressure differential between the inlet/outlet of the blood and inlet/outlet of dialysate in specific areas of the dialyzer. The present invention capitalizes on that phenomenon.

In one embodiment, two small high flux dialyzers are connected fluidly to the cassette in series. Dialysate and blood flow in a countercurrent manner through the dialyzers and extracorporeal circuit. In one embodiment, however, the dialysate flow through the dialyzers can alternatively be co-current or in the same direction as the flow of blood through the blood circuit. A restriction is placed between the two dialyzers in the dialysate flow path. The restriction is variable and adjustable in one preferred embodiment to account for different treatment conditions or to be adjusted during a single treatment. The restriction is alternatively a simple fixed restriction, such as an orifice plate with a smaller orifice. Due to the restriction between the filters, a positive pressure is built in the venous dialyzer, causing a high degree of intentional backfiltration. Depending on the size of the restriction between the dialyzers, that backfiltration causes a significant flow of dialysate through the high flux venous membrane directly into the blood. That backfiltered solution is subsequently ultrafiltered from the patient from the arterial dialyzer. The movement of dialysate into the blood in the venous filter and removal of dialysate from the arterial dialyzer causes a convective transport of toxins from the patient. Additionally, the dialysate that does not move directly into the patient but instead flows across the membranes of both dialyzers provides a diffusive clearance of waste products.

The system therefore acts as a hemodiafiltration system providing both convective and diffusive clearances. The system in one embodiment is configured for home use, wherein at least a portion of the dialysate and extracorporeal flow paths is sterilized and provided in a disposable cassette, which is loaded into a home pumping apparatus. For example, the system can be a portable device that uses an integrated disposable fluid management system or cassette and a sterile, prepackaged solution to perform a hemodialysis therapy. The system in one embodiment is particularly suited for home use because of its compact size, ease of therapy setup, and lack of need for a water treatment and dialysate proportioning system.

Unlike current hemodialysis machines, the patient does not have to manage complicated tubing sets. The patient simply places the cassette into the renal failure therapy machine, connects solution bags to the machine and starts an automated priming sequence. When the priming is complete, the patient connects the bloodlines to the patient's body and starts the dialysis therapy. At the end of treatment the patient's blood is returned to the patient's body. The patient merely discards the ultrafiltrate ("UF") waste and the therapy ends without the patient having to perform a complicated disinfection procedure.

In one embodiment, the cassette-based system operates as follows. A blood pump pulls blood from the patient, pushes it through both hemodialyzers and returns the blood to the patient. Dialysate solution is drawn from a dialysate source and heated to a desired patient temperature. Infusion pumps pump fresh dialysate from the bag into the venous dialyzer. The restriction is placed in the dialysate flow path between the two dialyzers to facilitate the backfiltration of dialysate into the bloodline via venous dialyzer. The restriction is preferably variable but alternatively fixed.

The flow out of the infusion pumps pushes fluid at the restriction creating a positive pressure in the venous hemodialyzer. Using a high flux membrane, the backpressure forces a portion of the dialysate, e.g., fifty percent or more, into the patient's bloodline. The rest of the dialysate flows through to the arterial dialyzer. Drain pumps remove from the flow paths an equivalent amount of fluid as delivered by the infusion pumps as well as any fluid loss that the patient has gained in the interdialytic period. The spent fluid and ultrafiltrate are then put into a drain bag or dumped to an external drain.

The cassette-based dialysate pumps are controlled to balance the dialysate flow to the venous dialyzer with the dialysate flow from the arterial dialyzer so that the patient fluid status is maintained. Due to that balancing capability an identical amount of fluid is ultrafiltered from the patient in the arterial hemodialyzer as is backfiltered into the extracorporeal circuit in the venous dialyzer. Ultrafiltering this fluid from the blood creates a solute drag effect providing a convective transport of toxins similar to hemofiltration. Since some dialysate flows along the fiber in the venous to arterial dialyzer there is also diffusive transport of toxins from the blood.

Air bubble detectors, heating elements, pressure sensors, temperature sensors, etc., are also integrated into the cassette for both the dialysate management and extracorporeal blood sides as necessary to allow for a safe treatment for the patient and reliable operation of the system.

Recently published studies show that ultrapure dialysate produces better outcomes when compared to standard dialysate. The prepackaged, sterilized dialysate used in one embodiment of the present invention may produce outcomes that are as good as, if not better than, ultrapure dialysate. It should be appreciated however that the present invention is not limited to the use of prepackaged dialysate bags, but instead, may use dialysate prepared on-line or at home. The advantage of the online system to the patient is to eliminate the solution bags and the space they consume. The dialysate, whether supplied from a sterilized bag or made online, may also be recirculated in one or more loops using one or more charcoal or sorbent cartridge.

One preferred at home generation system is described herein. That system uses a reservoir, such as a five liter bag of sterile dialysate installed in a rigid container. A shunt is placed across the dialyzers at start-up for rinsing and priming. During treatment, a sorbent cartridge that operates using an urea exchange or a binding urea is placed in the post dialyzer or ultrafilter ("UF") loop. The sorbents may remove other substances, such as beta 2 microglobulin or phosphate, etc. A series of infusion pumps simultaneously pull dialysate from the sterile bag, through a heater, through an ultrafilter and through the shunt to the sorbent cartridge. If necessary, an infusate such as a gamma sterilized infusate that includes calcium, magnesium, and potassium is added to the dialysate reservoir.

After the solution is heated and ready for treatment, the blood treatment machine prompts the user to install the cassette. The blood circuit can be primed with a saline bag hooked via the arterial bloodline or by backfiltering dialysate through the blood treatment venous filter. Air bubble detectors, heating elements, pressure sensors, temperature sensors, etc., are integrated into the cassette for both the dialysate and extracorporeal blood circuits as necessary to enable a safe treatment for the patient and a system that operates reliably.

The patient is then hooked to the arterial and venous needles and the treatment begins. For short therapies, the dialysate flow can be relatively high, for example, three hundred ml/min for three hours or one hundred ml/min for up to eight hours. The dialysate/UF flow control pumps control the flow to and from the dialyzers. By increasing the frequency of the pumps that pull the effluent dialysate from the arterial dialyzer, the fluid accumulated in the patient in the interdialytic period is removed. Portions of the dialysate/UF flow control pumps are integrated into the cassette along with a portion of the blood pump in one embodiment or are alternately provided separate from the cassette and integrated into the machine.

Due to the impracticality of hanging and storing bags, solution-bag based systems are limited to a total practical amount of dialysate per treatment. The sorbent-based fluid regeneration system enables a therapy that uses more dialysate and thereby provides enhanced waste clearance. Providing an increased amount of dialysate beneficially enhances the clearance of waste products from the renal patient. For example, the sorbent cartridge could be used for a four hour treatment at two hundred to two hundred fifty ml/min dialysate flow or about fifty liters of dialysate over the entire treatment, which would provide an increased volume of dialysate and better waste clearance over other hemofiltration systems. The sorbent system is also applicable to the hemofiltration systems described herein, making even predilution HF possible. For hemofiltration, an additional reusable ultrafilter is provided to maintain redundancy of bacteria and endotoxin removal.

The sorbent-based regeneration system is particularly suited for home use because it eliminates the need to store numerous solution bags, eases therapy setup and does not require a connection to the patient's water tap. Also, the patient does not have to connect a tubing set. The patient instead places the cassette into the machine, adds an initial five liter bag of sterile dialysate to the reservoir and starts the automated priming sequence. When the priming is complete, the patient connects himself/herself to the blood circuit and starts the dialysis therapy.

The portable device, the use of prepackaged solutions or an on-line fluid generation system and the use of a disposable set each provide dialysis patients with the flexibility and freedom that previously has only been available to peritoneal dialysis patients. Because there is no dedicated water hookup and the present machines are small, it is possible for a patient using the present systems to travel and perform blood therapy dialysis sessions on the road. Many of the systems and methods described herein can be adapted to work with in-center solutions, and many of the aspects of the present invention are not limited to home use.

High convection hemodialysis is believed to be more effective than conventional hemofiltration because it has convective clearance in addition to the diffusive transport of toxins. The therapy is expected to provide good waste clearance of small, middle and large molecules from even end-stage renal patients.

The device is well-suited for use in hospitals for acute patients for situations in which a required water supply and dialysis proportioning system are unavailable. The present device is easier to set up and use in an intermittent acute setting.

The present invention provides multiple methods and apparatuses for not only controlling the amount of dialysate or substitution fluid that is delivered to the extracorporeal circuit or dialyzer but also for accurately controlling the amount of ultrafiltrate removed from the patient. The various alternatives can be divided into three main types. One type of control used is a pneumatic control based on Boyle's Law. Here, the fluid pumps are placed in fluid communication with a known volume of air. The system uses Boyle's Law to place into an equation a series of known or measured values to calculate accurately the amount of fluid (e.g., versus air) from a pump chamber pumped to the patient. The method and apparatus use fluid and air pressure signals generated and converted to numbers that are placed into an equation. The equation yields the fluid volume pumped per cycle or stroke of the pump. The Boyle's law system in one embodiment provides accurate information on an end stroke or pump cycle basis but not necessarily on a real time basis. The present invention also includes a system and method based on Boyle's Law that generates flow rate data on a real time basis.

A second large category of volumetric control includes the use of a balancing device. Many embodiments for employing such balancing device are discussed below. The balancing device embodiments may be parsed into two main sub-groups. One sub-group uses a single balancing device. Another sub-group includes dual balancing devices.

The present invention also teaches and discloses a plurality of different types of balancing devices. In one embodiment, the system employs one or two balancing chambers. In another embodiment, the system employs one or two balancing tubes. The balancing tubes include a tubular housing with a piston or ball-like separator within the housing. The separator acts similarly to the membrane or diaphragm of the balance chamber.

A third type of balancing device is one or more tortuous path. The tortuous path is defined in one embodiment by a disposable cassette as an elongated channel. The diameter or cross-sectional area of the channel is configured so that bulk movement of fresh or effluent dialysate can efficiently move an existing bulk of fluid within the tortuous path. That is, fresh dialysate in bulk moves a bulk of spent or effluent dialysate currently residing in the path to drain. In the next cycle, spent or effluent dialysate in bulk pushes the bulk of fresh fluid just introduced into the tortuous path to the patient or dialyzer. The cross-section and the length of the path are configured to minimize an amount of mixing of the fresh and spent fluids at the ends of the bulks of fluid.

The various volumetric balancing devices can be used with many different types of pumps, such as a peristaltic pumps, membrane pumps, gear pumps or a combination thereof. A single pump may be used with the balancing devices. Separate fresh and spent dialysate pumps may be used alternatively. Further, a separate ultrafiltrate pump is also contemplated and discussed, which enables the main pump(s) to be dedicated to pumping an equal volume of fluid to and from the patient.

The third major type of fluid management uses a scale to measure the amount of fluid delivered to the patient and the amount of fluid removed from the patient. In an embodiment illustrated below, fluid bags are placed on a stand, which is coupled to a shaft. At one end, the shaft couples to a rolling diaphragm. The rolling diaphragm, in combination with other apparatus, defines a closed but variable volume. As the weight in the fluid bags fluctuates, a pressure within the volume also fluctuates. A pressure sensor senses the pressure and the controller or processor of the machine processes the signal from the pressure sensor to develop a corresponding weight signal. The weight signal is then used to determine how much fluid has been delivered and or removed from the patient. In one embodiment, fresh and spent fluid bags are measured by the same weight sensing device, so that the system expects to see a net overall weight gain over time due to the ultrafiltrate removed from the patient. A load cell could also be used for this application.

As illustrated in detail below, the present invention provides multiple embodiments for other components of the systems and methods of the present invention, such as the fluid heater, the balancing devices, the disposable cassette, bag positioning and other important features of the present invention. For example, the present invention includes an access disconnection sensor ("ADS"), which can detect when either the arterial or venous needle has been removed inadvertently from the patient during treatment. Further, various pressure relief schemes, integrity tests, etc., are discussed herein, which are important especially for a home-use machine, which the patient may be use while sleeping.

It is therefore an advantage of the present invention to provide a hemodialysis, hemofiltration or hemodiafiltration system usable in a home or clinic setting.

It is another advantage of the present invention to provide a cassette-based hemofiltration/hemodiafiltration system, which enables a patient at home to easily set up a sterile blood therapy system.

It is another advantage of the present invention to improve the effectiveness of renal failure blood treatment therapy.

Moreover, it is an advantage of the present invention to provide a renal failure blood therapy that employs convective and diffusive modes of clearance.

Still further, it is an advantage of the present invention to provide a renal failure blood therapy in which both diffusive and convective clearance modes are provided and wherein the percentage use of either mode can be varied.

Further still, it is an advantage of the present invention to provide a cassette-based blood therapy that is configurable in the field to perform either hemodialysis, enhanced convection hemodialysis, hemofiltration or hemodiafiltration.

Yet further, it is an advantage of the present invention to provide a blood therapy system with one or more therapy fluid circulation loops that optimize the consumption of fresh dialysate.

Still another advantage of the present invention is to provide a home renal failure blood treatment therapy that is configurable to operate with multiple different types of therapy fluid sources, such as solution bags, solution preparation units or on-line dialysate generation systems.

It is yet a further advantage of the present invention to provide a home renal failure therapy system operable with many types of systems that control accurately the amount of fluid exchanges and the amount of fluid or ultrafiltrate removed from the patient.

Still further, it is an advantage of the present invention to provide improved fluid volume control devices.

Additional features and advantages of the present invention are described in, and will be apparent from, the following Detailed Description of the Invention and the figures.

Additional features and advantages are described herein, and will be apparent from the following Detailed Description and the figures.

BRIEF DESCRIPTION OF THE FIGURES

FIGS. 27A to 27D are schematic flow diagrams illustrating the valve operation and associated flow outcomes of another method and apparatus for controlling the volume of fluid exchanged with the patient and the volume of ultrafiltrate removed from the patient, which includes dual balance tubes.

DETAILED DESCRIPTION

Overview

The present invention provides various apparatuses and methods for a home hemodialysis ("HHD") treatment that increases and enhances the amount of backfiltration during treatment. It is important to note that even though this system is designed for the home, it is also suitable for use in a clinic, acute renal treatment center or self-care center. The system uses a disposable fluid management system, which may include a disposable set having a disposable cassette or tubing organizer (referred to herein collectively as cassette). The cassette houses at least a portion of at least one of the dialysate and extracorporeal flow paths. In one embodiment, two small high flux dialyzers are connected fluidly and in series to the cassette. In one embodiment, dialysate and blood flow in a countercurrent manner through the dialyzers with respect to each other. A restriction is placed between the two dialyzers in the dialysate flow path. The restriction is variable and adjustable in one embodiment to account for different treatment conditions or to be adjusted during a single treatment. The restriction is alternatively fixed, such as an orifice plate with a restricting orifice.

Due to the restriction between the filters, a positive pressure is built in the venous dialyzer (first dialyzer to receive dialysate but second dialyzer to receive blood in countercurrent arrangement), intentionally causing a relatively high degree of backfiltration. Depending on the size of the restriction between the dialyzers, that backfiltration causes a significant flow (e.g., 10 to 70 percent of total dialysate flow) of dialysate through the high flux venous membranes and into the blood circuit. The backfiltered solution provides convective clearance. In one embodiment, ultrafiltrate is removed from the patient via the arterial dialyzer (first dialyzer to receive blood but second dialyzer to receive dialysate in countercurrent arrangement).

The diffusion of dialysate into the venous dialyzer and removal of dialysate from the arterial dialyzer causes a convective transport of toxins from the patient. Additionally, the dialysate that does not move directly into the extracorporeal circuit (e.g., the other percentage of the dialysate) but instead flows across the membranes of both dialyzers, providing a diffusive clearance of waste products. This system, referred to herein as an enhanced convection hemodialysis ("ECHD") system, is similar to a hemodiafiltration system, which provides both convective and diffusive clearances. The system in one embodiment is configured for home use, wherein at least a portion of the dialysate and extracorporeal flow paths is sterilized and provided in a disposable set, which is loaded into a machine having multiple pumps, a heater, valve actuators and the like.

Enhanced Convection Hemodialysis ("ECHD")

Figure 1:
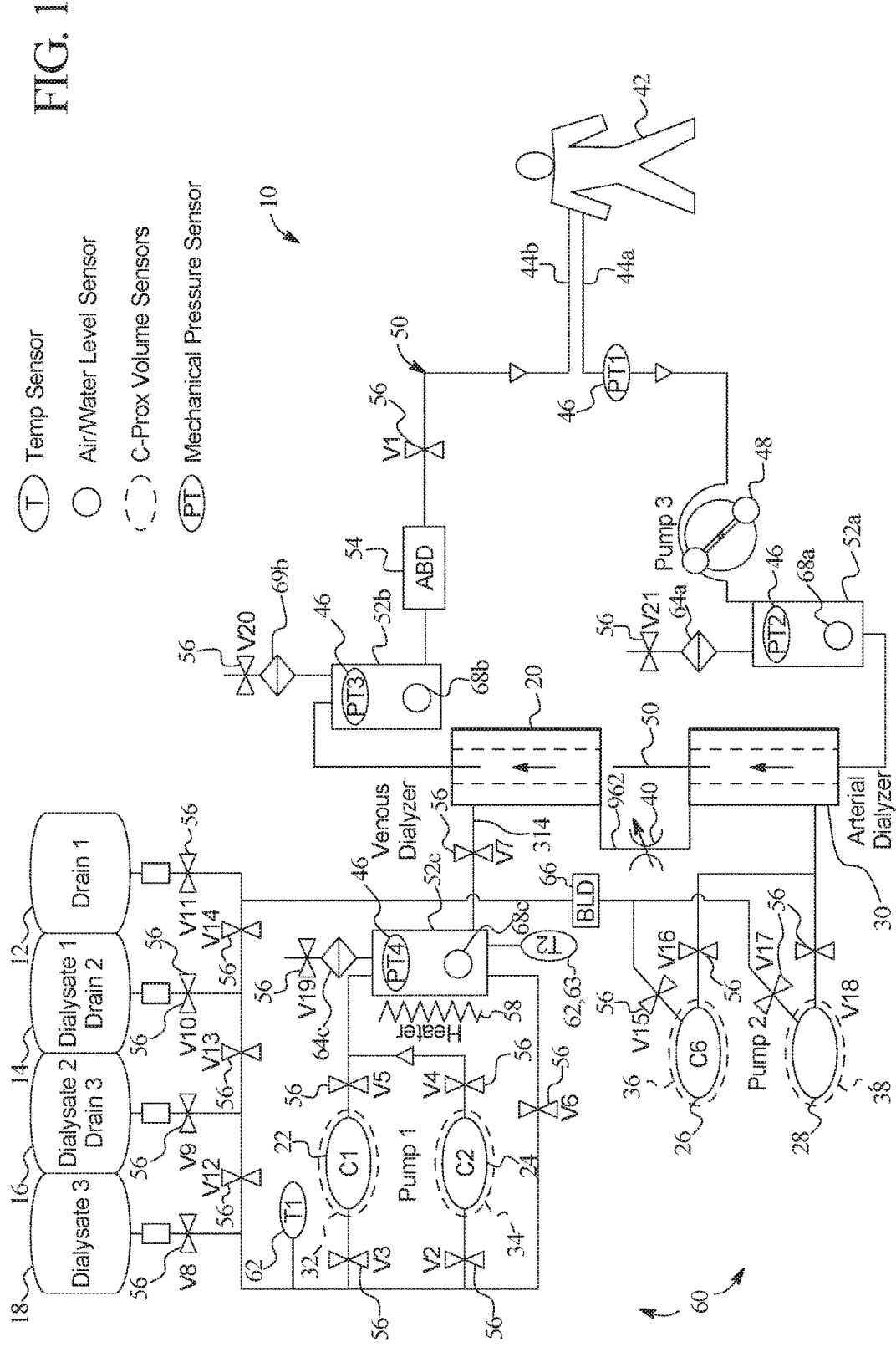
FIG. 1 is a schematic illustration of one embodiment of a renal failure blood treatment therapy system of the present invention that provides diffusive and convective clearance modes.

Referring now to the drawings and in particular to FIG. 1, one embodiment of the renal failure therapy system 10 of the present invention is illustrated. System 10 employs two or more high flux hemodialyzers, such as a venous dialyzer 20 and an arterial dialyzer 30. In one embodiment, hemodialyzers 20 and 30 are relatively small, e.g., on the order of one quarter to three meters2 of membrane surface area. Dialyzers or hemodialyzers 20 and 30 are relatively high flux dialyzers, e.g., having a UF coefficient of eight milliliters of water diffused per hour per millimeters Hg pressure or greater (as used herein, the term "flux" refers to the above UF coefficient, which measures the ease of water transport through the membrane, expressed in milliliters/hour/millimeter Hg).

As discussed above, hemodialyzers 20 and 30 cause backfiltration in the venous dialyzer 20 of a relatively large portion of the fresh dialysate. The backfiltered dialysate and the fluid accumulated during the interdialytic period is ultrafiltered or removed from the patient 42 via the arterial dialyzer 30. The fluid not backfiltered flows across the semi-permeable membrane in the arterial 30 and venous 20 dialyzers, enabling system 10 to provide both diffusive and convective removal of waste from the patient's blood.

In one home use and in-center embodiment shown in FIG. 1, sterile dialysate is stored in bags or containers 14, 16 and 18 (more than three solution bags may be used). System 10 in the illustrated embodiment employs pumps 22, 24, 26 and 28 that each operate with a respective volume measuring device 32, 34, 36 and 38. As described in detail below, various volumetric measuring devices are used alternatively with the systems of the present invention. One measuring device is a capacitance fluid volume sensor that measures the volume of fluid pumped through one of the pumps 22 to 28. That measurement in one embodiment informs a controller or microprocessor how much fluid (or air) has been pumped. The controller or microprocessor compares the actual amount of fluid pumped to an expected amount of fluid pumped and adjusts the pumping rates accordingly to make-up or back-off the delivery of new fluid to dialyzers 20 and 30 as needed. Alternatively or additionally, the capacitive measuring devices 32 to 38 can sense when a larger volumetric error in the system occurs and trigger, for example, an error message (e.g., when air becomes trapped in the system or a majority of a stroke length is missed).

It should be appreciated that the present invention is not limited to capacitive fluid volume measuring but can use instead other suitable types of volume measuring. Moreover, the present invention is not limited to volume measuring but instead can employ balancing devices that ensure a set amount of dialysate is pumped to the dialyzers, from the dialyzers and from the patient 42. Further alternatively, fluid pump management can be accomplished on a mass basis, via one or more scale. Still further, flowrate and volume pumped can be calculated based on a number of pump strokes, such as a number of peristaltic pump revolutions based on a number of steps of a stepper motor, based on a sensed amount of movement of a linear or rotating pump actuator or via a device that operates according to Boyle's Law. All of those measuring alternatives are included in the term "volume measuring device." Control using the volume measuring device can be closed loop, where the actual amount of fluid delivered is monitored, or open loop, where the scheme relies on the inherent accuracy of the pump and perhaps motion control feedback, such as a monitoring of number of step pulses sent to drive the motor, linear encoder feedback or rotary encoder feedback, etc.

FIG. 1 illustrates two pumps 22 and 24 for Pump Set 1 and two pumps 26 and 28 for Pump Set 2. It is important to note that a single pump may alternatively be used in place of each set of pumps, e.g., one to input dialysate to the dialyzers and one to remove dialysate from the dialyzers and UF from the patient, however, that configuration would create pulsatile or uneven flow, which is less desirable. In the illustrated configuration, a first pump of each set is pulling fluid from the pump set's source, while a second pump of each set is pushing fluid towards the pump set's destination. After that set of pump strokes, the roles of the pumps in the respective sets alternate, so that the first pump (now full of fluid) pushes fluid towards the pumps set's destination, while the second pump (now empty) pulls fluid from the pump set's source. The above cycle is repeated multiple times.

Pump Set 1 inputs fresh dialysate from bags 14 to 18 to the system 10 and Pump Set 2 removes a volumetric equivalent of the fluid pumped by Pump Set 1 and any fluid removed from patient 42 during the course of the treatment. As illustrated, fresh dialysate is pumped via pumps 22 and 24 from sources 14, 16 and 18 to the venous dialyzer 20. A restriction 40 is located between venous dialyzer 20 and arterial dialyzer 30. Restriction 40 builds pressure in venous dialyzer 20, so that a relatively large amount of fresh dialysate entering venous dialyzer 20 is forced through the walls of the membranes inside venous dialyzer 20 and into the extracorporeal or blood circuit 50. The other portion of the fresh dialysate entering venous dialyzer 20 flows across the membranes inside venous dialyzer 20, through restriction 40 and into arterial dialyzer 30.

Convective clearance occurs when a volumetric equivalent of the fluid backfiltered through venous dialyzer 20 is removed from the arterial dialyzer 30. Also, a diffusive transport of toxins occurs across both dialyzers 20 and 30 due to a diffusive gradient that exists between blood circuit 50 and the flow of dialysate. Over the total therapy, the total amount of fluid removed from the arterial dialyzer 30 is greater than the total amount of dialysate supplied to the venous dialyzer 20, accounting for an amount of UF removal prescribed for the therapy.

Example

The following example further illustrates one preferred therapy for the present invention. In the example, pumps 22 and 24 of Pump Set 1 infuse eighteen liters of dialysate from sources 14, 16 and 18 over two hours. Of that volume, one hundred ml/min of dialysate is backfiltered into the patient's blood circuit 50 through the membrane walls of venous dialyzer 20. Fifty ml/min of dialysate passes through the venous dialyzer 20, restriction 40 and into venous dialyzer 30. Pumps 26 and 28 of Pump Set 2 remove the total of eighteen liters of dialysate from bags 14, 16 and 18 plus any desired amount of fluid from the patient. Over two hours, twelve liters (100 ml/min multiplied by 120 minutes) of dialysate is backfiltered into the patient's blood through the venous dialyzer 20. Pumps 26 and 28 of Pump Set 2 remove that twelve liters, the six liters of dialysate that is not backfiltered into blood circuit 50 plus any fluid ultrafiltered from the patient.

The addition and removal of the twelve liters of dialysate from blood circuit 50 over the two hour therapy yields an overall convective removal according to the equation HF stdKt/V of ~2, which has been reported to be a suitable daily amount (see Jaber B T, Zimmerman D L, Leypoldt J K. Adequacy of Daily Hemofiltration: Clinical Evaluation of Standard Kt/V (stdKt/V), Abstract Hemodialysis International Volume 7, number 1, p 80, 2003. Additionally, over the course of two hours, six liters of dialysate was used for diffusive clearance via the dialysate gradient across the membranes of dialyzers 20 and 30. Note that the dialysate flow rates and percent convective versus diffusive could be higher or lower than those used in the example.

Introduction to Disposable Cassette

Figure 2:
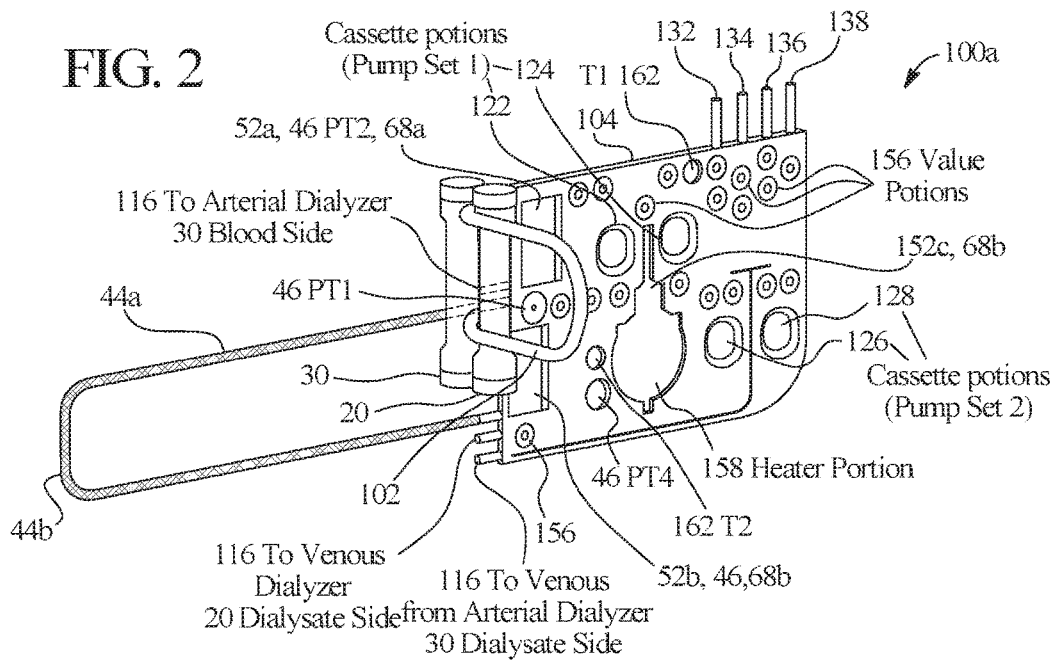
FIGS. 2 and 3 are perspective views of one embodiment of a disposable cassette and associated flow components for use with the blood treatment therapies described herein.
Figure 3:
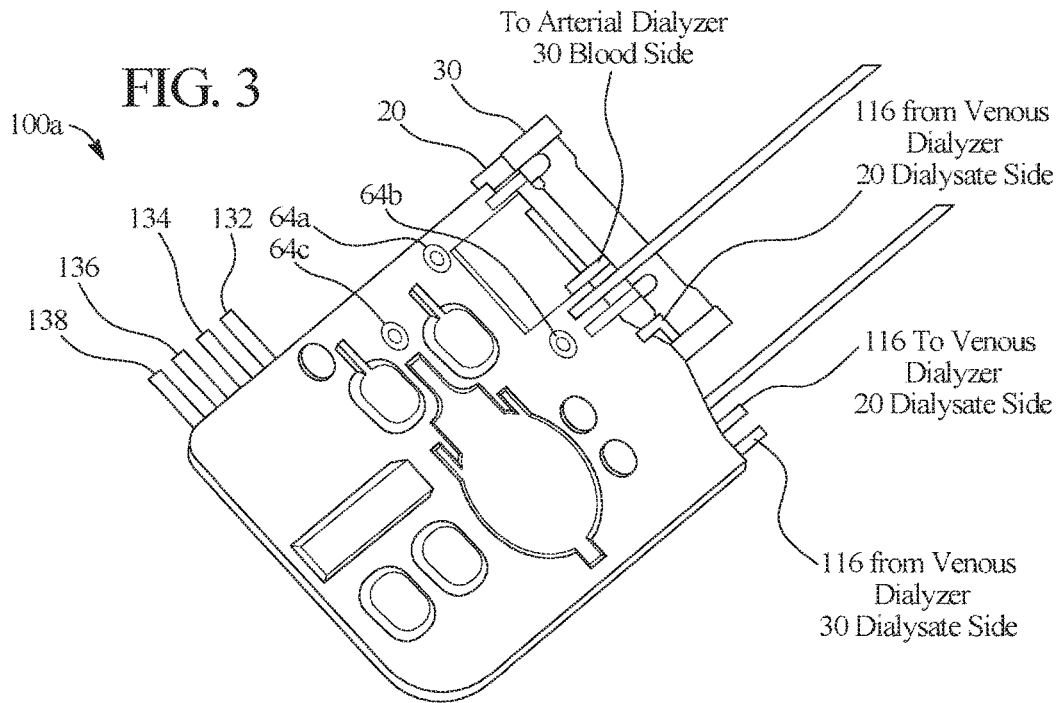

Referring additionally to FIGS. 2 and 3, dialyzers 20 and 30 as well as many other flow components described herein are provided in one preferred embodiment attached to a disposable cassette. Disposable cassette 100a can otherwise be referred to as an organizer, disposable, disposable set, etc. Disposable cassette 100a includes at least a portion of the extracorporeal circuit 50 and dialysate flow path 60 (see FIG. 1) for the renal failure therapy treatment (e.g., all of extracorporeal circuit 50 is integrated into cassette 100a with the exception of the tubing going to and from the patient as illustrated in FIGS. 2 and 3). Disposable cassette 100a provides a space efficient apparatus for handling the dialysate or therapy fluid flow portions of the many pumps and valves described herein, which are actuated pneumatically or mechanically as described below. Cassette 100a is therefore well suited for home use, where space, capability and resources are limited.

In one preferred embodiment, disposable cassette 100a and associated attached tubing are gamma sterilized and sealed prior to use. Alternatively, sterilization via ethylene oxide or ebeam is employed. The patient or operator opens the seal just prior to use, inserts cassette 100a into the therapy machine for a single use and then discards the cassette 100a and associated tubing. While cassette 100a and flow paths 50 and 60 are intended for a single use in one embodiment, cassette 100a and flow paths 50 and 60 could be reused with suitable disinfection and/or sterilization.

Incorporation of Cassette and ECHD System

Referring to FIGS. 1 to 3, beginning from the arterial access 44a of the patient 42, the extracorporeal or blood circuit 50 includes a pressure sensor 46, labeled PT1. PT1 is alternatively a pressure switch with the ability to stop blood flow prior to reaching blood pump 48. As a safety measure, system 10 in one embodiment includes a multitude of electrodes (not shown), such as two to four electrodes, which provide an access disconnection sensor, which is integrated half in the arterial line 44a and half in the venous line 44b to detect access disconnection of patient 42 from the system 10. An alternative mechanism for detection of accidental needle disconnections is the use of a conductive blanket underneath the patient's access. The presence of blood changes the conductivity of the blanket and sets off an alarm and stops the pumps.

Blood pump 48 is peristaltic pump 48 in one embodiment and is located between pressure sensor PT1 and a drip chamber 52a with integral pressure transducer 46, labeled PT2. The drip chambers 52a to 52c remove air from the fluids passing through the drip chambers. One, a multiple of or all the drip chambers 52a to 52c in an alternative embodiment includes an associated level sensor 68a to 68c. Those sensors are connected to or integrated into the associated drip chambers. Level sensors 68a to 68c sense and indicate the level or height of dialysate or therapy fluid in the dialyzer. Blood pump 48 is alternatively a volumetric pumping device other than a peristaltic pump, such as a diaphragm pump or centrifugal pump. Blood pump 48 can also be bidirectional for system priming as discussed below. Pressure sensor PT2 46 is alternatively not associated with a drip chamber, where for example pressure transducers are used instead. Pressure sensors PT1 and PT2, drip chamber 52a as well as the tubing 102 for peristaltic pump 48 are all connected to cassette 100a.

After drip chamber 52a, blood flows out of the housing 104 of cassette 100a into a the relatively small, high flux dialyzer arterial dialyzer 30. As seen in FIG. 2, arterial dialyzer 30 and venous dialyzer 20 are attached to an end of housing 104 of cassette 100a. Blood then flows from the arterial dialyzer 30 to the venous dialyzer 20, back into housing 104 of cassette 100a and through a second drip chamber 52b. Drip chamber 52b also has an integral pressure sensor 46, labeled PT3. PT3 is alternatively provided without a drip chamber when, for example, pressure transducers that coupled directly to the line are used instead.

An air bubble detector 54 labeled ABD is located downstream from drip chamber 52b in blood line 50. A venous line clamp or valve 56, labeled V1, which may be cassette-based or provided external to cassette 100a, and which shuts down blood flow if air is detected in line 50 by detector 54, is located between the air detector 54 and arterial access 44b, which returns blood to patient 42. An air level sensor (not illustrated) on drip chamber 52b is used alternatively or in addition to ABD 54. To detect air in the blood, a level detect scheme is alternatively or additionally provided with drip chamber 52b or pressure transmitter 46, labeled PT3. For example, an ultrasonic sensor can be placed on opposite sides of the drip chamber. The sensor generates a signal that depends upon the percentage of air in the blood that passes between a transmitting and receiving positions of the sensor. Under normal operation, when no air is present, the blood within drip chamber 52b resides at a relatively steady level, although level fluctuations do occur due to changes in pressure, amount of blood pumped, etc. A threshold level of blood in chamber 52b does exist below which the blood should not drop. When air in the blood lines is present, the blood level in the chamber 52b is lower than a threshold level, triggering an alarm from the alternative air/blood detector. It is important to note that an air detector and line clamp may be used on line 44a, if required by rinse, prime or blood rinseback.

Dialysate flow path 60 is also located primarily in the housing of organizer or cassette 100a. The dialysate is supplied initially in dialysate or therapy fluid supply bags 14, 16 and 18. In alternative embodiments shown below in connection with FIGS. 4 and 9 to 11, the source is an on-line source or other type of non-prepackaged source. In the embodiment illustrated in FIG. 1, a minimum of one infusion bag is provided and in one preferred embodiment multiple bags, such as three sources 14 to 18 are provided. FIG. 1 also illustrates that the system is provided initially with an empty drain bag 12, which is filled with spent solution from the supply bag 14, 16 or 18 that is used first. After the first two supply bags 14, 16 or 18 are drained, they become the drain bags for the second and final solution bags, respectively. Because the therapy in the end removes more fluid than is inputted, each of the supply bags 14 to 18 is used to receive spent fluid and UF. The bag sequencing is controlled as illustrated by valves 56, labeled V8 to V14.

Dialysate or therapy solution flows from one of sources 14 to 18 to the volumetric diaphragm pumps 22 and 24 of set 1. The volumetric accuracy of the pumps is confirmed by monitoring. As discussed above, it is desirable to use two alternating solution delivery pumps 22 and 24 to limit the amount of pulsatile flow. As a safety measure, the diaphragms of each of the pumps 22 to 28 are configured so that if they leak, the can only leak externally. Any leaks collected externally from pumps 22 to 28 is then diverted towards a moisture sensor built into the cassette 100*a*, machine and/or cassette/machine interface, which senses such leak and signals: (i) an alarm; (ii) to shut down pumps 22 to 28 and 48; and (iii) to take any other appropriate action.

Suitable pneumatically and mechanically driven medical fluid pumps and diaphragms therefore are described in commonly owned U.S. Pat. No. 7,238,164, entitled Systems, Methods And Apparatuses For Pumping Cassette-Based Therapies, filed Dec. 31, 2002, the teachings of which are incorporated herein by reference. The pumps and pumping technology currently used in the HomeChoice® series of APD devices, as embodied in U.S. Pat. No. 5,431,626 and its associated family of patents, the teachings of each of which are incorporated herein by reference, are also suitable, as are various pumping technologies described in commonly owned U.S. Pat. No. 6,814,547, entitled "Medical Fluid Pump", filed May 24, 2002, the teachings of each of which are incorporated herein by reference.

As discussed above, each of the pumps 22 to 28 operates individually with a volume measuring device 32 to 38. In one preferred embodiment, volume measuring devices 32 to 38 are capacitance fluid volume sensors, indicated in FIG. 1 by dashed lines representing the associated capacitor plates. One embodiment of a capacitance sensor is disclosed in greater detail in the U.S. patent entitled, "Capacitance Fluid Volume Measurement," U.S. Pat. No. 7,107,837, filed on Jan. 22, 2002, incorporated herein by reference. That capacitance sensor uses capacitance measurement techniques to determine the volume of a fluid inside of a chamber. As the volume of the fluid changes, a sensed voltage that is proportional to the change in capacitance changes. Therefore, the sensor can determine whether the chamber is, for example, empty, an eighth full, quarter full, half full, full, or any other percent full. Each of these measurements can be made accurately, for example, at least on the order of the accuracy achieved by known gravimetric scales or pressure/ volume measurements. Capacitance sensing, however, is simpler, non-invasive, inexpensive and is operable with continuous, non-batch, type pumping operations.

Generally, the capacitance C between two capacitor plates changes according to the function $C=k\times(S/d)$, wherein k is the dielectric constant, S is the surface area of the individual plates and d is the distance between the plates. The capacitance between the plates changes proportionally according to the function $1/(R\times V)$, wherein R is a known resistance and V is the voltage measured across the capacitor plates.

The dielectric constant k of medical fluid or dialysate is much higher than that of air, which typically fills a pump chamber (such as pump chambers 122, 124, 126 and 128 in FIG. 2, which are part of pumps 22 to 28 in FIG. 1) that is empty or at the end of a pump out stroke. In one embodiment, one of the capacitance plates is moveable with the volume of fluid entering or exiting the chambers 122, yielding the changing distance, Δd, between the plates a factor in determining capacitance. Likewise the surface area, S, of the capacitance plates could be varied. In one preferred embodiment shown figuratively in FIG. 1, the capacitance plates 32, 34, 36 and 38 are set at a fixed distance from one another, e.g., are fixed to the rigid plastic of housing 104 of cassette 100*a*. In that instance, the surface area S is also fixed, leaving the change in the dielectric constant k to account for the change in capacitance as the pump chambers 122 to 128 are filled or emptied of dialysate.

As at least one flexible membrane positioned within chambers 122 to 128 expands and fills with medical fluid, the overall capacitance changes, i.e., increases, creating a high impedance potential across the capacitor plates, one of which is grounded, the other of which is active. That high impedance potential is indicative of an amount of fluid in the chambers 122 to 128. If the sensed potential does not change, or does not change enough, when it is expected to change, the system controller recognizes such lack of change as air that has become trapped in the dialysis fluid and commands appropriate actions.

A capacitance sensing circuit is provided, which amplifies the high impedance signal to produce a low impedance potential. The low impedance is fed back to the capacitance plates 32 to 38 and is used to protect the sensitive generated capacitance signal from being effected by outside electrical influences. The amplified potential is also converted to a digital signal and fed to a the system controller, where it is filtered and or summed. A video monitor having a graphical user interface can then be used to visually provide a volume and/or a flowrate indication to a patient or operator based on the digital signal. Additionally, the controller uses the flowrate and volume information to ensure that Pump Set 2 (pumps 26 and 28) withdraws the appropriate amount of fluid from arterial dialyzer 30, namely, the amount of dialysate pumped from Pump Set 1 (pumps 22 and 24) plus the prescribed amount of UF removed from the patient.

An additional use for capacitance plates or volume measuring devices 32 to 38 is to detect a leak across pump valves V3 and V5, V2 and V4, V15 and V16 and/or V17 and V18. Those valves cycle and alternate during the pump-in and pump-out strokes of pumps 22, 24, 26 and 28, respectively and are opening and closing much more often than other valves in system 10, such as fluid container valves V8 to V14. The pump valves are therefore more susceptible to leakage than are other valves and are relatively critical to the operation of system 10.

The pump valves operate in alternating pairs. For instance, to deliver fluid into pump 22, valve V3 is opened while valve V5 is closed. Conversely, to push fluid from pump 22, valve V3 is closed while valve V5 is opened. If both valves are either opened or closed while a pump stroke takes place, volumetric error occurs. The present invention contemplates a method and apparatus for testing valves V3 and V5, using volume measuring devices 32 to 38.

The valve test in one embodiment utilizes the fact that the pump has flexible fluid membranes that are crimped between a fixed volume pump chamber. When a pump-in stroke takes place, the membranes fill with fluid expanding the membrane. The corresponding pump inlet valve (e.g., valve V3) is then closed, trapping fluid within the flexible pump chamber membranes. A partial pump-out stroke is attempted either via a mechanical piston or positive/negative pneumatic pressure. The pressure exerted is not enough to damage the pump components but is enough so that if either inlet or outlet valves (e.g., V3 and V5) is faulty or leaking, fluid would flow, creating a volume change that would be sensed by volume measuring devices 32 to 36.

If the valves close properly, and assuming dialysate to be incompressible, the small pressure exerted should move no fluid and produce no detectable volume change. If a leak is present, a volume change occurs and is detected, causing the controller to issue an alarm condition or take other appropriate action. The above-described test can be performed at the start of therapy and/or intermittently and periodically throughout therapy, e.g., every five minutes or every one thousand strokes. The test, it should be appreciated, can at least detect which set of pump valves V3 and V5, V2 and V4, V15 and V16 or V17 and V18 is leaking. The test is applicable to all types of medical fluid systems, including blood therapy systems, congestive heart failure systems and peritoneal dialyzer systems.

The chambers 122 to 128 and housing 104 of cassette 100a form a first portion of a clamshell, the second portion being formed by the renal therapy machine. The first and second portions house at least one flexible membrane and the dialysate when dialysate is present. The portions are rigid and form a fixed volume in one preferred embodiment. The portions form the shape of and also house the capacitor plates 32 to 38. That is, one of the capacitor plates is housed in cassette 100a, while the other is housed inside the therapy machine. Alternatively, both plates are housed in the therapy machine, one on either side of the cassette. As stated above, either the cassette or machine (whichever houses the active rather than the ground capacitor plate) houses an additional guard or shield plate that provides noise protection for the high impedance signal transmitted from the active capacitor plate.

As an alternative to the capacitance volume sensor described above, the volume or mass of dialysate fluid flowing through the pumps 22 to 28 can be determined using other methods, such as through an electronic scale or balance. In other alternative embodiments, the mass or volume of dialysate flowed in any of the systems described herein can be sensed using various types of medical grade flowmeters, orifice plates, mass flow meters or other devices employing Boyle's Law. Further, the Fluid Management System ("FMS") technology used in HomeChoice®, as embodied in U.S. Pat. No. 5,431,626 and its associated family of patents, the teachings of each of which are incorporated herein by reference, is also suitable for use in the present invention. A pneumatically controlled system employing this technology is discussed in more detail below. Conductivity sensors may also check for conductive and nonconductive states across the valves, detection of valve leaks is easy with this method.

Still further alternatively, fluid balancing chambers or match flow equalizers may be used, such as those described in U.S. Pat. No. 5,486,286, assigned to the assignee of the present invention, incorporated herein by reference, which are also employed in the System 1000™ produced by the assignee of the present invention. The balancing chambers or flow equalizers are integrated in the cassette in one embodiment and require a separate pump or pressurization source. The chambers or equalizers would manage fresh dialysate on one side of a diaphragm and the spent dialysate on the other side of the diaphragm, matching the volume flow of fresh and spent dialysate. A separate pump is then used to ultrafiltrate fluid from patient 42 accumulated between patient sessions. Peristaltic pumps may also be used to pump dialysate to dialyzers 20 and 30 or to any of the blood filtering devices described herein, pump an equal amount of fluid from such devices, control and pump out a prescribed amount of ultrafiltrate from the patient. One suitable peristaltic pump arrangement is illustrated below in connection with FIG. 12. Systems employing balancing chambers and other volumetric control devices are discussed in more detail below.

Referring still to FIGS. 1 to 3, valves 56 labeled V2, V3, V4 and V5 control which pump is filling and which pump is exhausting dialysate at any given time. Those valves, as well as most if not all the valves of the systems described herein have an electromechanical portion housed inside the blood treatment machine and a fluid flow portion 156, shown in FIG. 2. Dialysate or renal therapy fluid exiting pumps 22 and 24 enters a heater 58. Heater 58 is located alternatively prior to volumetric diaphragm pumps 22 and 24. Heater 58 may be any suitable type of electrical medical fluid heater, such as a plate (electrical resistance) heater, infrared or other radiant heater, convective heater, and any combination thereof. Heater 58 is illustrated as an in-line heater. As seen in FIG. 2, dialysate flows through a flexible membrane heating portion 158 of cassette 100a. The electronics and other hardware associated with heater 58 are located inside the renal failure therapy machine. Heater 58 is located alternatively to batch heat solution bags 14, 16 and 18.

Valve 56 labeled V6 provides a bypass that enables solution at too high or too low a temperature to be diverted to a point upstream of pumps 22 and 24 to prevent solution at too high/low a temperature from reaching the dialyzers 20 and 30 and ultimately blood circuit 50. To that end, temperature sensor 62 labeled T2 senses and provides feedback to the controller of system 10 indicating the temperature of dialysate leaving heater 58. The temperature sensor 62 could be a thermocouple or IR sensor or thermistor, which is housed inside, integral with or directly adjacent to a conductivity sensor probe 63. Conductivity sensing is temperature dependent, so it is logical to locate the two sensors 62 and 63 together or directly adjacent to each other.

A suitable location for the temperature sensor/conducting sensor is, for example, at sensor location T2, T3 which senses the conductivity of the fluid prior to the fluid reaching dialyzers 20 and 30. Conductivity sensor 63 may be used to test the electrolyte composition of the solution. Conductivity sensor or electrolyte sensor 63 is particularly useful when using a dual chamber version of containers 14, 16 and 18, which have multiple solution components that are mixed just prior to use.

A pressure sensor 46 labeled PT4 measures the pressure of the fluid flowing to venous dialyzer 20 and in one embodiment is provided in association with an additional drip chamber 52c that purges air through vent 64c and vent valve 56 labeled V19. Sensor PT4 and chamber 52c are located alternatively prior to volumetric diaphragm pumps 22 and 24.

The dialysate next flows into venous dialyzer 20. The membranes housed inside venous dialyzer are high flux membranes as discussed above. The dialysate flow path connects to the venous 20 and arterial 30 dialyzers via the restriction 40. Restriction 40 provides backpressure that drives a significant amount of the dialysate through the high flux membranes of the venous dialyzer 20 and directly into the blood flowing through the membranes inside venous dialyzer 20. Restriction 40 can be set to backpressure ten to ninety percent of the dialysate entering venous dialyzer 20 into the bloodline. As discussed above, restriction 40 can be set or variable. If a fixed restriction is desired, it is possible to use a single dialyzer rather than the two dialyzers 20 and 30 shown in FIG. 1. A dialyzer having an internal flow restriction suitable for use in place of items 20, 30 and 40 shown in FIG. 1 is described in commonly owned U.S. Pat. No. 5,730,712, entitled "Extracorporeal Blood Treatment Apparatus and Method", incorporated herein by reference. That dialyzer as indicated is limited to having a fixed orifice.

As alluded to above, it is desirable for a number of reasons that restriction 40 be a variable restriction. For one reason, different patients may respond to a therapy that is more convective or more diffusive. From a cost and manufacturing standpoint, it is desirable to have a unit that can be adjusted for any patient rather than "custom" units fitted with the necessary flow restriction. Second, it is very possible that the patient and doctor will not know initially what the optimal percentage convective clearance versus diffusive clearance breakdown is, requiring some period of experimentation and optimization. Moreover, it may be desirable for a patient to perform a first treatment using a first percentage convective clearance versus diffusive clearance and later in the week, the next day or later in the same day perform a second treatment using a different percentage convective clearance versus diffusive clearance.

Still further, system 10 has the capability of varying the percentage convective clearance versus diffusive clearance over a single therapy session or treatment, for example in step increments or continuously. Such changes can be made as gradually or quickly as desired and span as great a range as desired, e.g., starting with 90 percent convective and ending with 90 percent diffusive. It may be determined that it is desirable to clear molecules of a particular size or range of sizes or molecules of a particular type during a certain point in the therapy, e.g., at the beginning or end. Variable restriction 40 also makes it possible to repeat certain settings or patterns of settings during a single treatment.

The present invention contemplates at least three levels of variability for restriction 40. The first level can be referred to as "semi-fixed". Here, the restriction could use a fixed orifice restriction plate, but wherein restriction 40 is configured and arranged so that the plate can be swapped out for a plate having a different sized orifice. Such swapping out would occur, however, between therapies. A second level of variability can be referred to as "manual-on-the-fly". Restriction 40 in this instance could be a backpressure regulator or variable orifice valve with a manual adjustment that enables the patient or operator to adjust the backpressure and thus the convective versus diffusive clearance percentage. The manual adjustment could be made during a current therapy or between therapies. The third level of variability is automatic, which could be effected for example via a pneumatically operated backpressure regulator or variable orifice valve. Such pneumatically operated device receives a pneumatic signal at a controlled pressure, which sets the backpressure accordingly. The controller could be configured to output for example an analog signal, e.g., a 0-5 VDC or 4-20 mA signal, which is converted via an I/P converter to a pressure signal at a corresponding pressure. The automatic adjustment could be made during a current therapy or between therapies.

Referring still to FIGS. 1 to 3, Pump Set 2 including pumps 26 and 28 resides on the exit end of arterial dialyzer 30. Each of the various embodiments described above for Pump Set 1, including the pump configuration, is applicable for Pump Set 2. Pump Set 2 is normally configured to pump at the rate of the fresh dialysate input of Pump Set 1 plus an additional amount to remove excess fluid that has accumulated in the patient's blood and tissues between treatment sessions.

The waste dialysate and a volumetric equivalent to the patient's fluid gained in the interdialytic period flows from arterial dialyzer 30, through valves 56 labeled V16 and V18, through pumps 26 and 28, through valves 56 labeled V15 and V17, through a blood leak detector 66 and to one of the drain bags 12 to 16, which as discussed above are opened selectively via valves 56 labeled V9 to V14. Valves 56, detector 66 and fluid contacting portions of pumps 26 and 28 are each in one embodiment located in the housing portion 104 of cassette 100a. The waste and a volumetric equivalent to the patient's UF may alternatively be routed after BLD 66 to a long tube placed in an acceptable drain. This alternative will not work with balance scale systems.

Blood leak detector 66 includes in one embodiment a light source and a photo sensor. Blood components that are not meant to be filtered through dialyzers 20 and 30 lower the light reaching the photo sensor of detector 66 if such components do travel through the membrane walls of the dialyzers into the therapy solution flow path. The controller of system 10 continuously monitors the photo sensor. Detection of a blood leak triggers an audio and/or visual alarm, stops blood pump 48 and closes venous line valve V1. A blood sensor, such as detector 66, is alternatively or additionally placed in the venous line running from venous dialyzer 30 to pumps 26 and 28.

In special modes, infusion pumps 22 and 24 of Pump Set 1 can infuse more solution than is removed to drain by pumps 26 and 28 of Pump Set 2. For example, during priming, during blood rinseback or for bolus infusion, infusion pumps 22 and 24 can infuse a volume that is greater than the volume removed by pumps 26 and 28. The special modes enable the system to fill with fluid, enable blood in line 50 at the end of therapy to rinseback to the patient 42 or for the patient 42 to receive a bolus of solution via the venous dialyzer into the post dialyzer portion of circuit 50 and through venous access 44b to patient 42.

During priming, the arterial and venous needles 44a and 44b are connected together as seen in FIG. 2. The pumps of Pump Sets 1 and 2 are run until air is purged from the system, so that only (or substantially only) dialysate flows throughout the dialysate flow path 60. When blood pump 48 begins pumping, dialysate and/or saline is backfiltered from venous dialyzer 20 into blood line 50, priming the remainder of the extracorporeal circuit 50. An alternative or additional form of priming is to connect a bag of saline at arterial access 44a.

In one embodiment, blood is returned to the body by reversing the flow direction of blood pump 48, which would require an additional air/blood detector and clamp, such as ABD 54 and clamp V1 placed in line 44a, between pump 48 and patient 42. Blood pump 48 would run in reverse until the additional air blood sensor detected an absence of blood in line 44a. Pump 48 would be reversed again to flow fluid in the normal direction, which would return filtered dialysate and blood to patient 42 until the absence of blood is sensed in the venous line 44b. Alternatively, this same method of blood rinseback may be employed but the air blood sensor would only be used to confirm the absence of blood, but the rinse controlled by pre-set dialysate and/or saline volume.

Alternative Source—Fluid Preparation Module

Figure 4:
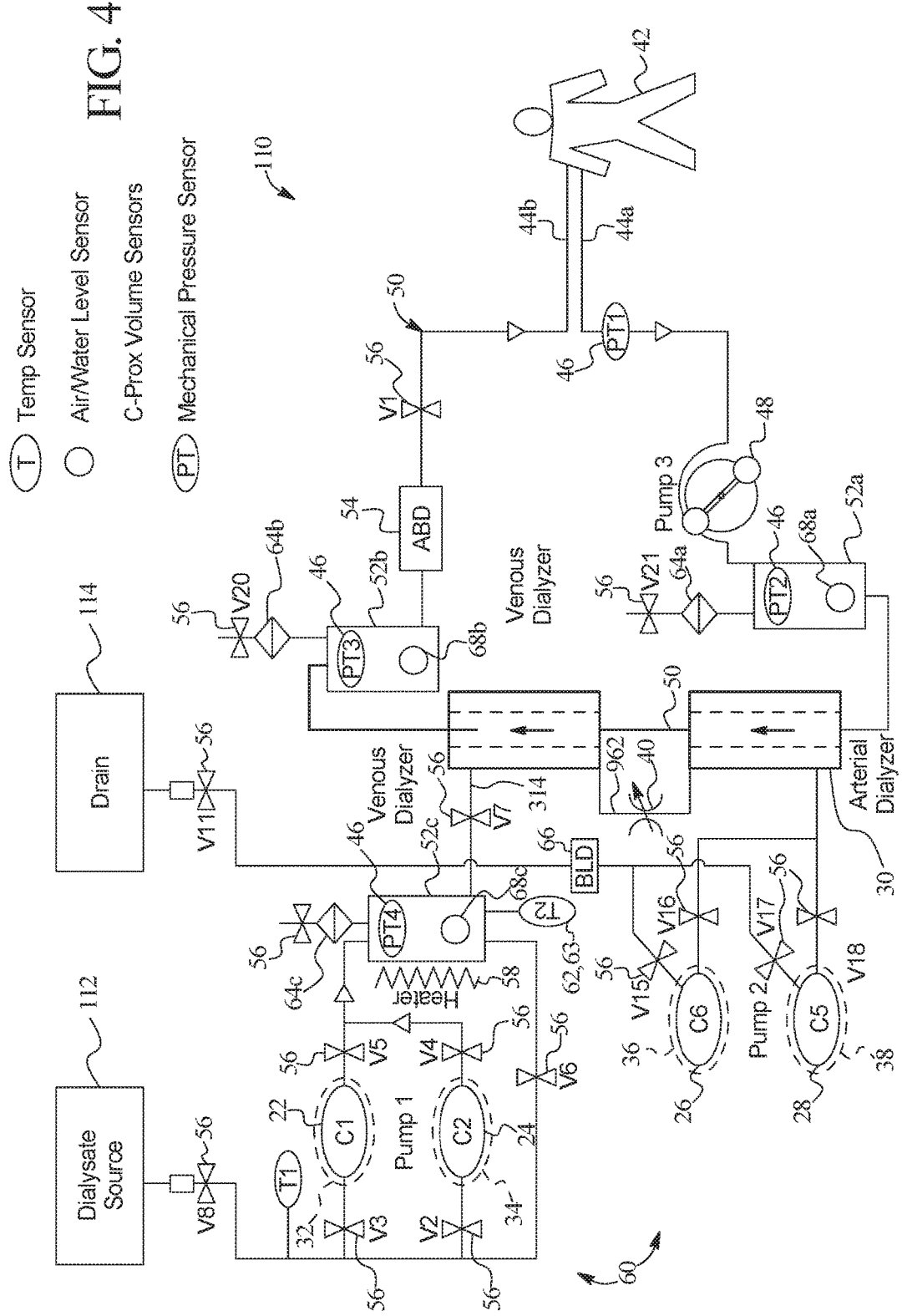
FIG. 4 is a schematic illustration of a renal failure therapy system that operates with a dialysate fluid generation unit.

Referring now to FIG. 4, an alternative system 110 is provided that operates in a very similar manner to the system 10 described above. Indeed, each of the like reference numerals shown in FIGS. 1 and 4 have the same functionality and the same alternatives as described previously. System 110 performs convective and diffusive clearance as described above and removes the amount of fluid gained by patient 42 between therapy sessions.

System 110 differs from system 10 in that system 110 does not use solution bags 14 to 18 and drain bag 12, instead, system 110 operates with and connects to a separate fluid preparation module 112. System 110 is advantageous because patient 42 is not required to store, connect to, disconnect from and discard multiple solution bags as described above. As seen by comparing systems 10 and 110, system 110 eliminates multiple valves 56 (V9, V10 and V12 to V14) by using an on-line dialysate generation source 112.

One suitable fluid preparation module 112 suitable for home use is commercially available from PrisMedical, however, other systems having a water purification pack and electrolyte cartridge to prepare the dialysate could be used. System 110 alternatively uses a large, e.g., about 120 liters, fill bag or fill container (not illustrated), which receives dialysate or therapy fluid from the preparation module 112. System 110 is also compatible with an in-center environment, wherein a single-patient or central fluid preparation module 112 supplies a single or multiple systems 110. The single patient or central proportioning module could prepare dialysate or substitution fluid using a proportioning system. For an in-center use, it is contemplated not to use cassette 100a but instead provide a machine that can be sterilized and re-used. In any of the above-described embodiments for system 110, the system pumps waste dialysate and UF to a waste dialysate bag, waste container, drain or waste area 114.

Addition of Regeneration Loop

Figure 5:
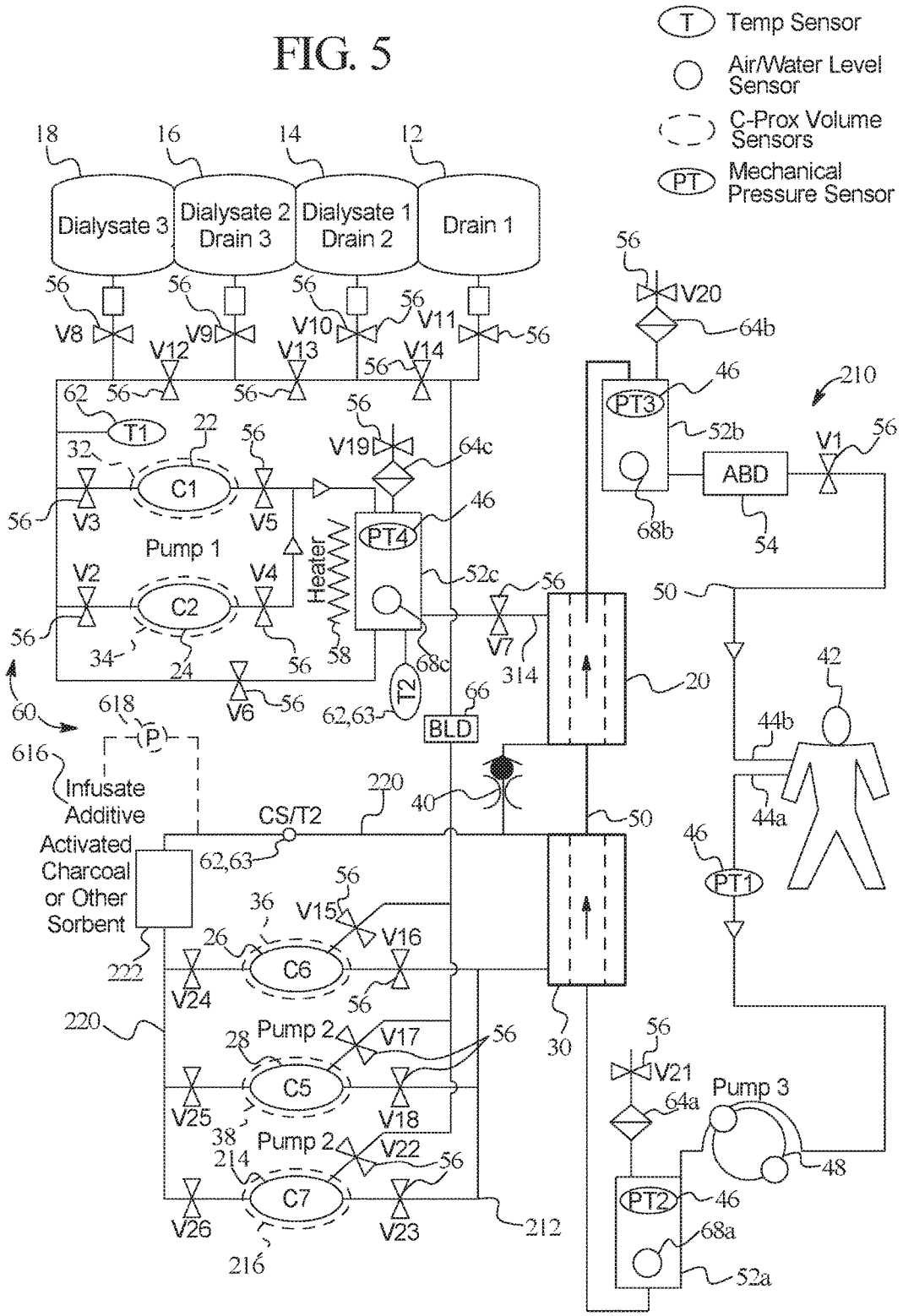
FIG. 5 is a schematic illustration of a renal failure blood treatment therapy system having a therapy fluid recirculation loop.

Referring now to FIG. 5, an alternative system 210 is provided that adds a regeneration loop 212 to the dialysate flow path. As with FIG. 4, each of the like reference numerals shown in FIGS. 1, 4 and 5 have the same functionality and the same alternatives as described previously. System 210 also performs convective and diffusive clearances as described above and removes an amount of fluid or ultrafiltrate gained by patient 42 between therapy sessions.

Regeneration loop 212 includes an additional pump 214, which operates with an associated volumetric measuring device 216. Any of the embodiments described above for pumping, measuring flow and controlling flow may be employed for pump 214 and measuring device 216. Additional inlet and outlet valves 56, labeled V22, V23 and V26 are provided to allow or disallow flow of spent dialysate/UF from arterial dialyzer 30 to be pumped to pump 214. As illustrated, pump 214 can pump to the recirculation sorbent cartridge 222 or to drain. Additional outlet valves 56, labeled V24 and V25, are connected fluidly to UF pumps 26 and 28, so that those pumps can pump selectively to drain or to the recirculation sorbent cartridge 222. In short, any combination of pumps 26 and 28 can be used repeatedly or at different times during therapy for recirculation or ultrafiltration.

As illustrated, pump 214 is configured to pump spent dialysate/UF back to the inlet of arterial dialyzer 30 via line 220. Line 220 alternatively runs to the inlet of venous dialyzer 20, wherein the regenerated fluid is reintroduced into that dialyzer. Moreover, regenerated fluid could be pumped to both of the inlets of venous dialyzer 20 and arterial dialyzer 30. Still further, it is possible to regenerate fluid exiting venous dialyzer 20 alternatively or additionally to the regeneration of fluid exiting arterial dialyzer 30.

In system 210, the total amount pumped through UF pumps changes due to the additional recirculation pump 214. In the example given above, pumps 26 and 28 of Pump Set 2 were said to remove eighteen liters of dialysate added over the course of the therapy (wherein twelve liters was used for convective clearance, while six liters of dialysate was used for diffusive clearance) plus any fluid ultrafiltered from the patient.

Applying the eighteen liters used in the above Example to system 210, and assuming twelve liters is used to produce convective clearance, the remaining six liters plus the volume of fluid that is recirculated through recirculation loop 212 is then used to produce diffusive clearance. If pumps 26, 28 and 214 are configured so that one-third of all fluid exiting arterial dialyzer 30 is recirculated, then 225 ml/min is pulled from arterial dialyzer 30, 75 ml is passed through recirculation loop 212 and 150 ml is discharged to the drain bags 12, 14 and 16. The diffusive clearance is calculated to be the six liters of single pass dialysate plus 75 ml/min of recirculation loop 212 dialysate for 120 minutes, or six liters plus nine liters, totaling fifteen liters of diffusive clearance. If pumps 26, 28 and 214 are each operated at 100 ml/min, one-half of all fluid exiting arterial dialyzer 30 is recirculated through recirculation loop 212 and the diffusive clearance increases to six liters plus 150 ml/min for 120 minutes or six liters plus eighteen liters, totaling twenty-four liters of total diffusive clearance.

The trade-off for the increased clearance is that a sorbent cartridge 222 is required in recirculation loop 212 to clean or regenerate the spent dialysate/UF pulled exiting arterial dialyzer 30. Depending on quantity and quality needed for the regenerated fluid, cartridge 222 may be as simple as a carbon cartridge but is alternatively a multilayer cartridge with Urease (similar to the cartridges described in U.S. Pat. Nos. 3,669,880 and 3,669,878, the teachings of which are incorporated herein by reference). Other suitable cartridges and materials therefore are discussed in commonly owned U.S. patent application Ser. No. 10/624,150, entitled, "Systems And Methods For Performing Peritoneal Dialysis" and commonly owned U.S. Pat. No. 7,208,092, entitled, "Systems And Methods For Peritoneal Dialysis", the teachings of each of which are incorporated herein by reference. Depending on the type of sorbent used in cartridge 222, system 210 as well as any other system described herein that uses sorbents may require a sterile infusate additive 616 on line 220 to replace electrolytes lost in the sorbent cartridge and a conductivity temperature sensor 62, 63 to measure the electrolytes independently of the infusion.

In general, the cleaning cartridges remove waste products from the spent fluid and improve the efficiency of same for causing diffusive transport of toxins. Sorbent cartridge or cleaning cartridge 22, can employ one or more different types of cleaners or exchangers, such as an activated charcoal filter, a sorbent exchange, a chemical cleaner, a chemical exchange, a biological cleanser, a binding adsorption agent, an enzomatic reaction agent, a mechanical cleaner and any combination thereof.

Cassette-Based Hemofiltration System

Figure 6:
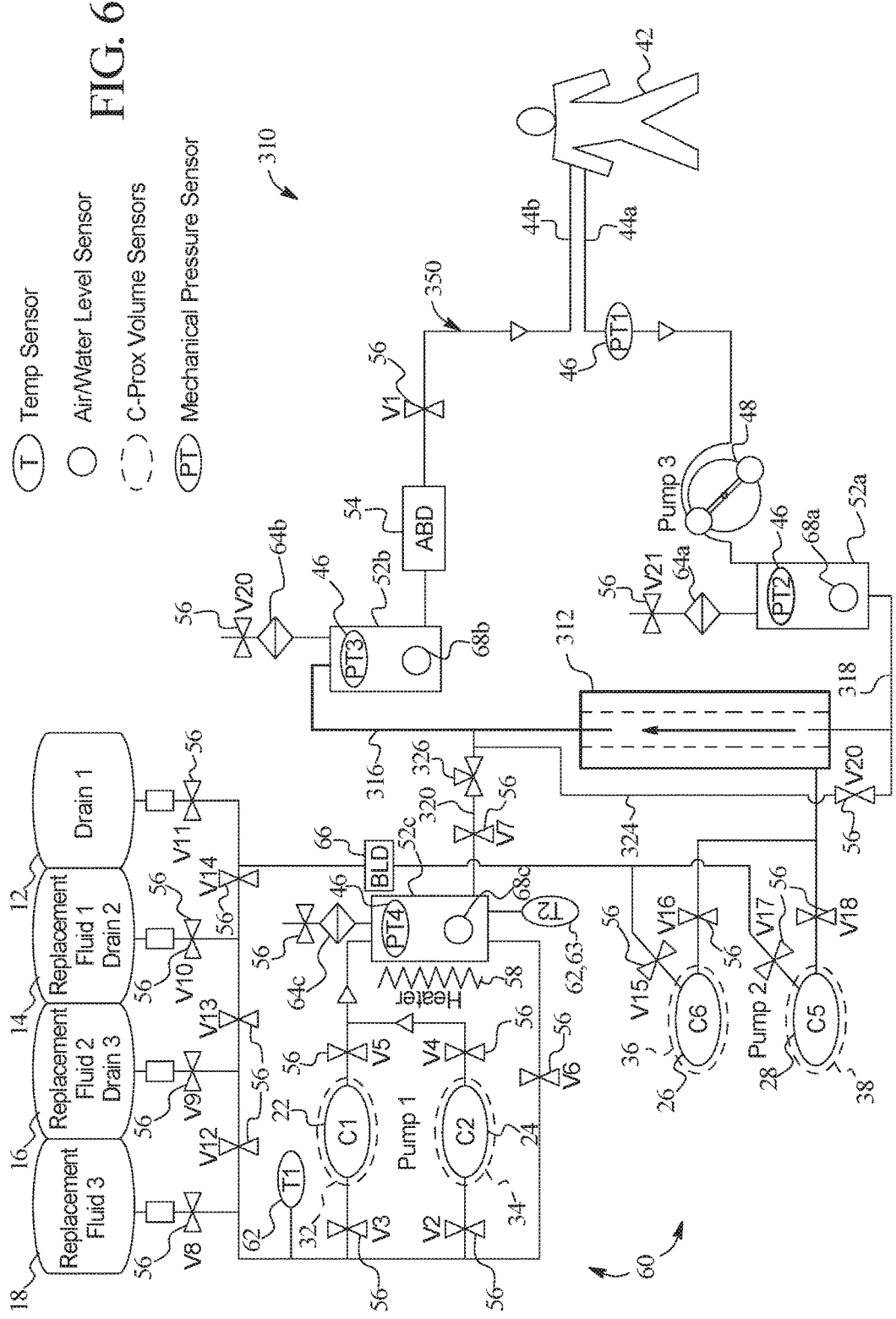
FIG. 6 is a schematic illustration of one embodiment of a home use hemofiltration system of the present invention.
Figure 7:
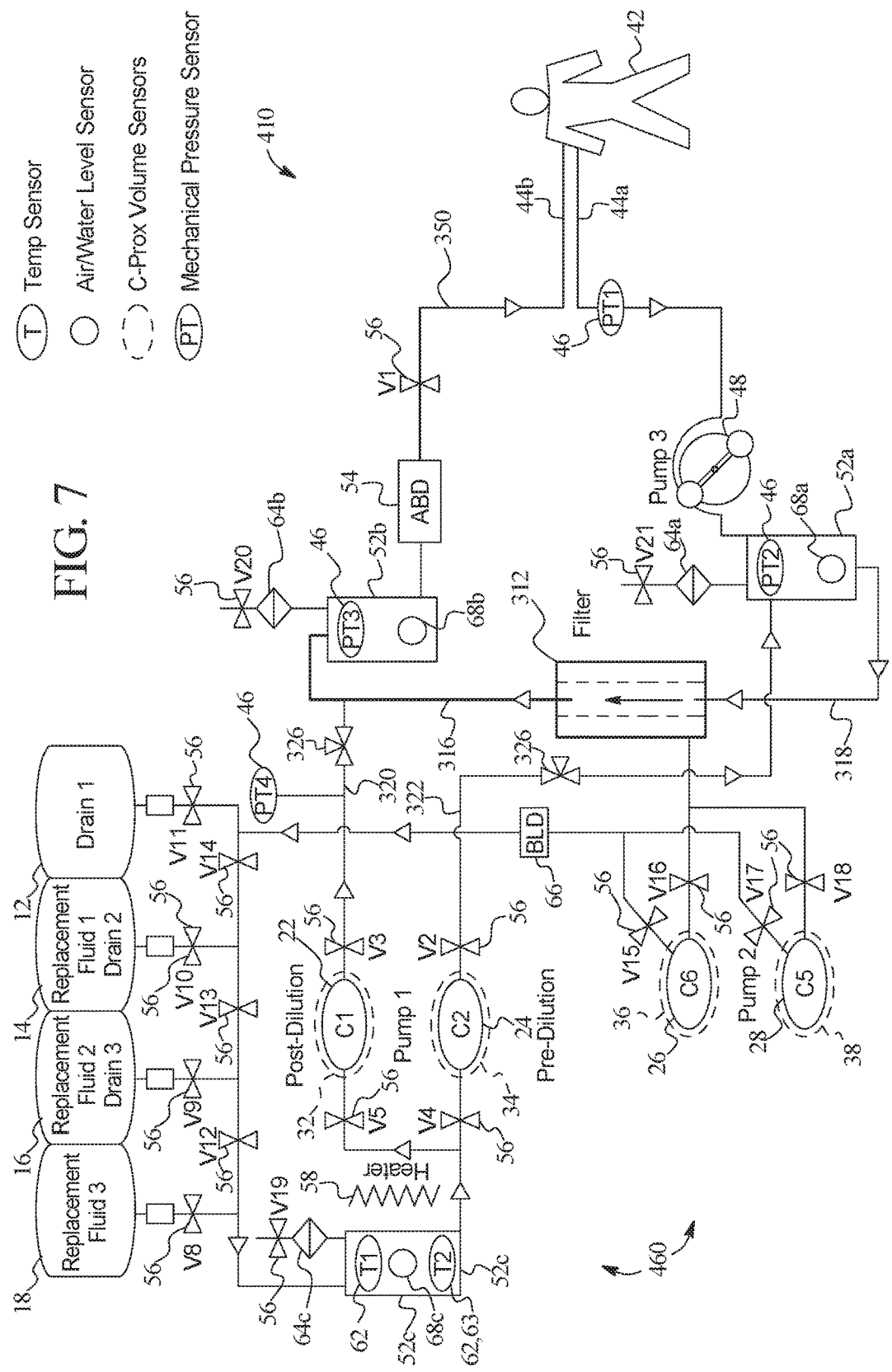
FIG. 7 is a schematic view of another embodiment of a home use hemofiltration system of the present invention.

Referring now to FIGS. 6 and 7, systems 310 and 410, respectively, illustrate that the cassette-based home system is configurable alternatively to perform pure hemofiltration. The primary differences between systems 310 and 410 versus systems 10, 110 and 210 described above are that the pure hemofiltration systems do not use the venous dialyzer 20 and the restriction 40, which may simply be removed from or bypassed in cassette 100a to form hemofiltration system 310 or 410. Arterial dialyzer 30 in FIG. 1 then operates as hemofilter 312 in system 310 or 410. Arterial dialyzer 30/hemofilter 312 is therefore chosen to be able to perform both roles.

The remainder of system 310 is configured by disconnecting the line 314 (shown in FIG. 1) from venous dialyzer 20 (FIG. 1) and reconnecting the line to postdilution line 316 in FIG. 6. Such disconnection and connection and can occur either in housing 104 of cassette 100a or via tubing connected to cassette 100a. The present invention accordingly contemplates expressly the provision of a cassette that can either be factory set or be set in the field or at home by the patient for hemofiltration or for the backfiltered hemodiafiltration ("HDF") therapy described above.

A check valve 326 is placed in line 314 to prevent blood from backing up into pumps 22 and 24. A similar check valve 326 can be used in an analogous location in any hemofiltration or HDF embodiment described herein, e.g., FIGS. 6 to 8 and 11. Optional shunt line 324 and valve 56, labeled V20, may be used so that predilution and postdilution HF can be performed selectively individually or simultaneously with system 310 and other systems shown below.

System 310 as illustrated is a postdilution hemofiltration device, wherein fluid from infusion pumps 22 and 24 is injected directly into the postdilution bloodline 316, which is located downstream of hemofilter 312. In an alternative embodiment, fluid from infusion pumps 22 and 24 is injected directly into the predilution bloodline 318, which is located upstream of hemofilter 312. In such a case, the fluid in one preferred embodiment is injected at or upstream of drip chamber 52a to prevent air from entering filter 312. Predilution and postdilution both have particular advantages over one another.

Postdilution provides better clearance per liter of substitution solution than does the predilution clearance mode. Postdilution clearance per liter of substitution fluid can, for example, be twice as effective as predilution clearance. Postdilution blood flow rate limitations, however, restrict the total amount of substitution fluid due to the risk of hemoconcentration. Predilution allows for higher clearance rates because the volume of substitution fluid is not limited by hemoconcentration. Therefore, the overall clearance over a given time can be, albeit less efficiently, greater using predilution therapy than for postdilution therapy.

FIG. 7 illustrates another alternative embodiment for a hemofiltration system of the present invention. System 410 of FIG. 7 illustrates that a first dialysate line 320 extends from the output of postdilution infusion pump 22 and feeds directly into postdilution line 316, which exits hemofilter 312.

A second line 322 extends from the output of predilution pump 24 to the drip chamber 52a placed just in front of predilution line 318, which extends to the input of hemofilter 312. Check valves 326 are placed in both lines 320 and 322 to prevent blood from backing up into pumps 22 and 24, respectively. The embodiments discussed in FIGS. 6 and 7 have many of the same components described above in connection with FIGS. 1, 4 and 5. Those components are marked with the same element numbers and include each of the characteristics and alternatives described above for such numbers.

The dialysate flow path 460 is configured somewhat differently than dialysate or therapy solution flow path 60 described above. As illustrated, heater 58 is moved in front of Pump Set 1, namely, postdilution pump 22 and predilution pump 24. Drip chamber 52c likewise has been moved to be in front of infusion pumps 22 and 24 of Pump Set 1. Drip chamber 52c is provided with two temperature sensors, labeled T1 and T2, as illustrated. Drip chamber 52c also operates with vent 64c as described above. Heated fluid leaving heater 58 enters postdilution and predilution pumps 22 and 24.

Fluid exiting postdilution pump 22 flows via line 320 to postdilution line 316, where that fluid enters alternative blood circuit 350 to perform convective clearance. Fluid pumped from predilution pump 24 flows via predilution line 322 to drip chamber 52a, wherein the dialysate or therapy fluid is mixed in drip chamber 52a with blood pumped via pump 48. The blood and dialysate or therapy fluid thereafter flow to hemofilter 312.

Assuming pumps 22 and 24 pump about the same amount of fluid over a given period of time, fifty percent of the dialysate or therapy fluid is used for postdilution clearance, while the other fifty percent, approximately, is used for predilution clearance. It is important to note that this ratio can be varied by changing the frequency of pumps 22 and 24. The postdilution dialysate enters the patient 42 before flowing through hemofilter 312. The predilution dialysate or therapy fluid on the other hand flows through hemofilter 312 before reaching patient 42.

Any of the embodiments described herein for providing dialysate, either prepackaged or prepared on-line, is applicable to system 310 and 410 of FIGS. 6 and 7, as well as each of the other embodiments described herein. Moreover, the cassette described above in connection with FIGS. 2 and 3 as well as each of the embodiments shown below for configuring the therapy machine and supply bags is additionally operable with the hemofiltration embodiments of FIGS. 6 and 7. The hemofiltration systems 310 and 410 are cassette-based in one preferred embodiments and are readily applicable to home use.

Cassette-Based Hemodiafiltration System

Figure 8:
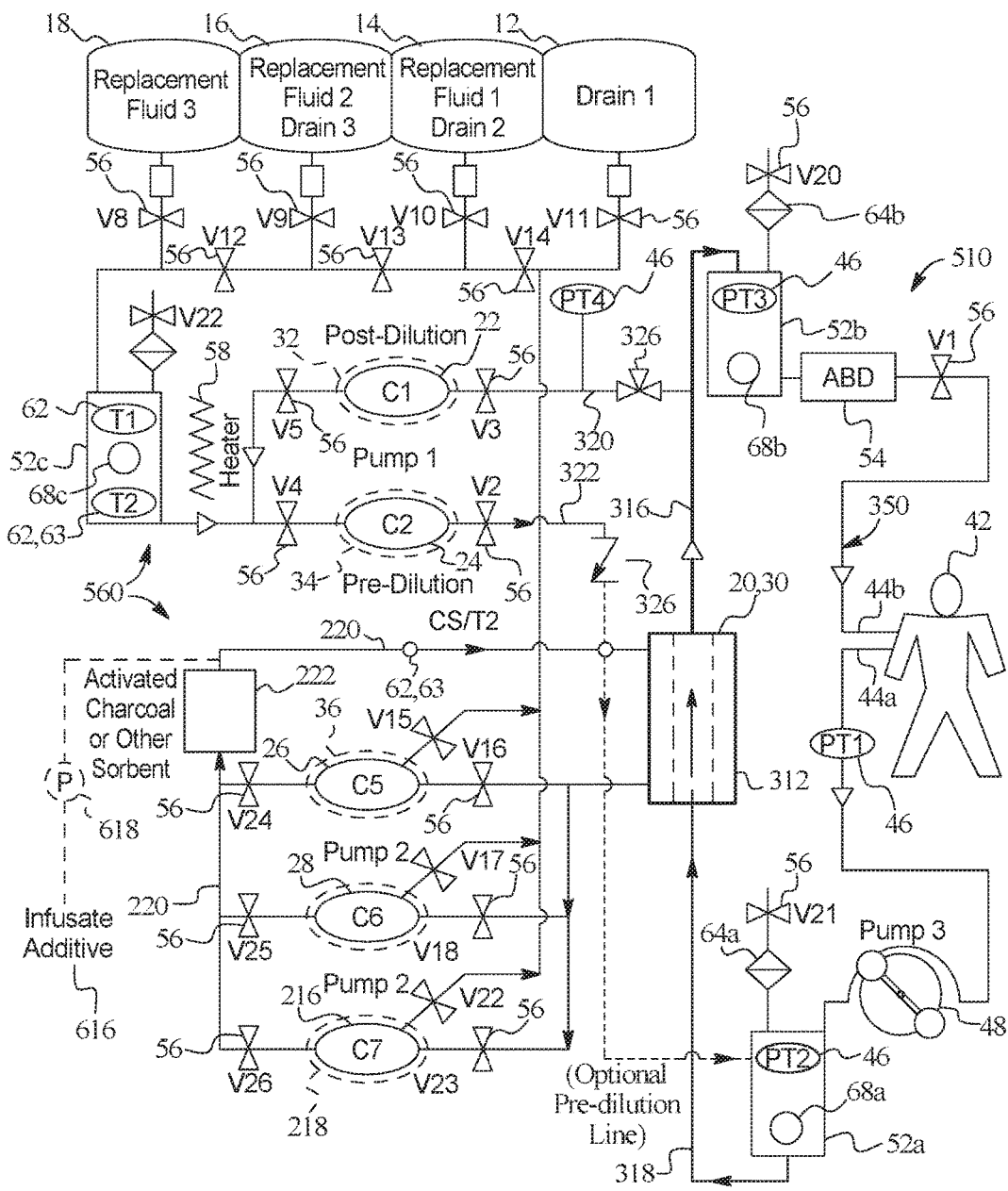
FIG. 8 is a schematic view of one embodiment of a home use hemodiafiltration system of the present invention.

Referring now to FIG. 8, one embodiment of a home-based hemodiafiltration system 510 is illustrated. Systems 10, 110 and 210 described above provide a type of hemodiafiltration therapy having convective and diffusive transport modes caused by restriction 40 placed between dialyzer portions 20 and 30. System 510 on the other hand provides a hemodiafiltration system 510 via a different flow configuration. Nevertheless, many of the flow components of hemodiafiltration system 510, as before, are provided on a disposable cassette, which is inserted for a single therapy into a hemodiafiltration machine.

The dialysate or therapy fluid flow path 560 of hemodiafiltration unit 510 is a hybrid of the flow path 460 of system 410 described in connection with FIG. 7 and the system 210 described in connection with FIG. 5. Like FIG. 7, a postdilution infusion pump 22 pumps dialysate directly into postdilution blood line 316 via line 320, while predilution infusion pump 24 pumps dialysate or therapy fluid via line 322 into filter 20, 30. In alternative embodiments, hemodiafiltration system 510 infuses dialysate only into predilution line 318 or postdilution line 316.

Like FIG. 5, system 510 is also illustrated as having the additional ultrafiltrate pump 216 that pulls a portion of the spent dialysate from dialyzer 20, 30 and pumps that portion through recirculation line 220 and activated charcoal or other absorbent cartridge 222. As described above, cartridge 222 regenerates some of the spent dialysate and ultrafiltrate from dialyzer 20, 30, which ultimately results in the use of less fresh fluid from containers 14 to 18 per liter of diffusive clearance. Depending on the type of sorbent used in cartridge 222, system 210 as well as any other system described herein that uses sorbents may require a sterile infusate additive 616 on line 220 to replace electrolytes lost in the sorbent cartridge and a conductivity temperature sensor 62, 63 to measure the electrolytes independently of the infusion. It should appreciated, however, that hemodiafiltration system 510 does not require a regeneration loop 220 or cartridge 224.

Hemodiafiltration system 510 operates in a similar manner to the system 10, 110 and 210 described above. That is, both systems provide convective and diffusive clearance modes. In system 510, the convective clearance occurs because lines 320 and 322 from the infusion pumps convey dialysate or therapy fluid directly into the blood circuit 350. Check valves 326 are placed in both lines 320 and 322 to prevent blood from backing up into pumps 22 and 24, respectively. Diffusive clearance also occurs because dialysate is additionally moved across the membranes inside dialyzer 20, 30.

At least a portion of many of the sensors, the pump chambers, the fluid heating pathway, the fluid flow portions of valves 56 as well as many other components of system 510 are provided in whole or in part on a cassette, such as cassette 100a. Cassette 100a is then loaded into a hemodiafiltration machine for a single use and then discarded. System 510 is thereby well suited for home use.

Recirculation

Figure 9:
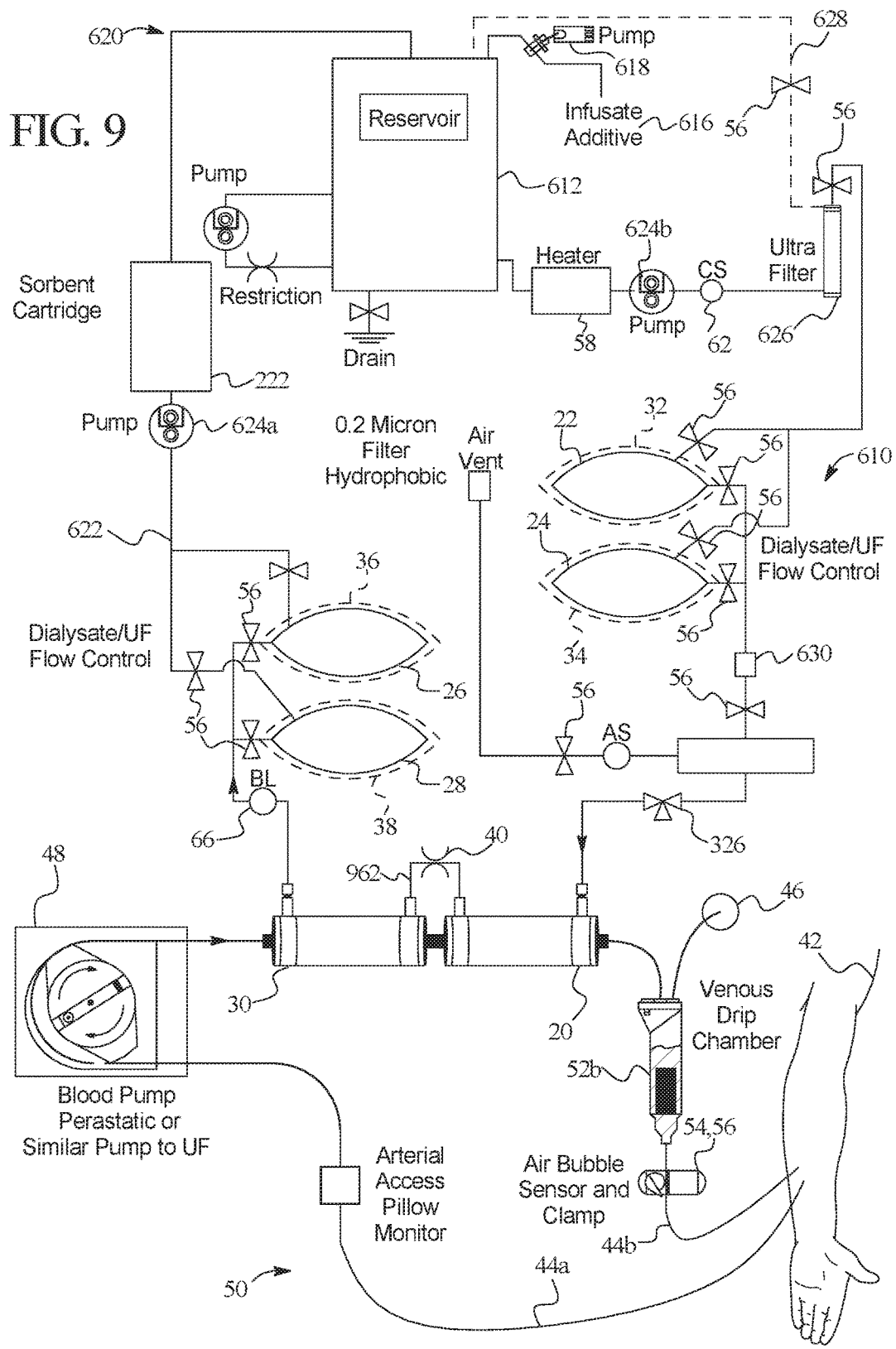
FIGS. 9 to 11 show various embodiments of a home use blood treatment therapy that employs a regeneration unit that regenerates and reuses spent dialysis fluid and fluid ultrafiltered from the patient.
Figure 10:
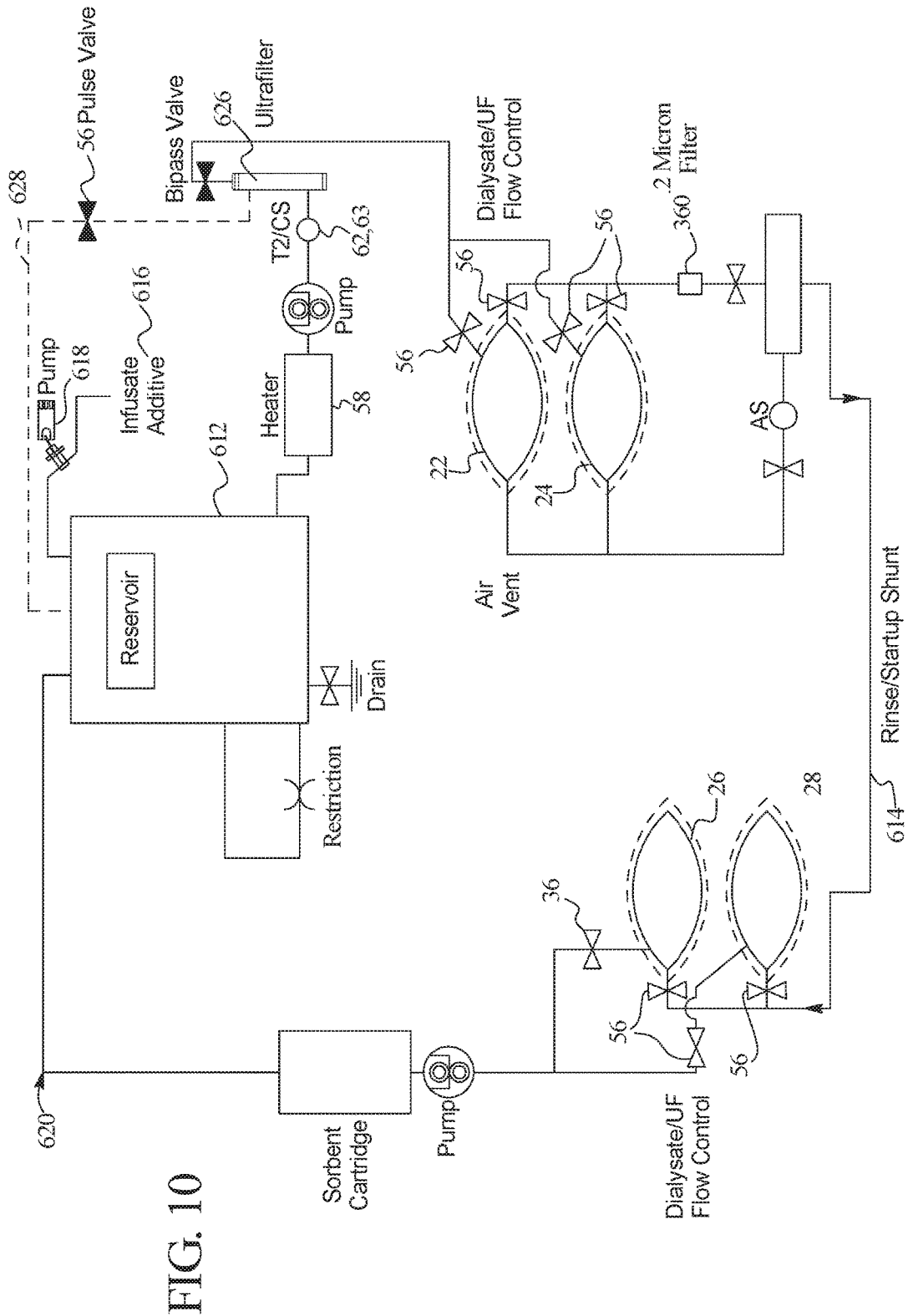
Figure 11:
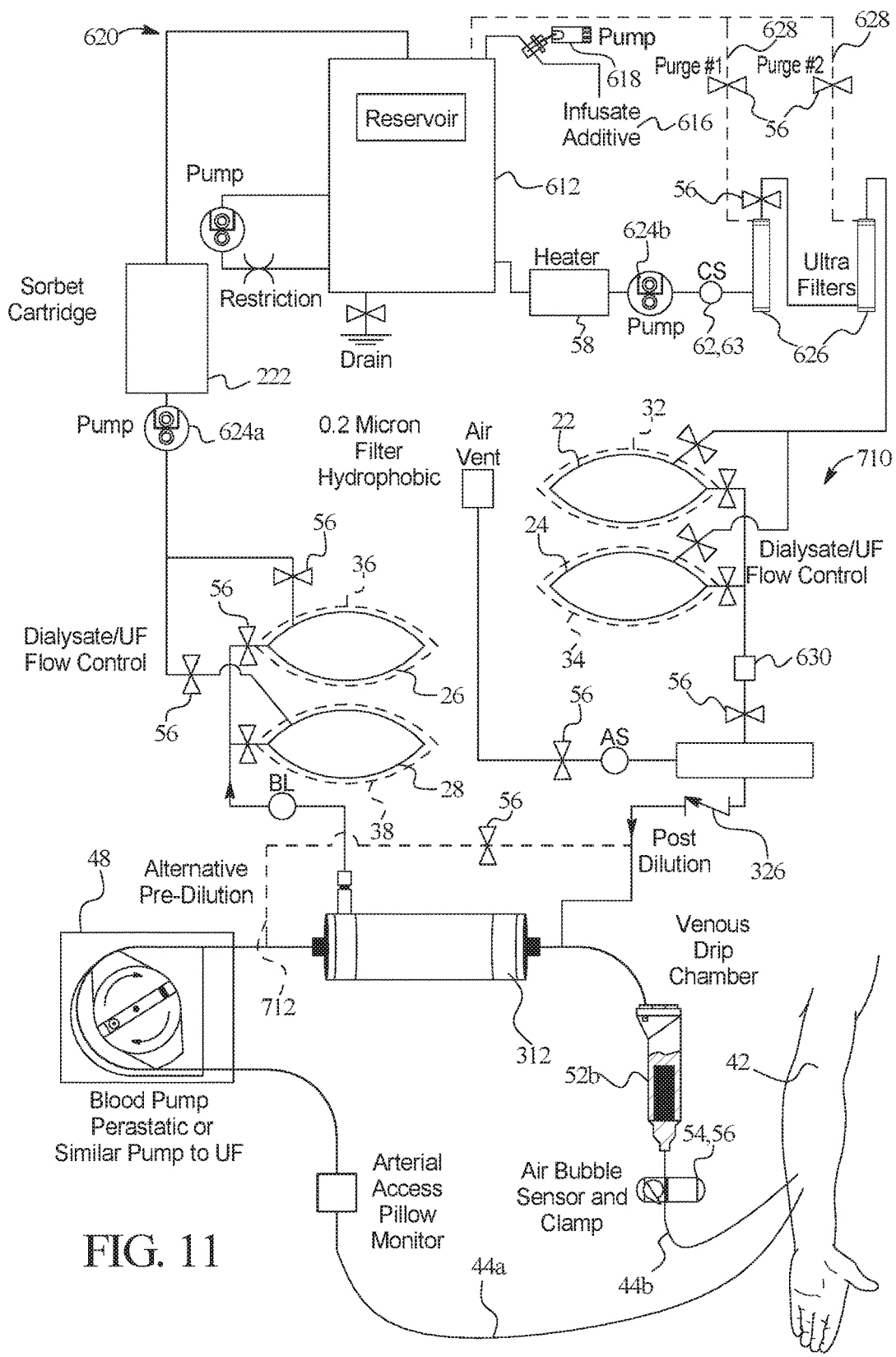

The systems described previously require a fluid source, such as, sterile dialysate from bags, e.g., as in FIG. 1, or from a fluid generation pack, e.g., as seen in FIG. 2. FIGS. 9 to 11 describe systems that are applicable to any of the therapies described herein (e.g., using convection and/or diffusive clearance modes). The systems of FIGS. 9 to 11, however, use a recirculating sorbent system with various filters to produce an ultrapure dialysate source.

Referring now to FIGS. 9 to 11, various sorbent-based regeneration systems are illustrated. FIG. 9 shows a sorbent-based regeneration system 610 that performs the backfiltered convection and diffusion described in systems 10, 110 and 210 above. FIG. 10 shows the system (610 of FIG. 9 or 710 of FIG. 11) being shunted at start-up for rinsing and priming System 710 of FIG. 11 is a hemofiltration system using sorbent-based regeneration, which is applicable to pre- and postdilution type HF systems as well as the HDF system 510 described in FIG. 8.

In the system 610 of FIG. 9, patient 42 uses an initial five liter bag of sterile dialysate, which is installed in a rigid container to form a reservoir 612. Alternatively, five liters of water and concentrate powders or liquids are mixed inside reservoir 612 to form an initial therapy solution.

FIG. 10 illustrates that a shunt 614 is placed across dialyzers 20 and 30 at the beginning of treatment. A sorbent cartridge 222 is placed in the dialysate flow path 620 downstream of shunt 614. Cartridge 222 is, for example, any of the types of sorbent systems described above in connection with system 210 of FIG. 5. An infusate 616 including, e.g., calcium, magnesium and/or potassium is pumped via infusate pump 618 into reservoir 612 as necessary to replenish ions that are removed via the sorbent cartridge 222.

Heater 58 heats the solution leaving reservoir 612. After the solution is heated, system 610 prompts the user or patient 42 to install a disposable, sterile cassette, such as cassette 100a described above. At least a portion of the air bubble detectors 54, heating elements of heater 58, pressure sensors 46, temperature sensors 62, etc., are integrated into the cassette in both the dialysate and extracorporeal blood flow paths as necessary to allow for a safe treatment for the patient and reliable operation of system 610. The blood circuit 50 is primed with a saline bag connected to the arterial bloodline or via backfiltering dialysate or saline through venous dialyzer 20.

The patient is connected to the arterial and venous access lines 44a and 44b respectively, and treatment begins. For short therapies, the dialysate flow can be relatively high, such as three hundred ml/min for three hours or one hundred ml/min for up to eight hours. Dialysate pumps 22 and 24 and UF pumps 26 and 28 control flow to and from dialyzers 20 and 30. By increasing the pumping rate of pumps 26 and 28 that remove the effluent dialysate from arterial dialyzer 30, the fluid accumulated in the patient in the interdialytic period is removed. The fluid flow portions of dialysate/UF pumps 22 to 28 are integrated into the cassette along with the extracorporeal circuit in one embodiment. Alternatively, those components are maintained separately from the cassette and are integrated into the machine.

FIG. 9 shows two volumetric devices 22 and 24 for dialysate flow and two for 26 and 28. Alternatively, one pump is employed on the input and one on the output, however, such configuration could create pulsatile flow, which is less desirable.

Fresh dialysate flows initially to venous hemodialyzer 20. A restriction 40 placed between dialyzers 20 and 30 builds backpressure in dialyzer 20, so that a relatively large amount of the dialysate is backfiltered into blood circuit 50, with the remaining portion of the dialysate flowing to arterial dialyzer 30. System 610 in that manner provides diffusive as well as convective clearance as has been described herein.

Used dialysate and UF pulled from arterial dialyzer 30 is then circulated through the sorbent cartridge 222. Cartridge 222 removes waste products from the spent dialysate/UF fluid. The cleaned fluid is pumped to reservoir/bag 612, where infusate 616 is added to replace the electrolytes removed by the sorbent cartridge 222.

The majority of dialysate flow path 620 is located within the cassette. The cassette is single use in one embodiment but is alternatively reusable with suitable disinfection and/or sterilization. Most all components of the extracorporeal circuit 50 may be integrated into the cassette except, e.g., the tubing extending to and from the patient. The extracorporeal circuit 50 of system 610 is similar to the circuit 50 described above in systems 10, 110 and 210.

The dialysate/infusate is heated as it exits reservoir 612 and flows past a temperature/conductivity sensor 62. If the solution is too hot, too cold or otherwise outside of a defined physiological range, a bypass valve 56 provided with ultrafilter 626 is closed and a purge valve 56 in bypass line 628 is opened to bypass dialyzers 20 and 30. During that bypass, both the infusate and UF pumps 22 to 28 may be stopped. To facilitate the bypass and a smooth, steady flow of fluid to/from reservoir 612, a second circulation pump 624b may be employed.

When the solution is within the defined temperature/physiological range, the solution passes through reusable ultrafilter 626, which employs a molecular weight cutoff that filters bacteria. Ultrafilter 626 also filters and absorbs endotoxin. The filtration of system 610, including ultrafilter 626, is intended to provide dialysate in as pure a form as possible. Ultrafilter 626 may also be a microfilter, if the microfilter can remove acceptable amounts of bacteria and pyrogens.

From ultrafilter 626 the dialysate or therapy solution is pumped to infusion pumps 22 and 24. Flow measuring devices 32 to 38 monitor the volume of the fluid pumped by pumps 22 to 28. Pumps 22 to 28 are configured as described above to leak to an external point. Any leaks are diverted into a moisture sensor built into the cassette and/or cassette/machine interface, so that corrective action is taken upon detection of a leak.

Fluid flows from infusion pumps 22 and 24 through a small 0.2 micron microfilter 630 in one embodiment. Filter 630 is integrated into the cassette and provides additional filtration of bacteria and endotoxin. The dialysate flows from filter 630 to venous dialyzer 20, which employs high flux membranes. The dialysate flow path 620 connects the venous and arterial dialyzers via a restriction 40 between the two dialyzers. Restriction 40 provides backpressure to drive a significant amount of the dialysate directly into the blood circuit 50 inside venous dialyzer 20. The remainder of the dialysate flows to arterial dialyzer 30.

UF pumps 26 and 28 are provided on the exit side of the arterial dialyzer 30. Those pumps are normally configured to pump at the rate of the fresh dialysate plus an additional amount to remove the fluid accumulated in the patient between treatment sessions. The used dialysate fluid and UF fluid is then circulated to the sorbent cartridge 222 and cleaned before returning to reservoir 612 and receiving an infusate 616 of e.g., calcium chloride, magnesium chloride, potassium chloride and possibly sodium acetate. As described above in connection with system 10, pumps 22 to 28 may operate differently for priming, for bolus infusion or for blood rinseback.

FIG. 11 illustrates a system 710, which replaces dialyzers 20 and 30 with a hemofilter 312. System 710 is configurable to provide predilution, postdilution or both types of HF therapies via valves 56 and pre and postdilution flow lines 712 and 714, respectively. Pre and post dilution HF eliminates the need for an anti-coagulant. System 710 can employ multiple ultrafilters 626 and multiple bypass lines 628 as illustrated for redundancy. Multiple filters in series ensure that if one filter becomes compromised or otherwise does not function properly, the other filter in the series ensures proper filtration. The filters each have a rated log reduction of bacteria and endotoxin. Thus, if bacteria levels reach a high enough point, some bacteria could be carried through the first filter in a series to the second filter in the series, and so on.

Systems 610 and 710 include a number of alternative embodiments. Ultrafilters 626 and/or microfilter 630 may or may not be reusable. Pumps 22 to 28 and flow measuring devices 32 to 38 include any of the alternatives described above in connection with system 10, such as the matched flow equalizers such as in the System 1000™, produced by the assignee of the present invention. Any of the alternatives may be at least partially integrated with the cassette or provided elsewhere in the dialysis machine. A further alternative method is to use other volumetric pumping technology, such as piston pumps (with some piston pumps, depending upon if the piston exposes the solution to air, the ultrafilter needs to be placed after the pumps in the fresh dialysate loop to prevent the solution from becoming contaminated). Still further, flow monitoring could be employed instead of the volumetric pumps. Here, flow sensors measure flow and provide flowrate feedback to one or more pumps located upstream and/or downstream of the dialyzers 20, 30 or hemofilter 312.

Systems Using Peristaltic Pumping

Figure 12:
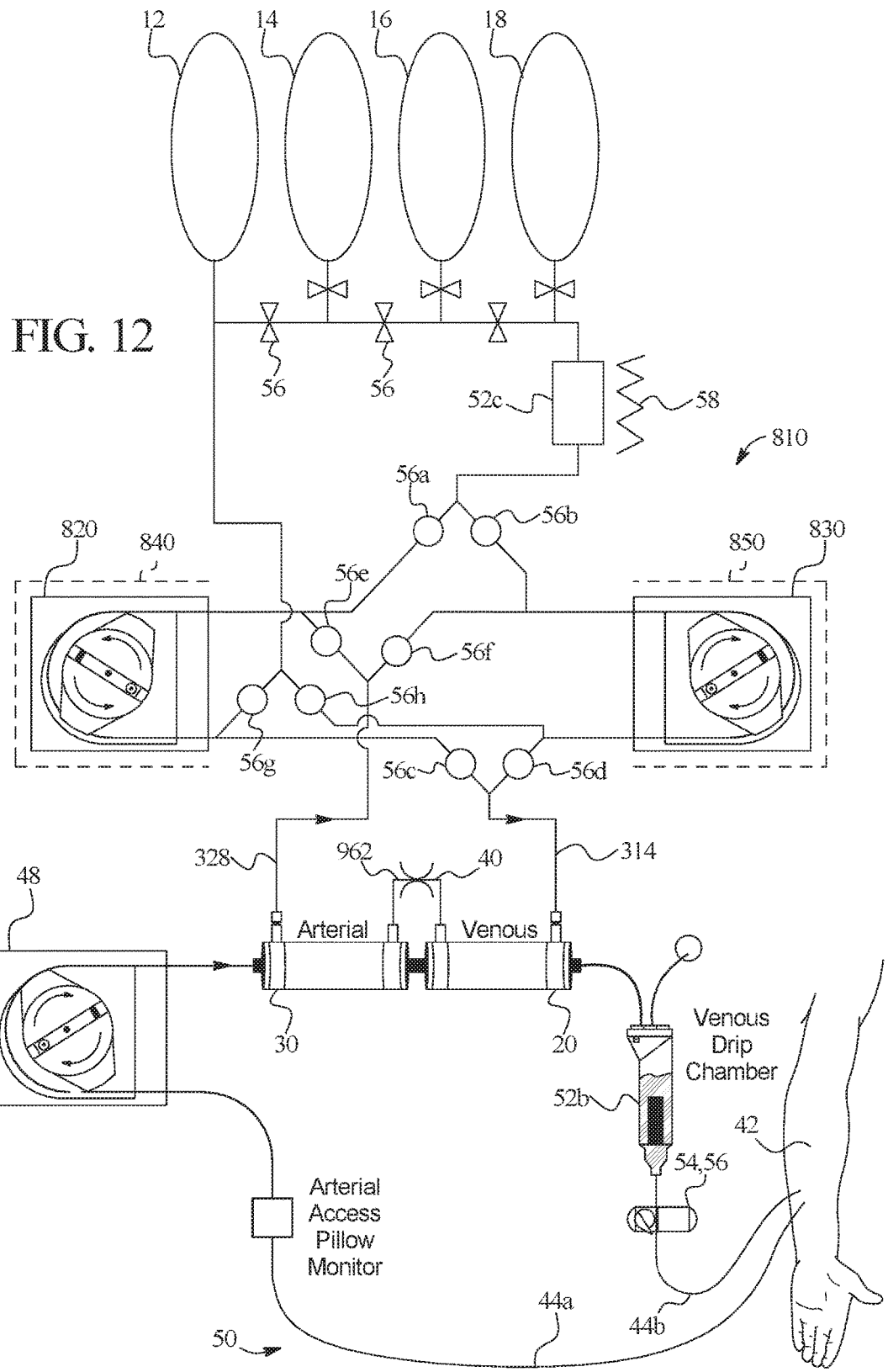
FIGS. 12 and 13 are alternative hemodialysis and hemofiltration systems using peristaltic pumps to pump the therapy fluid.
Figure 13:
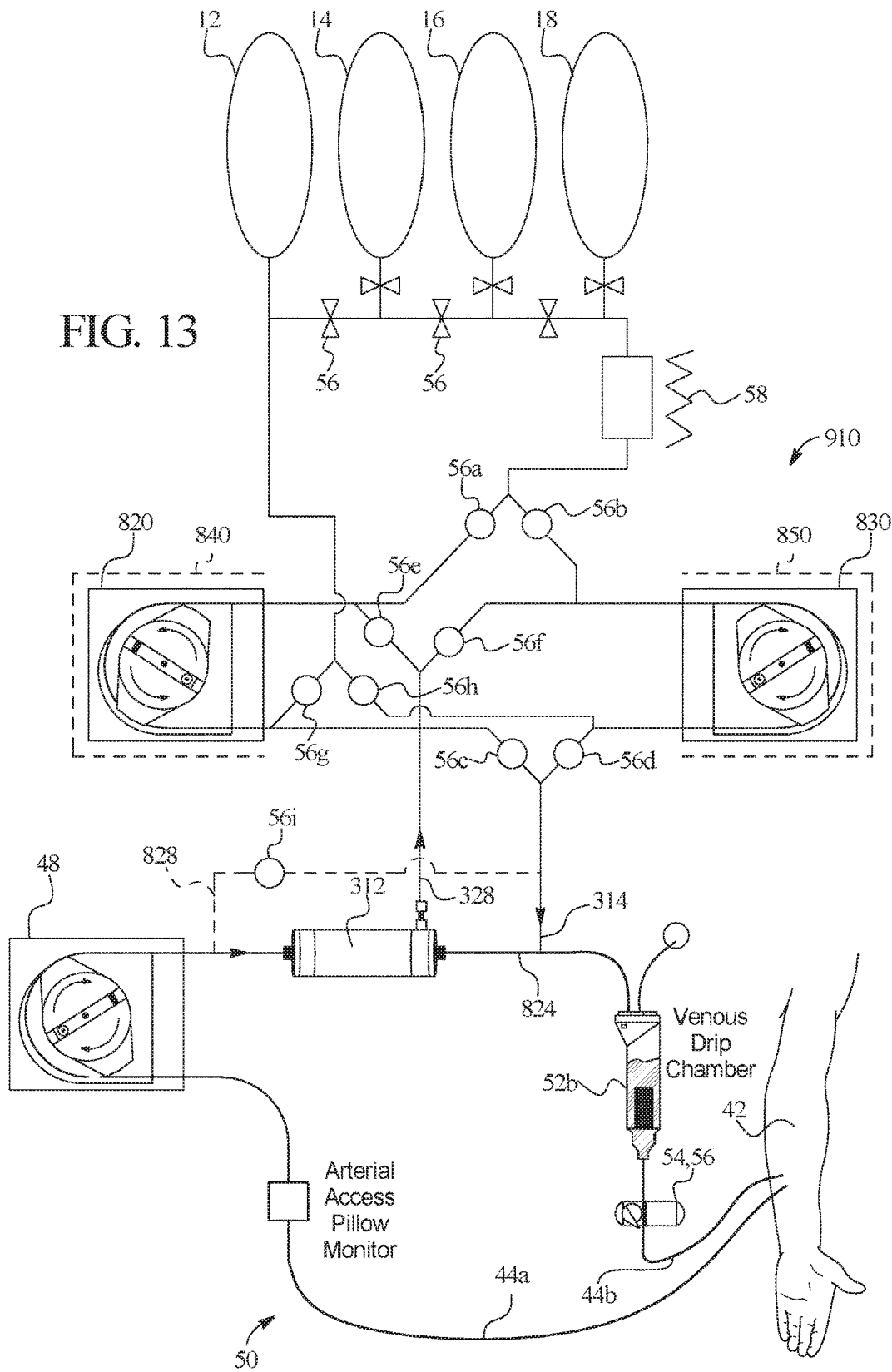

Referring now to systems 810 and 910 of FIGS. 12 and 13, respectively, alternative medical fluid treatment systems using peristaltic pumps 820 and 830 to pump the dialysate fluid from bags 14, 16 and 18 and ultrafiltrate from a blood filter are illustrated. FIGS. 12 and 13 are simplified with respect to the figures illustrating earlier systems. It should be appreciated that many of the components and devices shown above in those systems are also used in systems 810 and 910 as appropriate. It is unnecessary to repeat the inclusion of each of those components and devices in FIGS. 12 and 13. Moreover, elements in FIGS. 12 and 13 listed with like element numbers with respect to those shown above operate the same as described above and include each of the alternatives for those element numbers described above.

System 810 of FIG. 12 illustrates a hemodiafiltration system using inline hemodialyzers 20 and 30, separated by restriction 40, as described above. Blood flows from arterial access line 44a of extracorporeal circuit 50 via peristaltic pump 48, through arterial dialyzer 30, through venous dialyzer 20, into venous drip chamber 52b, through blood leak detector 54 and clamp or valve 56 and venous access line 44b back into patient 42. Dialysate flows from one of the source bags 14, 16 or 18 through drip chamber 52c and past heater 58. In system 810, peristaltic pumps 820 and 830 are used to drive the dialysate or therapy fluid from the source bags to venous dialyzer 20.

Valves 56a to 56h are configured and arranged to enable either peristaltic pump 820 or peristaltic pump 830 to perform either of the fluid infusion or fluid removal tasks, namely, to infuse fluid into venous dialyzer 20 or to pull ultrafiltrate from arterial dialyzer 30. Peristaltic pumps are inherently less accurate than the volumetric diaphragm pumps described above as well as other types of pumps or volumetric devices, such as fluid balancing chambers. Due to this inaccuracy, peristaltic pumps may have to be combined with a balance scale or another balancing method. Peristaltic pumps are, however, easy to sterilize and maintain in an injectible quality state, the pumps are generally hearty, robust and also provide built-in clamping when the pump stops pumping because the pump head pinches closed the tubing wrapped around the head. The pumps are also well accepted by the dialysis community. The valve arrangement of valves 56a to 56h and the use of the peristaltic pumps is advantageous for the above reasons.

The inaccuracy inherent in peristaltic pumps is repeatable especially when the pumps are rotated in the same direction. Systems 810 and 910 provide dual pumps 820 and 830 and valves 56a to 56h that are opened and closed to enable the same pump 820 and 830 to be rotated in the same direction for the same number of pump-in strokes and pump-out strokes. That feature cancels most error associated with the pumps. The pumps then perform additional pump out strokes to remove the desired amount of ultrafiltrate.

It should be appreciated that the above canceling can also be achieved by running one pump in one direction for the appropriate number of strokes and alternating the valves to sequentially pump-in and pump-out with the single peristaltic pump. Such an arrangement creates pulsatile flow, however, which is less desirable than a steady flow from dual pumps 820 and 830. Therapy time is reduced as are the chances of hemoconcentrating the patient.

Valves 56a and 56b enable dialysate heated by heater 58 to flow to either peristaltic pump 820 or 830. Valves 56c and 56d in turn enable fluid to flow from either pump 820 or 830 to venous dialyzer 20. Valves 56e and 56f enable ultrafiltrate to be pulled from arterial dialyzer 30 to either peristaltic pump 820 or 830, respectively. In turn, valves 56g and 56h enable the ultrafiltrate pulled from dialyzer 30 to be pumped via either valve 820 or 830, respectively, to drain bag 12, 14 or 16.

The operation of dialyzers 20 and 30 in combination with restriction 40 does not change in system 810 from their operation described above in connection with system 10 of FIG. 1. The dual operating pumps 820 and 830 enable a continuous flow of fluid into and out of dialyzers 20 and 30. Importantly, as with the membrane pumps 22 to 28 described above, the tubing used with peristaltic pumps 820 and 830 can be sterilized with methods such as gamma, ebeam or ethylene oxide, and operated without compromising such sterilization.

Flow or volume measuring devices 840 and 850 are each provided to operate with a respective pump 820 or 830, respectively. Devices 840 and 850 can provide tachometer feedback, for example, measuring the speed of rotation of the peristaltic pump head in one example. In another example, measuring devices 840 and 850 count to the number of strokes made by the head of peristaltic pumps 820 and 830. In a further alternative embodiment, ultrasonic, mass flow, vortex shedding, or other type of flow measurement technique is used to measure the amount of fluid entering or exiting pumps 820 and 830. Various embodiments showing peristaltic pumps in combination with one or more balancing chamber or volumetric control device are illustrated in detail below.

System 910 of FIG. 13 illustrates a hemofiltration version of system 810 described in FIG. 12. System 910 is similar in all respects to system 810 except that hemofilter 312 replaces hemodialyzers 20 and 30 and restriction 40 of system 810. Also, the inlet line 314 extending from valves 56c and 56d is connected to line 824 extending from hemofilter 312 to venous drip chamber 52b in system 910. In system 810 of FIG. 12, line 314 as illustrated is connected instead to the inlet of venous dialyzer 20. Line 328 in both systems 810 and 910 exits the relevant blood filtering device and flows to valves 56e or 56f. Thus, the functioning of valves 56a to 56h does not change from system 810 to system 910. That is, valves 56a and 56b operate as inlet dialysate or substitution valves in both systems. Valves 56c and 56d operate as outlet dialysate valves in both systems. Valves 56e and 56f operate as ultrafiltrate inlet valves in both systems. Valves 56g and 56h both operate as ultrafiltrate outlet valves in both systems. System 910 optionally provides a bypass line 828 and shunt valve 56i that enables system 910 to perform pre or postdilution hemofiltration as described above.

Any of the alternative embodiments for providing a sterile solution or for regenerating used solution described above are applicable to systems 810 and 910. Further, each of the components described above, such as valves 56, drip chambers 52 (collectively referring to drip chambers 52a, 52b and 52c), heater 58, etc., or those portions thereof that contact the fluids used in the systems, can be provided in a disposable cassette in systems 810 and 910. In particular, shown below are machines that house the flow devices as well as the disposable cassette. Those machines show that a majority of the peristaltic blood pump is located within the machine, with the peristaltic pump head located outside of the machine. Such arrangement is applicable to systems 810 and 910, which use multiple peristaltic pumps. The cassette can have multiple tubing portions that the patient or operator wraps around the externally located peristaltic pump heads for use.

Co-Current Flow

Figure 14:
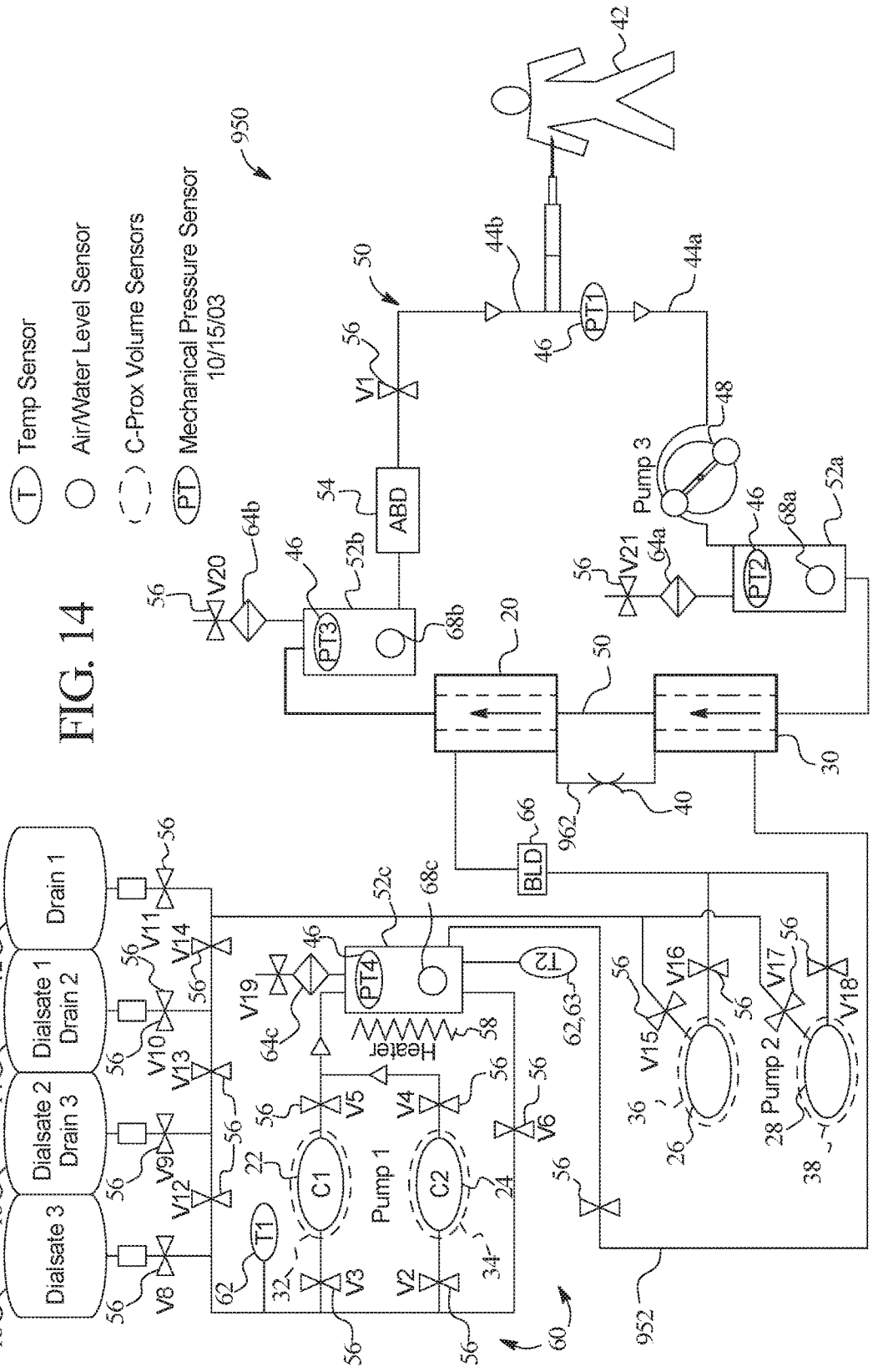
FIG. 14 is an alternative hemodialysis system, wherein the flow of dialysate and blood are co-current.

Referring now to system 950 of FIG. 14, an alternative medical fluid treatment system using co-current flow is illustrated. System 950 of FIG. 14 includes many of the same components described above, for example, in connection with system 10 of FIG. 1. Many element numbers shown in FIG. 14 are the same as the element numbers shown in previous embodiments. Those like element numbers in FIG. 14 operate the same as described above for those numbers and include each of the alternatives described previously for same.

System 950 operates in a similar manner to system 10 of FIG. 1, both of which include dual dialyzers 20 and 30, and a restriction, such as variable restriction 40, placed between the dialyzer portions. System 10 of FIG. 1, it should be appreciated, is a counter-current flow system. That is, dialysate line 314 in FIG. 1, which receives therapy fluid from pumps 22 and 24, in turn feeds the therapy fluid into venous dialyzer 20. The fluid flows through venous dialyzer 20, variable restriction 40 and through arterial dialyzer 30. At the same time, blood flows initially into arterial dialyzer 30, continues through blood circuit 50, through venous dialyzer 20 and eventually into patient 42. System 950 of FIG. 14, on the other hand, includes output dialysate line 952 instead of line 314 in FIG. 1. Dialysate line 952 carries fresh and heated therapy fluid into arterial dialyzer 30 instead of venous dialyzer 20. The dialysate in system 950 therefore flows from arterial dialyzer 30, through variable restriction 40, into venous dialyzer 20 and out venous dialyzer 20 to ultrafiltrate pumps 26 and 28. Blood leak detector 66 is alternatively placed upstream of pumps 26 and 28 as illustrated in FIG. 14 or downstream of those pumps as illustrated in FIG. 1.

Co-current flow of dialysate via line 952 of system 950 is beneficial in one respect because, as with predilution hemofiltration, dialysate is introduced into arterial dialyzer 30 at the start of the blood filtration portion of blood circuit 50, and may, therefore, help to prevent hemoconcentration of the patient's blood. Variable restriction 40 operates to backfilter therapy fluid inside arterial dialyzer 30 into extracorporeal circuit 50. Afterwards, blood and therapy fluid flow into venous dialyzer 20 via bloodline 50 and are subjected to diffusive clearance via the non-backfiltered dialysate that flows from arterial dialyzer 30 into venous dialyzer 20 through restriction 40. The roles of dialyzers 20 and 30 are reversed in system 950 with respect to system 10 of FIG. 1, wherein the clearance mode in venous dialyzer 20 is primarily diffusive, while the clearance mode in arterial dialyzer 30 is primarily convective.

Operation of system 950 is otherwise substantially similar to that described above in connection with system 10 of FIG. 1. While system 950 is operable with supply bags 14 to 18 and drain bag 12, any of the above-described embodiments for supplying fresh dialysate are alternatively operable with system 950. Further, system 950 is operable with the regeneration sorbent system described above in connection with system 210 of FIG. 5. Still further, co-current flow can be provided in connection with the hemodiafiltration system 510 of FIG. 8. Still further, the volumetric diaphragm pumps 22 to 28 can be replaced by peristaltic pumps 820 and 830, in accordance with the teachings described above in connection with system 810 of FIG. 12.

Ultrafiltrate Control-Boyle's Law

Figure 15:
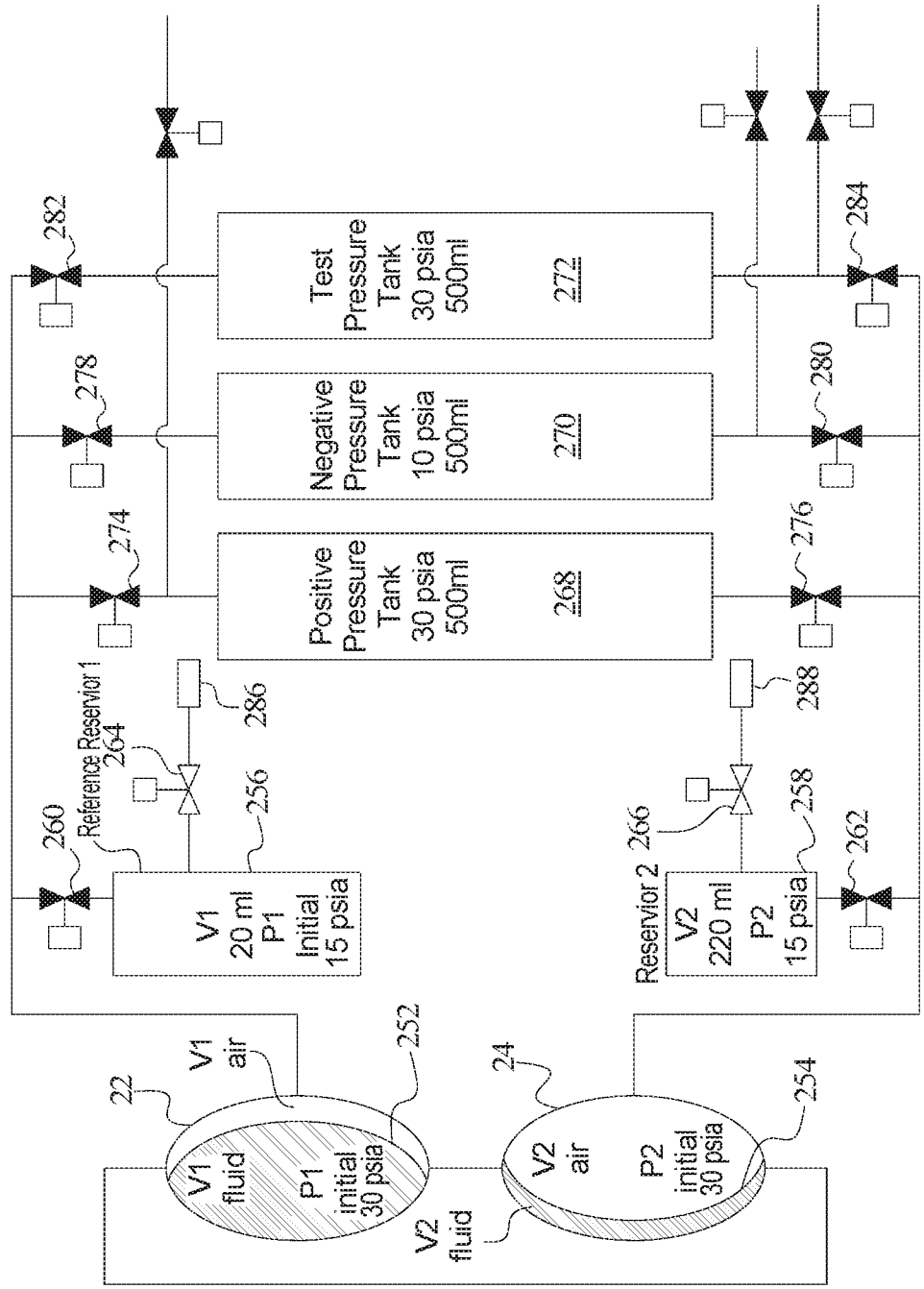
FIGS. 15 and 16 are schematic views of one embodiment of a pneumatically controlled method and apparatus for controlling the volume of ultrafiltrate removed from the patient.
Figure 16:
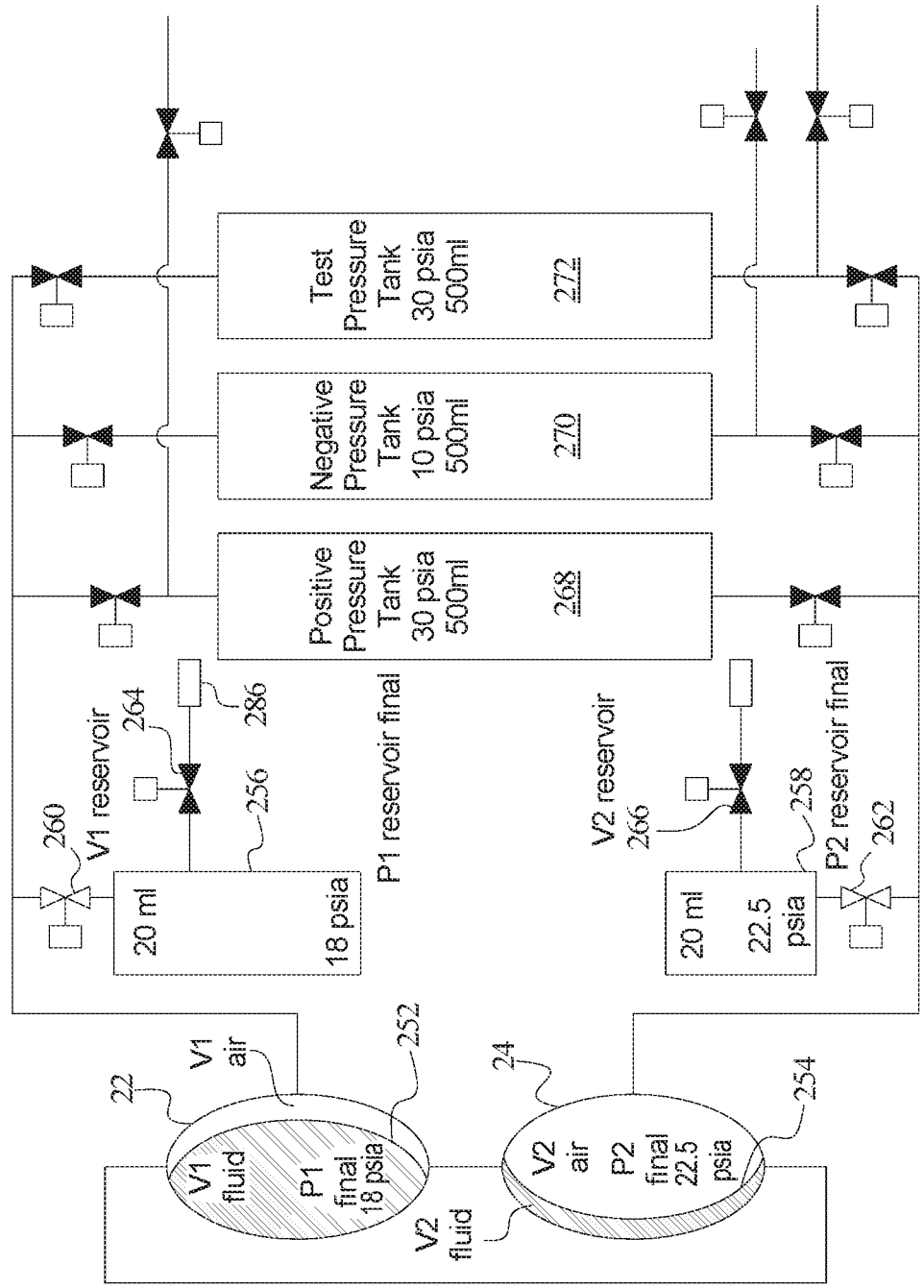
Figure 17:
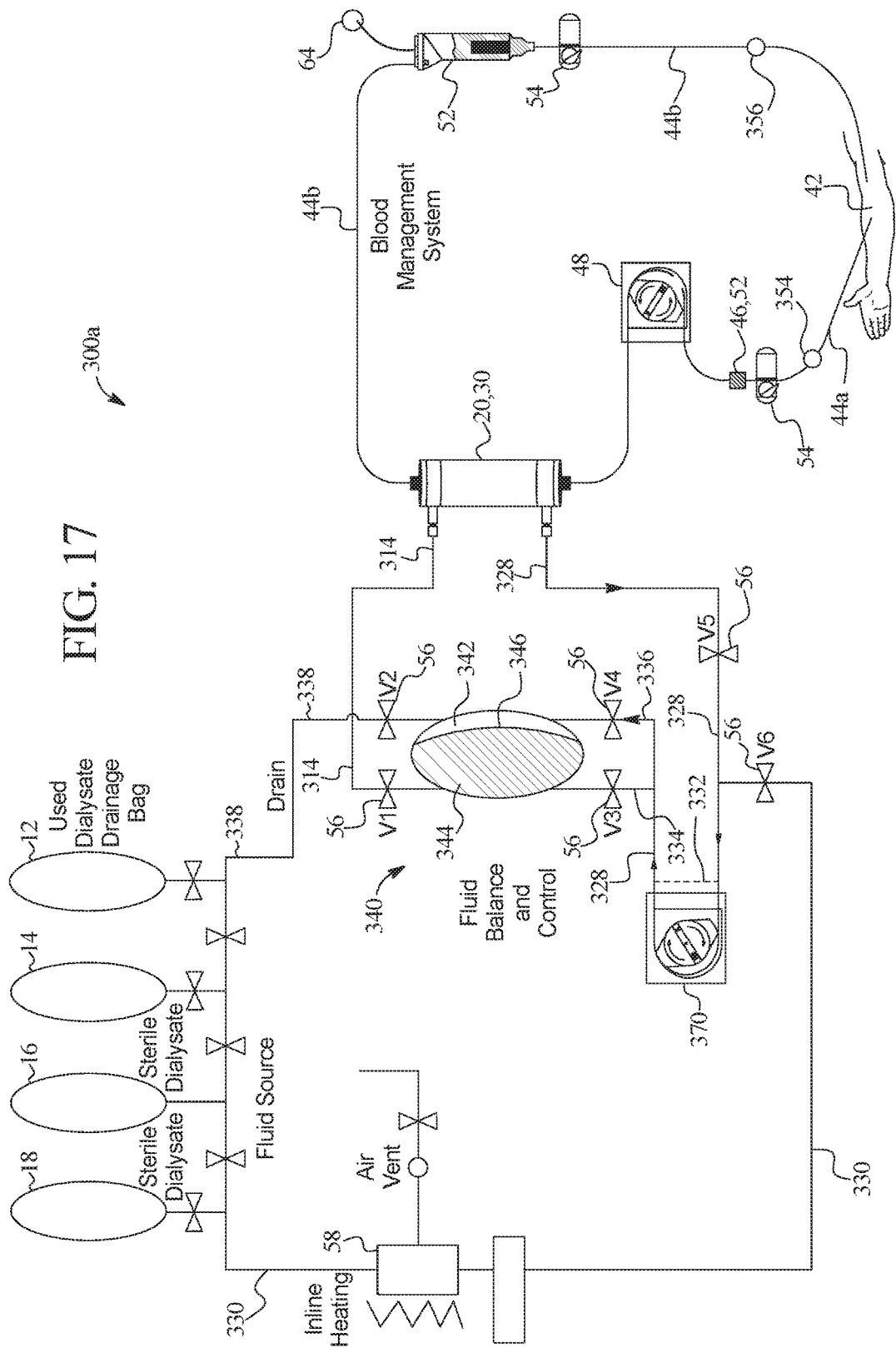
FIGS. 17 to 22 are schematic flow diagrams of various embodiments for controlling the volume of ultrafiltrate removed from the patient via a single balance chamber.

Referring now to FIGS. 15 and 16, a method of determining the volume of fluid pumped through a membrane pump is illustrated. Pumps 22 and 24 described above are shown for example. As discussed herein, pumps 22 and 24 include pump chambers defined at least partially by a rigid cassette, such as cassette 100*a*. The cassette includes a flexible membrane or sheeting. Another portion of the pump chamber is defined in one embodiment by the renal replacement therapy machine into which the cassette is inserted. In FIGS. 15 and 16, pump 22 includes a membrane 252. Pump 24 includes a membrane 254. Positive and negative tanks 268 and 270 move membranes 252 and 254 to pump fluid via positive and negative pressure via valves 274, 276, 278 and 280 as needed. The pneumatic system also includes reference reservoirs 256 and 258. Reservoir 256 communicates with air residing on the non-fluid side of membrane 252 of pump 22. Likewise, reference reservoir 258 communicates with air residing on the non-fluid side of membrane 254 of pump 24.

Reference reservoirs 256 and 258 have a constant and known volume. In the equations shown below the volumes of reservoirs 256 and 258 are designated as V1 reservoir and V2 reservoir. In the example, the volumes of pressure sensors that measure V1 reservoir and V2 reservoir are 20 ml. The blood therapy treatment unit also has pressure sensors that measure the pressure inside reference reservoirs 256 and 258. In FIG. 15, when valves 260 and 262 are closed and vent valves 264 and 266 leading to sound absorbers 286 and 288 are open, the pressure inside reservoirs 256 or 258 reaches atmospheric pressure or approximately 15 psia. In FIG. 16, when vent valves 264 and 266 are closed and reservoir valves 260 and 262 are opened, the pressure inside pump chamber 1 equalizes with the pressure inside reservoir 256. The pressure inside pump chamber 2 equalizes with the pressure inside reservoir 258.

The cassette is also configured such that a pressure sensor housed within the blood therapy unit measures the initial and final air fluid pressures, inside pumps 22 and 24. In the equations shown below, the fluid pressure inside pump 22 is designated as P1 chamber. The fluid pressure inside pump 24 is designated as P2 chamber. The fluid pressures vary from an initial pressure to a final pressure. Likewise, the pressures P1 and P2 within reservoirs 256 and 258 designated as P1 and P2 reservoir, respectively, vary from an initial pressure to a final pressure.

The volume of air within either one of the pumps 22 or 24 (volume V1 for pump 22 which is supposed to be full is shown for example) is calculated via Equation 1 as follows:

$$V1(\text{air, full chamber}) = \frac{(P1 \text{ reservoir, initial}) - (P1 \text{ reservoir, final})}{(P1 \text{ chamber, final}) - (P1 \text{ chamber, initial})} \times V1(\text{reservoir}) \quad \text{Equation 1}$$

The volume of air for an empty chamber for either one of the pumps 22 or 24 (shown in this example for pump 24 or V2) is calculated according to Equation 2 as follows:

$$V2(\text{air, empty chamber}) = \frac{(P2 \text{ reservoir, initial}) - (P2 \text{ reservoir, final})}{(P2 \text{ chamber, final}) - (P2 \text{ chamber, initial})} \times V2(\text{reservoir}) \quad \text{Equation 2}$$

Each of the pressures for each of the pumps 22 and 24 shown in Equation 1 is measured via a suitably placed transducer. The final air pressure within the reservoirs 256 and 258 is also measured. The final pressure of air within the chambers, which should equal the final reservoir pressure can be double checked. The measured pressures satisfy the numerators and denominators in Equations 1 and 2. As discussed above, the volumes of the reservoirs V1 and V2 are constant and known.

For each pump then, Equation 3 calculates the volume pumped for a stroke as follows:

$$\text{Volume fluid pumped for pump 1 or 2} = V1 \text{ or } V2 \text{ (air, empty chamber)} - V1 \text{ or } V2 \text{ (air, full chamber)} \quad \text{EQUATION 3}$$

The fluid volume pumped for a stroke of a pump is equal to the volume of air when that pump chamber is empty or void of fluid less the volume of air in that pump chamber when the chamber is expected to be full of fluid. It should be appreciated that the Equations 1 to 3 that are derived from Boyle's law compensate for air bubbles that may be present in the dialysate and for instances where membranes 252 and 254 may not travel fully to one side or the other of the pump chambers of pumps 22 and 24, respectively.

The above-described method provides an accurate, after-the-fact, measurement of the volume of fluid that has been moved by either one of the pumps 22 and 24. By using the volumetrically controlled pumps, an exact amount of fluid can be exchanged with the patient and an exact amount of ultrafiltrate can be removed from the patient by setting the fluid removal pumps, e.g., pumps 26 and 28, to pump faster or more volume than the fluid inlet pumps 22 and 24 (see for example, in FIGS. 1, 4, 6, 7). Because the volume for each stroke can be calculated, the amount of fluid removed from the patient can be summed and controlled.

It should be appreciated that Equations 1 to 3 described above could be used in a machine that mechanically moves membranes 252 and 254. In such case, positive and negative pressure tanks 268 and 270 would not be needed, however, separate reference reservoirs 256 and 258 as well as a test pressure tank 272 are needed. Test pressure tank 272 may be employed even in the present embodiment so that pressure tanks 268 and 270 may be operated independent from the volume control.

Calculating the volume of fluid pumped according to Equations 1 to 3 provides information on how much volume has been moved per pump stroke. The equations do not provide real time information of actual fluid flow. That is the valve opening and closing, sequence in FIGS. 15 and 16 occurs between pump strokes, when valves 274, 276, 278 and 280 are closed, isolating the pumps from the positive and negative pressure sources. When the pumps are pumping fluid, reference reservoirs 256 and 258 are isolated from the pump.

If fluid flow stops or occurs at a flow rate that is greater than a desired flow rate, the pneumatic system may not detect this until after the undesired fluid flow rate has occurred. In blood therapy systems, such as dialysis, hemofiltration or hemodiafiltration, if the withdrawal of the fluid from circulating blood exceeds about thirty percent of the blood flow rate, the blood thickens and may clog the dialyzer or hemofilter fibers. If the dialyzer or filter becomes clogged, therapy may have to be terminated and the patient may lose an amount of blood trapped in the extracorporeal circuit.

The apparatus shown in FIGS. 15 and 16, however, provides a solution for real-time flow rate data for both blood flow and dialysate infusion and removal. The real-time flow rate is again calculated using principals of Boyle's law. As described above, equations one and two calculate the volume of air within the pump chambers 22 and 24 when those chambers are either full or empty. In this method, valves 260 and 262 to reference reservoirs 256 and 258 are closed and the appropriate valves to positive pressure tank 268 and negative pressure tank 270 are opened. For example, valve 274 may be opened to supply positive pressure to pump 22 to push fluid from that pump. At the same time, valve 280 may be opened to pull a vacuum on pump 24 to draw fluid into the pump. Since the volumes of air in the pump chambers are known from Equations 1 and 2, those volumes are added to the known volumes of air in pressure reservoirs 268 and 270 (e.g., 500 ml) to form total initial volumes. The pressures are measured as the membranes 252 and 254 move due to the supplied pressures. The change in pressure over time corresponds to a change in volume one time, which yields a flowrate.

In the following equations, the total initial volume in pump 22 and the respective pressure chamber is V1 total, initial=V1 chamber, initial plus Vpos/neg tank. The total volume in pump 24 and the respective pressure chamber is V2 total, intial=V2 chamber, initial plus Vpos/neg tank. The pressure of the pump 22 system as measured at the positive or negative tank is initially Ppos/neg, tank, intial. The pressure of the pump 24 system as measured at the positive or negative tank is initially Ppos/neg tank, initial. The pressure of either system at any time T is Ppos/neg tank, time T. The volume in either pump at time T is therefore as follows:

$$V1 \text{ or } V2 \text{ total,} \quad \text{time } T = \frac{P_{pos/neg} \text{ tank, initial}}{P_{pos/neg} \text{ tank, time } T} * V1 \text{ or } V2 \text{ total, initial} \qquad \text{Equation 4}$$

The fluid moved by either pump at time T is therefore as follows:

$$V_{fluid} \text{ moved by pump 1 or 2} = V1 \text{ or } V2 \text{ total, time} \\ T - V1 \text{ or } V2 \text{ total, initial} \qquad \text{EQUATION 5}$$

Knowing the time T and the volume of fluid moved by pump 22 or 24 at time T, the flow rate on a real time basis may be calculated, displayed and used to control the renal failure therapy systems of the present invention.

Ultrafiltrate Control—Single Balance Chamber

Each of the systems 10, 110, 210, 310, 410, 510, 610, 710 and 950 that employ membrane pumps, such as pumps 22, 24, 26 and 28 are capable of metering out precise amounts of fluid, which can be controlled as described above for example via Boyle's Law. For manufacturing and cost reasons, however, it may be desirable to use a different type of pump to move spent and effluent dialysate. For example, peristaltic pumps, such as the blood pump 48 described above, may more easily integrate into a disposable cassette or tubing set because the disposable part of a peristaltic pump is essentially a loop of tubing. The accuracy of peristaltic pumps, however, may not alone be precise enough for pumping dialysate in systems, such as hemofiltration, hemodialysis and hemodiafiltration, in which a prescribed amount of ultrafiltrate or effluent dialysate needs to be removed from the patient.

Patient 42 between dialysis or hemofiltration treatments gains water depending on the extent of kidney loss and fluid intake. Many people suffering kidney failure do not have the ability to urinate. Over the time between dialysis treatments, those patients accumulate fluid. The patient's total fluid weight gain can vary over different treatments based on the amount of fluid the patient has consumed between treatments and the amount of time between treatments. Therefore, the systems and methods of the present invention need to have a controllable and accurate way of removing whatever amount of fluid is needed to be taken from the patient during the home treatment. Because home patients can treat themselves more often, the amount of fluid that needs to be removed will be typically less than that for in-center treatments. Nevertheless, the home dialysis machine needs to be able to remove the amount of fluid gained between treatments.

Referring now to FIGS. 17 to 22, various systems 300a to 300f (referred to herein collectively as systems 300 or generally as system 300) employing a single balance chamber 340 are illustrated. Systems 300a, 300b, 300c, 300d, and 300e each operate with a peristaltic dialysate pump 370. As discussed above, a peristaltic pump is desirable for a cassette-based system because the cassette portion of the pump consists primarily of a looped tube that fits around the pumping head housed by the renal failure therapy machine.

Figure 22:
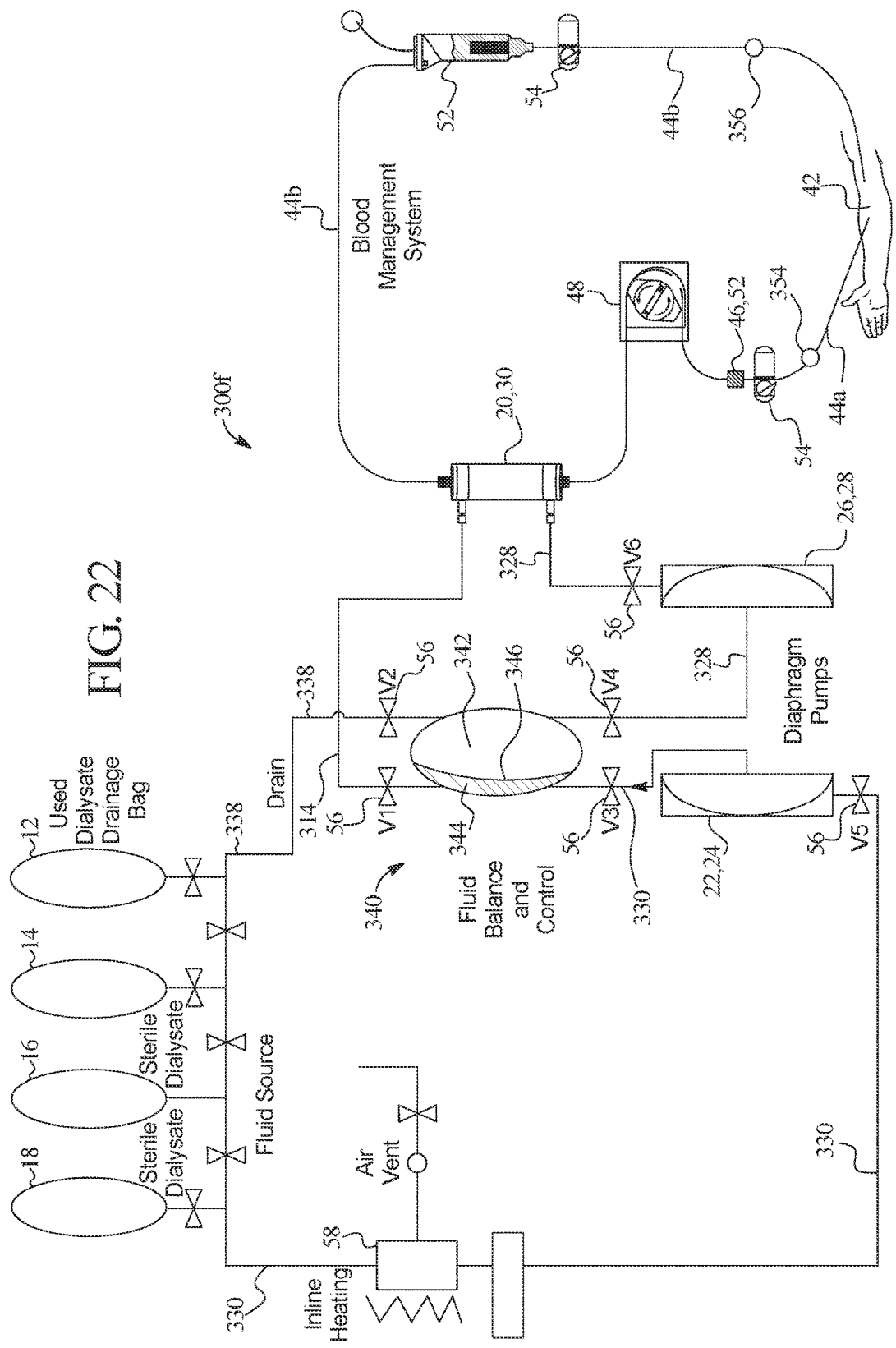

Balancing chamber 340 provides the level of volumetric accuracy provided by the membrane pumps discussed above. The majority of systems 300 use peristaltic pump 370 to drive the dialysate, while balancing chamber 340 meters a precise amount of dialysate to the dialyzer, hemofiltration line, etc. Balance chamber 340 in turn meters a pressurized amount of ultrafiltrate from the dialyzer or hemofilter. System 300f of FIG. 22 shows one alternative embodiment, which combines balance chamber 340 with one of the fresh dialysate membrane pumps 22 or 24 and one of the effluent dialysate membrane pumps 26 or 28 discussed above.

Figure 18:
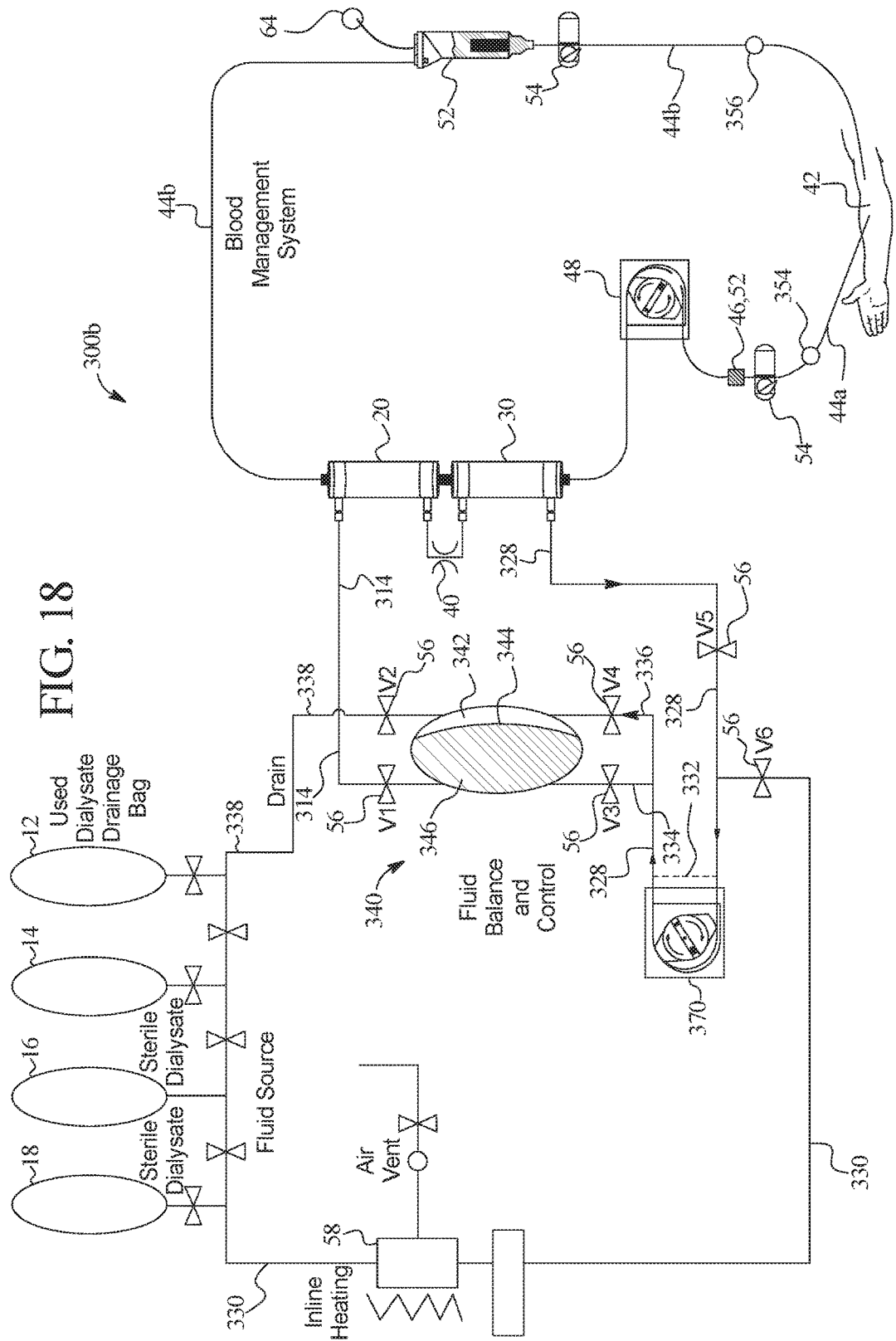
Figure 19:
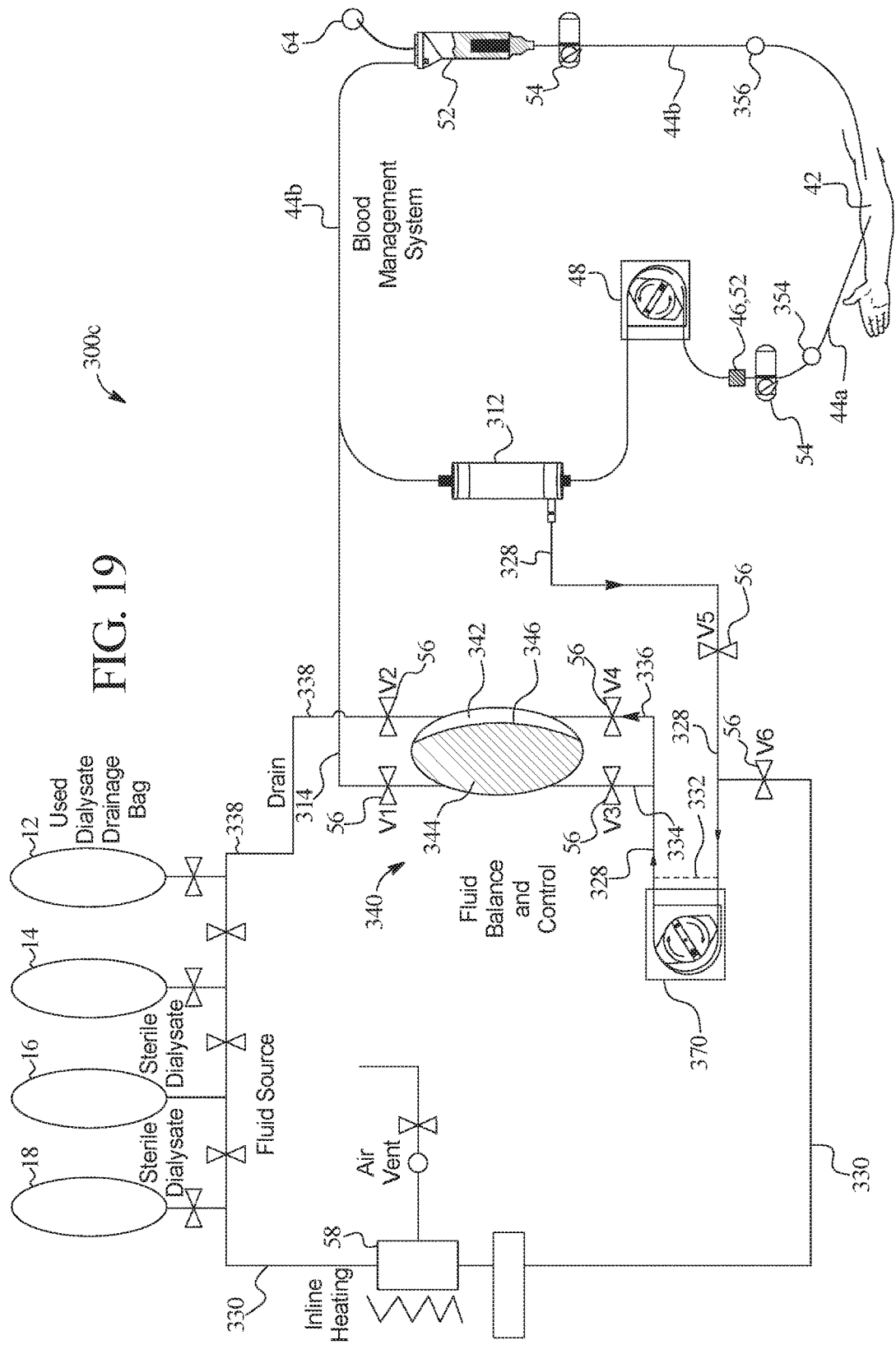

One primary difference between systems 300a to 300d is the modality or type of therapy with which balance chamber 340 and peristaltic dialysate pump 370 are used. System 300a of FIG. 17 uses a single dialyzer 20 or 30. In system 300a, the modality performed is a primarily diffusive hemodialysis treatment unless the dialyzer has an internal restriction as mentioned previously. However this dialyzer requires a high flux membrane. Longer and narrower dialyzers will increase the percentage of backfiltration. Also a dialyzer having an internal flow restriction suitable for use, such as described in commonly owned U.S. Pat. No. 5,730,712, entitled "Extracorporeal Blood Treatment Apparatus and Method", is incorporated herein by reference. That dialyzer as indicated is limited to having a fixed orifice. The modality or therapy of system 300b of FIG. 18 is the advanced convection hemodialysis ("ECHD") treatment provided by arterial and venous high flux dialyzers 20 and 30, respectively, which are separated by variable restriction 40. The modality or treatment provided by system 300c of FIG. 19 is the convective treatment, hemofiltration, wherein substitution fluid is pumped directly into venous line 44b, and wherein ultrafiltrate is removed via a hemofilter 312.

Figure 20:
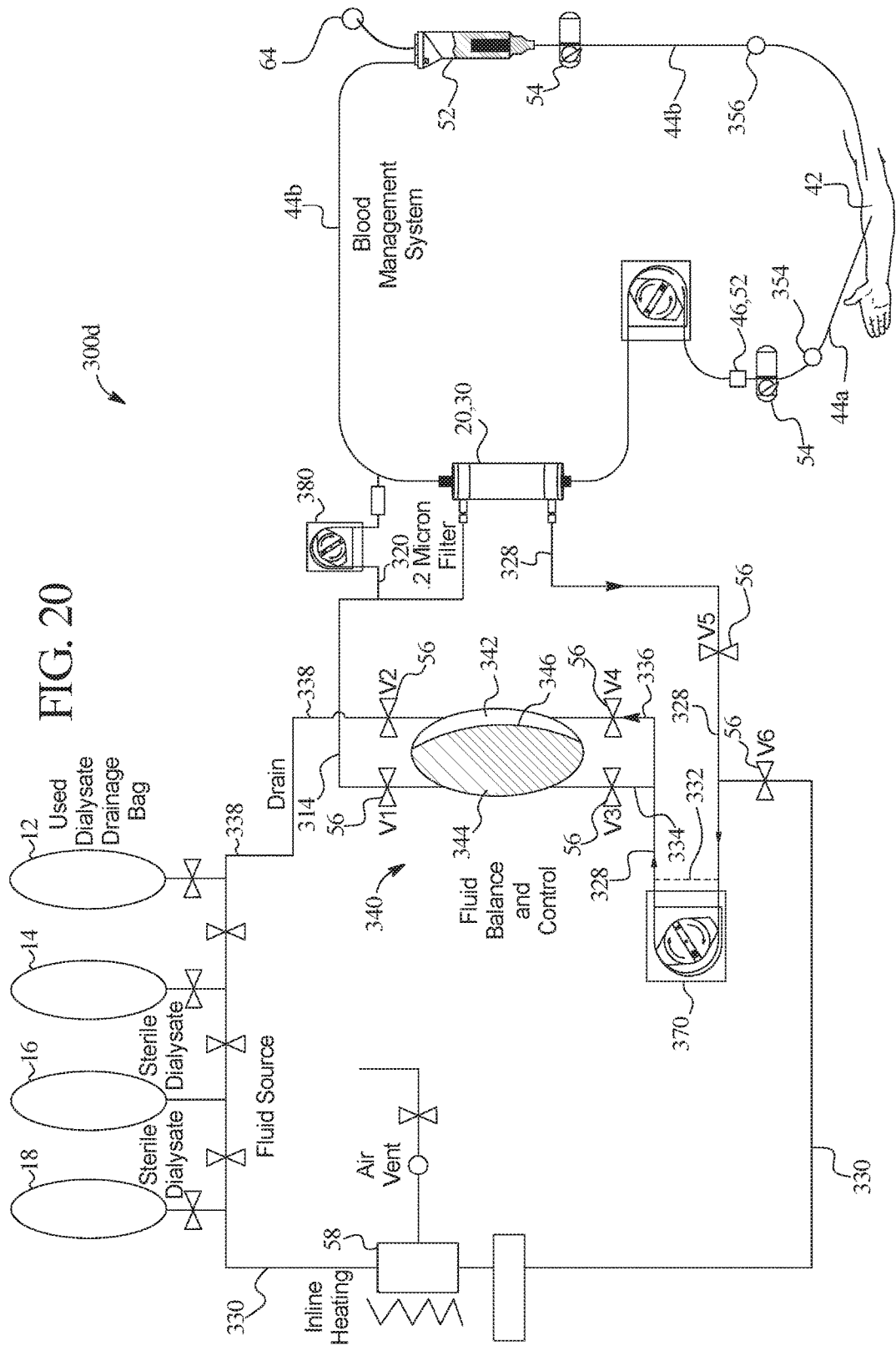

System 300d of FIG. 20 illustrates balance chamber 340 operating in combination with a hemodiafiltration modality. As discussed above, hemodiafiltration combines the diffusive clearance of hemodialysis with the convective clearance of hemofiltration. As seen in FIG. 20, a dialyzer 20 or 30 is provided. Also, a separate line 320, coupled with an additional peristaltic pump 380, feeds dialysate or substitution fluid directly into venous line 44b. FIGS. 17 to 20 illustrate that the volumetric control of ultrafiltration via single balance chamber 340 can be provided for many different types of modalities, such as hemodialysis, ECHD, hemofiltration and hemodiafiltration. The remainder of the description may in certain cases be specific to dialysis or ECHD. It should be appreciated, however, that those teachings are applicable to each of the systems 300 shown in FIGS. 17 to 20.

Viewing any of the systems 300, effluent or spent dialysate flows from a dialyzer 20, 30 or hemofilter 312 through effluent line 328 and valve V5 to peristaltic dialysate pump 370. While pump 370 in one preferred embodiment is a peristaltic pump, pump 370 can alternatively be of any desired variety, such as a piston-driven diaphragm pump, a pneumatic pump or a gear pump. The output of fluid from pump 370 flows via valve V4 to a spent side 342 of the balance chamber 340. Similar to the flexible membrane in the membrane pump, balance chamber 340 is separated into a spent compartment 342 and a fresh compartment 344 via a flexible membrane 346. As discussed herein, valves 56, such as valve V4, may be any suitable type of valve, such as a standard solenoid valve or a volcano-type valve formed partially in the cassette, which is the same or similar to that used in a HomeChoice® system.

Balance chamber 340 is a passive volumetric metering device. The same or substantially the same amount of fluid is pushed out of balance chamber 340 as is received into balance chamber 340. Pumping effluent dialysate into spent compartment 342 in turn pushes membrane 346, which forces an equal amount of fresh dialysate to exit fresh compartment 344 and travel through valve V1 in line 314 and into dialyzer 20, 30 or into venous line 44b depending on the modality used. FIGS. 17 to 20 are not meant to describe each of the flow components that would be associated with the respective system 300. For example, if balance chamber 340 pushes substitution fluid through valve V1 and inlet line 314, a suitable check valve would be placed in line 314, which would prevent blood from backing into balance chamber 340. When enough effluent dialysate enters spent chamber 342 via valve V4, so that membrane 346 traverses all the way or substantially all the way towards the chamber wall of fresh compartment 344, valves V1, V4 and V5 shut off.

FIGS. 17 to 20 show a pressure relief 332 located between the inlet and outlet of dialysate pump 370. In one embodiment, pressure relief 332 includes a check valve that cracks or relieves at a specific pressure. Alternatively, pressure relief 332 includes a valve seat that relieves pressure at a preset value. For example, a spring tension can control the amount of force or pressure within the pressure relief line that is needed to crack or open pressure relief 332. When system 300 is used with a disposable cassette, the opening of the valve or seat is configured so that the relieved dialysate is collected and does not contact any of the components within the renal failure therapy machine.

In an alternative embodiment, dialysate pump 370 is placed upstream of heater 58. In such case, pressure relief 332 can extend from the inlet of dialysate pump 370 to fresh dialysate inlet line 334 upstream of valve V3. In yet another alternative embodiment, pressure relief 332 incorporates sterile dialysate bags or substitution bags 14 to 18. That configuration is desirable because it prevents inline heater 58 from overheating fluid when idle, e.g., during an ultrafiltration stroke.

A cycle in which effluent fluid is removed from the dialyzer or hemofilter and fresh fluid is sent to the patient or dialyzer has been described. A next cycle sends fluid to drain. Here, heated and fresh dialysate from one of supplies 14, 16 or 18 flows through valve V6, dialysate pump 370, valve V3 and into dialysate compartment 344 of balance chamber 340. Valves V1, V4 and V5 are closed. The receipt of fresh dialysate into compartment 344 pushes flexible membrane 346, causing an equal amount of spent or effluent dialysate to drain via valve V2 and drain line 338. Depending on the point in time in the therapy in which this drain cycle takes place, spent effluent can be sent to drain bag 12 or one of the used supply bags 14 or 16. Once all of the spent dialysate in chamber 342 is emptied through valve V2 and drain line 338, all valves V1 to V6 are shut off. The fill with spent fluid and pump to patient cycle may then be repeated via the cycle described above.

It should be appreciated that the two cycles just described ensure that an equal amount of fluid is sent to the patient and taken from the patient. A UF sequence is described below in which fluid is taken from the patient but not sent to the patient. Calculating the total volume of ultrafiltrate moved is readily done in the illustrated systems 300. The cumulative volume of the UF cycles is added to determine the total amount of fluid removed from the patient.

In one embodiment, pump 370 is run at a slower speed when fresh dialysate is pumped to the dialyzer or patient than when dialysate is pumped from the patient. The difference in speed increases the time that fresh dialysate is flowing to the dialyzer. For hemodialysis, the speed difference increases the diffusion time by increasing the time that dialysate is flowing along the hollow fibers within the dialyzer. The increased time also benefits HF, HDF and ECHD by producing a more gradual ultrafiltration of the patient. The gradual ultrafiltration reduces the risk of hemoconcentration.

To remove ultrafiltrate, system 300 begins from an all valves closed position and opens valves V2, V3 and V5. Pump 370 causes effluent dialysate to fill the fresh compartment 344 with spent dialysate. That action moves membrane 346 and forces an equal amount of spent fluid previously removed from the patient in spent chamber 342 to be pushed through valve V2 and line 338 to one of the drain bags. Because the source of fluid used to push this amount of fluid to drain is used dialysate, the amount of used dialysate pumped into fresh compartment 344 is also removed from the patient as ultrafiltrate. That is, there is a small net loss of fluid from the patient during this cycle. In one embodiment, the ultrafiltrate cycle just described is timed to occur every so often during the previously described pump to patient and pump to drain cycles, so as to remove an overall net amount of ultrafiltrate that has collected in the patient between treatments. That net amount is entered into the machine at the start of therapy.

One potential drawback of the single balance chamber 340 and single dialysate pump 370 approach is that when spent dialysate is pulled from the dialyzer or hemofilter through line 328 and line 336 via pump 370 into the spent chamber or compartment 342, a small amount of fresh dialysate is also pushed into spent compartment 342. That small amount of fresh dialysate is the amount that remains in the tubing leading from valve V6, bending around peristaltic pump 370, and extending further along line 328 towards valves V3 and V4. While the single pump and single balance chamber system is desirable from the standpoint of having a cassette that is simple and relatively inexpensive, it may not be desirable to lose fresh dialysate especially if bagged sterilized dialysate is used. It should be appreciated, however, that if the dialysate is made online, the drawback is less of a concern.

Figure 21:
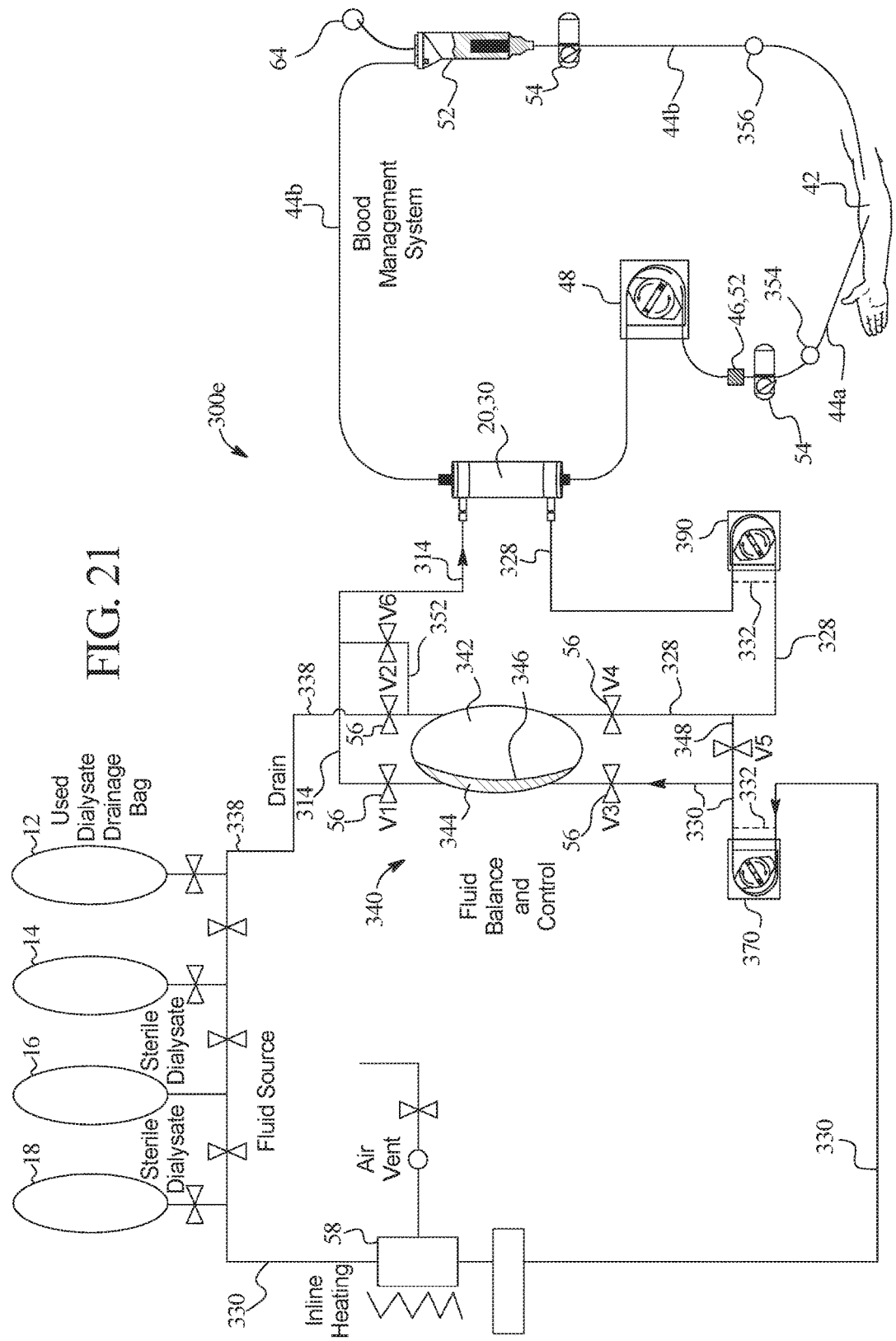

Referring now to FIG. 21, system 300e includes an additional dialysate pump 390, which is dedicated to removing spent or effluent fluid from the dialyzer or hemofilter. Dialysate pump 370 in turn is dedicated to pumping fresh dialysate. Dialysate pump 390 in one embodiment is a peristaltic pump, however, pump 390 may be of any of the types described above for dialysate pump 370. Moreover, while the alternative pump configuration of system 300e is shown for simplicity in combination with a single dialyzer 20 or 30, the pumping configuration of system 300e is compatible with any of the modalities set forth in FIGS. 17 to 20.

In the alternative pump arrangement of system 300e, pump 390 pumps spent fluid through line 328, valve V4 and into the spent compartment 342 of single balance chamber 340. That action causes membrane 346 to move and push an equal amount of fresh dialysate from fresh chamber 344 through valve V1, line 314 and into the dialyzer or patient. At the end of the pump to patient cycle, all valves shut off. Afterwards, valves V2 and V3 open allowing fresh dialysate pump 370 to pull fresh, heated dialysate from one of the supplies, through line 330, through valve V3 and into fresh compartment 344. That action moves membrane 346 to push spent dialysate from spent compartment 342 through valve V2 and line 338, to one of the drain bags.

Each of the alternative configurations for the placement of pressure relief 332 is equally applicable to the dual dialysate pump system 300e. In a further alternative embodiment (see FIG. 23), pressure relief 332 is located instead from the outlet of dialysate pump 370 across to the inlet side of heater 58. Here, pressure relief 332 connects to line 330 between supply bags 14 to 18 and heater 58 and line 330 downstream of pump 370.

To remove ultrafiltrate from the patient via the dual dialysate pump system 300e, with the spent compartment 342 full of effluent dialysate, valves V2, V3 and V5 are opened. Spent fluid pump 390 pumps effluent fluid through line 328, valve V5, line 348 and valve V3 into fresh compartment 344. Such action causes membrane 346 to move and push effluent fluid from compartment 342 through valve V2, line 338 and into one of the drain bags. Because the source of matching fluid for the balance chamber is used dialysate, that amount of matching fluid is removed from the patient as ultrafiltrate.

It should be appreciated that after the ultrafiltrate stroke, the next action is to again pump spent fluid from the dialyzer or hemofilter through valve V4 into spent chamber 342. That action causes membrane 346 to move and in turn pump one balance chamber volume worth of spent fluid from fresh compartment 344 (used previously to push the volume of ultrafiltrate) through line 314 to either the dialyzer or the patient. The spent dialysate still provides a clearance benefit to the patient, especially with respect to larger molecules, such as (32M. This action also extends the life of a certain amount of the dialysate, which is beneficial especially in the case of a home treatment using sterilized and bagged fluid.

Referring now to FIG. 22, an alternative hybrid system 300f is illustrated. System 300f provides the single balance chamber 340 in combination with a dialysate fill pump 22, 24 and an ultrafiltrate removal pump 26, 28. In an embodiment, the fill and removal pumps are membrane pumps as described above. The volumetric pumps eliminate the need for the additional valve V5 and ultrafiltrate line 348 in FIG. 21. Otherwise, the two systems are very similar, including the dedicated dialysate removal line 328 operating with pump 26, 28 and a dedicated dialysate fill line 330 operating with a dedicated pump 22, 24.

As with the other systems, system 300f is operable with any of the modalities discussed herein and is illustrated only for convenience in combination with a single dialyzer 20, 30. The advantage of system 300f is that there is no mixing of fresh and spent dialysate at the balancing chamber. It should be appreciated that even in FIG. 21, with a separate dialysate pump 390, a small amount of fresh solution will be mixed with spent dialysate during the ultrafiltrate cycle in which pump 390 pushes fluid through line 328, valve V5, line 348 and a small portion of line 330 and valve V3 into fresh compartment 344. In FIG. 22, ultrafiltration is performed by opening valve V6 and pulling a predetermined amount of spent dialysate through pump 26, 28. Valves V3 and V4 are opened and all other valves are closed. Here, pump 26, 28 pushes spent dialysate through line 328 and valve V4 into the spent compartment 342 of single balance chamber 340. That action moves membrane 346, which pushes fresh dialysate from fresh compartment 344 back through valve V3 and line 330. Afterwards, all valves are closed for an instant. Then valves V2 and V3 are opened, enabling pump 22, 24 to push fresh dialysate into fresh compartment 344, forcing spent dialysate from compartment 342 to move through drain line 338 into one of the drain bags.

It is necessary in renal replacement therapies, such as hemodialysis to provide a bolus of fresh solution to the patient for various reasons. For instance, the patient may need a bolus or volume of fluid if the patient becomes hypovolemic (abnormally low volume of circulating blood) or hypotensive (low blood pressure). To provide a bolus of solution for system 300f, fresh dialysate pump 22, 24 expels a predetermined amount of fluid, while valves V3 and V4 are opened and all other valves are closed. The fresh dialysate travels through line 330, valve V3 and into fresh compartment 344 of balance chamber 340. That action causes membrane 346 to move and push fluid back through line 328 and valve 324 into effluent dialysate pump 26, 28. Afterwards, all valves are closed. Then, valves V1 and V4 are opened and effluent dialysate pump 26, 28 pushes used dialysate into spent chamber 342 of balancing chamber 340. That action causes membrane 346 to move, pushing fresh solution from fresh chamber 344 into the dialyzer. Since no ultrafiltration is removed in this cycle, the amount of fluid sent to the dialyzer represents a net gain or bolus of fluid for the patient. This process can be repeated as many times as necessary to provide a patient with an overall net gain in fluid, if needed.

Previous FIG. 21 also illustrates one embodiment for providing a bolus of fluid to the patient. Here, an additional line 352 and valve V6 are provided. To provide the bolus, valves V3 and V6 are opened, while valves V1, V2, V4 and V5 are closed. Fresh dialysate pump 370 causes fresh dialysate to fill through valve V3 into fresh chamber 344 of balance chamber 340. An equivalent amount of spent fluid is pushed via that action and membrane 346 out of balance chamber 340, through line 352 and valve V6 into line 314 and dialyzer 20, 30. Again, since no ultrafiltration is removed in this cycle, the fluid sent to dialyzer 20, 30 represents a net gain or bolus of fluid. It should be appreciated that spent or effluent dialysate, which is still sterile, is suitable for the purpose of providing a bolus of fluid to the patient.

In an alternative embodiment, system 300e of FIG. 21 can provide a bolus of solution by opening valves V1, V4 and V5. Valve V3 is closed. Fresh dialysate pump 370 pumps fresh dialysate into spent compartment 342. Then all valves are closed for an instant. Afterwards, valves V3 and V6 are opened and fresh dialysate pump 370 pumps dialysate into fresh compartment 344, forcing the fresh fluid in spent compartment 342 to flow through bolus line 352, valve V6 and line 314 into the dialyzer. System 300e is also restored to balancing mode.

A number of alternative embodiments may be used with systems 300a to 300f. Any of the dialyzers discussed herein, such as the single filter disclosed in U.S. Pat. No. 5,730,712, assigned to the assignee of the present invention, may be used. Furthermore, the single dialyzer discussed below in connection with FIG. 32 may also be used. Arterial line 44a in an embodiment includes an air sensor and clamp 54 for automatic blood rinseback. Additionally, any of the fluid preparation and recirculation embodiments discussed above may be implemented with the single balance chamber systems 300. Moreover, any of the alternative embodiments listed above for systems 10, 110, 210, etc., may be applicable to systems 300.

Systems 300a to 300f also include electrodes or contacts 354 and 356, which are used with an access disconnection sensor ("ADS"). ADS contacts 354 and 356 are incorporated respectively in arterial line 44a and venous line 44b. If one of the arterial or venous lines becomes disconnected from the patient, an electrical impedance is changed. The break of the loop is sensed, blood pump 48 is shut down and corresponding clamps are closed. An alternative mechanism for the detection of accidental needle disconnection is the use of a conductive blanket underneath the patient's access. Any spillage of blood changes the conductivity of the blanket, setting off an alarm and stopping the pumping of blood and dialysate.

Ultrafiltrate Control—Single Balance Tube

Figure 23:
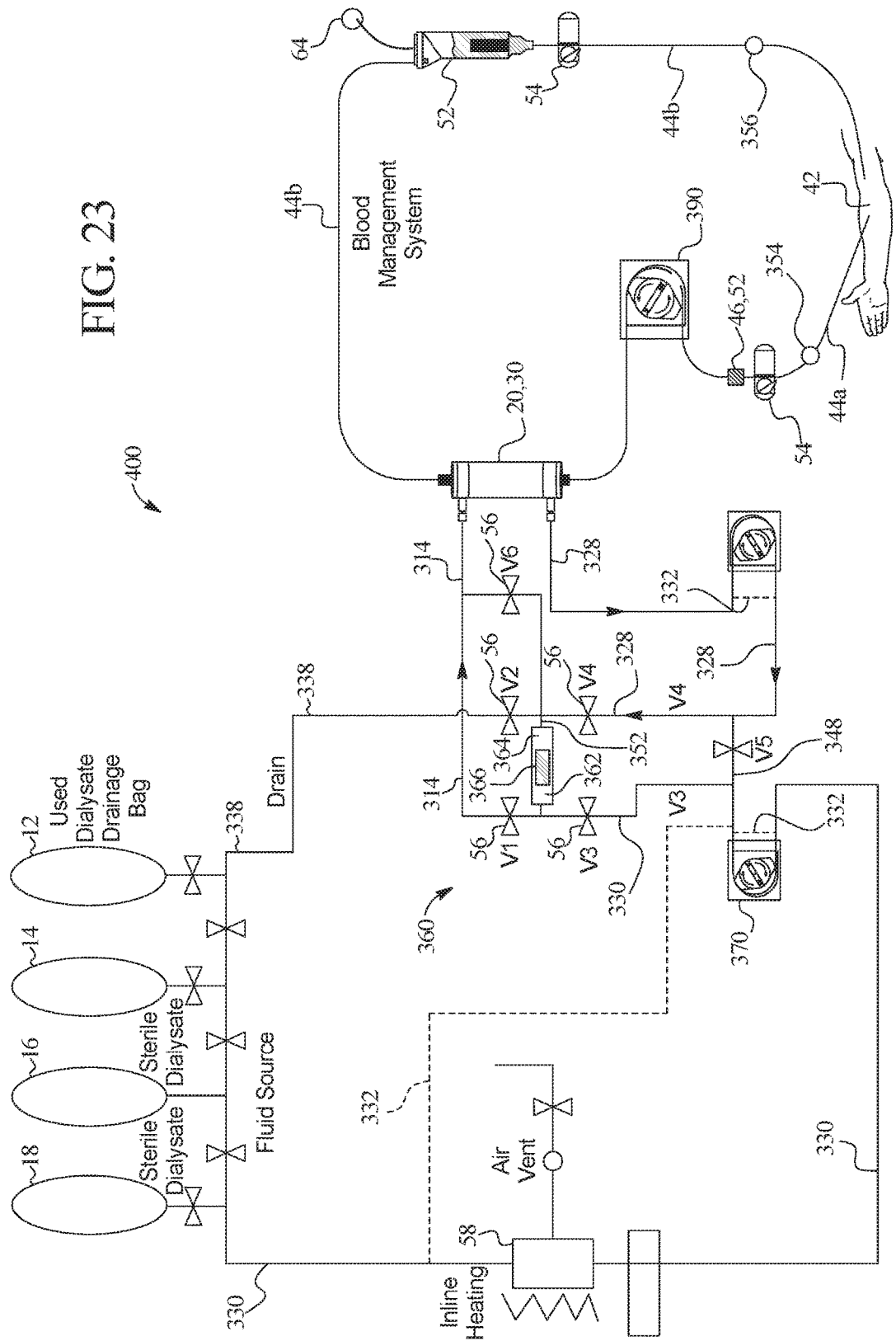
FIG. 23 is a schematic flow diagram illustrating various steps of one ultrafiltrate control method and apparatus employing a single balance tube.

The principles described above in FIGS. 17 to 22, covering systems 300, are applicable to different types of balancing apparatuses contemplated by the present invention. Each of systems 300 employs a single balance chamber 340. Referring to FIG. 23, an alternative system 400 employs an alternative balancing device 360. One embodiment for a balancing tube 360 is shown and discussed in more detail below in connection with FIG. 45. In general, balance tube 360 includes a cylindrical or otherwise tubular member. Inside such member resides a piston, ball or other separator 366 that fits snugly within the tube or cylinder. Balance tube 360 includes a tube or cylinder having a fresh portion 362 and a spent portion 364. Separator 366 fits snugly within the tube and moves back and forth between the fresh side 362 and spent side 364 of the tube.

System 400 of FIG. 23 is configured in a similar manner to system 300e of FIG. 21. Each component marked with an identical element number performs the same function and includes each of the same alternatives described above in system 300e. The primary difference between system 400 and system 300e as noted is the use of the balance tube 360 as opposed to balance chamber 340.

Valves V1 and V4 are opened, while valves V2, V3, V5 and V6 are closed for the pump to dialyzer or patient cycle in system 400. Spent dialysate pump 390 pumps effluent dialysate through line 328 and valve V4 into the spent side 364 of balance tube 360. That action causes separator 366 to move towards the fresh side 362 of balance tube 360 and push a like amount of fluid out through line 314 and valve V1 into dialyzer 20, 30 or directly to the patient (as before, system 400 of FIG. 23 is applicable to any of the modalities discussed herein).

In the pump to drain cycle, valves V2 and V3 are opened, while valves V1, V4, V5 and V6 are closed. Fresh dialysate pump 370 pumps fresh fluid through line 330 and valve V3 into the fresh side 362 of balance tube 360. That action causes separator 366 to move towards the spent side 364 of balance tube 360. A like amount of fluid is forced out of spent side 364, through drain line 338 and valve V2 to one of the drain bags.

For the ultrafiltration cycle of system 400, valves V2, V3 and V5 are opened, while valves V1, V4 and V6 are closed. Prior to this cycle, effluent dialysate resides within balance tube 360 and separator 366 is pushed all the way to the fresh side 362 of the balance tube 360. Next, spent dialysate pump 390 pulls effluent dialysate from the dialyzer or hemofilter through line 328, through ultrafiltrate line 348 and valve V5, through fill line 330 and valve V3 into the fresh side 362 of balance tube 360. That action causes separator 366 to move towards spent side 364, pushing an equal volume of fluid out through valve V2 and drain line 338 to one of the drain bags. Because the fluid sent to drain is matched with effluent dialysate from the dialyzer or ultrafilter, the fluid sent to drain constitutes fluid removed or ultrafiltered from the patient.

For a bolus of fluid to the patient, valves V3 and V6 are opened, while valves V1, V2, V4 and V5 are closed. In essence, no fluid can be drawn from the dialyzer or hemofilter. Instead, fresh dialysate pump 370 pumps fresh dialysate through line 330, through valve V3 and into the fresh dialysate side 362 of balance tube 360. Such action causes separator 366 to move towards side 364 of balance tube 360. A like volume of fluid is pushed from balance tube 360, through bolus line 352 and valve V6, through fill line 314 into dialyzer 20, 30 or directly into the venous line 44b. Because the fluid delivered to the dialyzer or patient is not matched with an amount of fluid removed from the dialyzer or hemofilter, the fluid delivered to the dialyzer or patient constitutes a net fluid gain or bolus for the patient. Such procedure is repeated as necessary until the patient receives a needed amount of fluid. Any of the alternative bolus embodiments described above in connection with FIG. 21 may also be used with system 400 and balance tube 360. Other features of balance tube 360 also applicable to system 400, such as end stroke sensors, are shown below in connection with FIG. 28.

Ultrafiltrate Control—Single Tortuous Path

Figure 24:
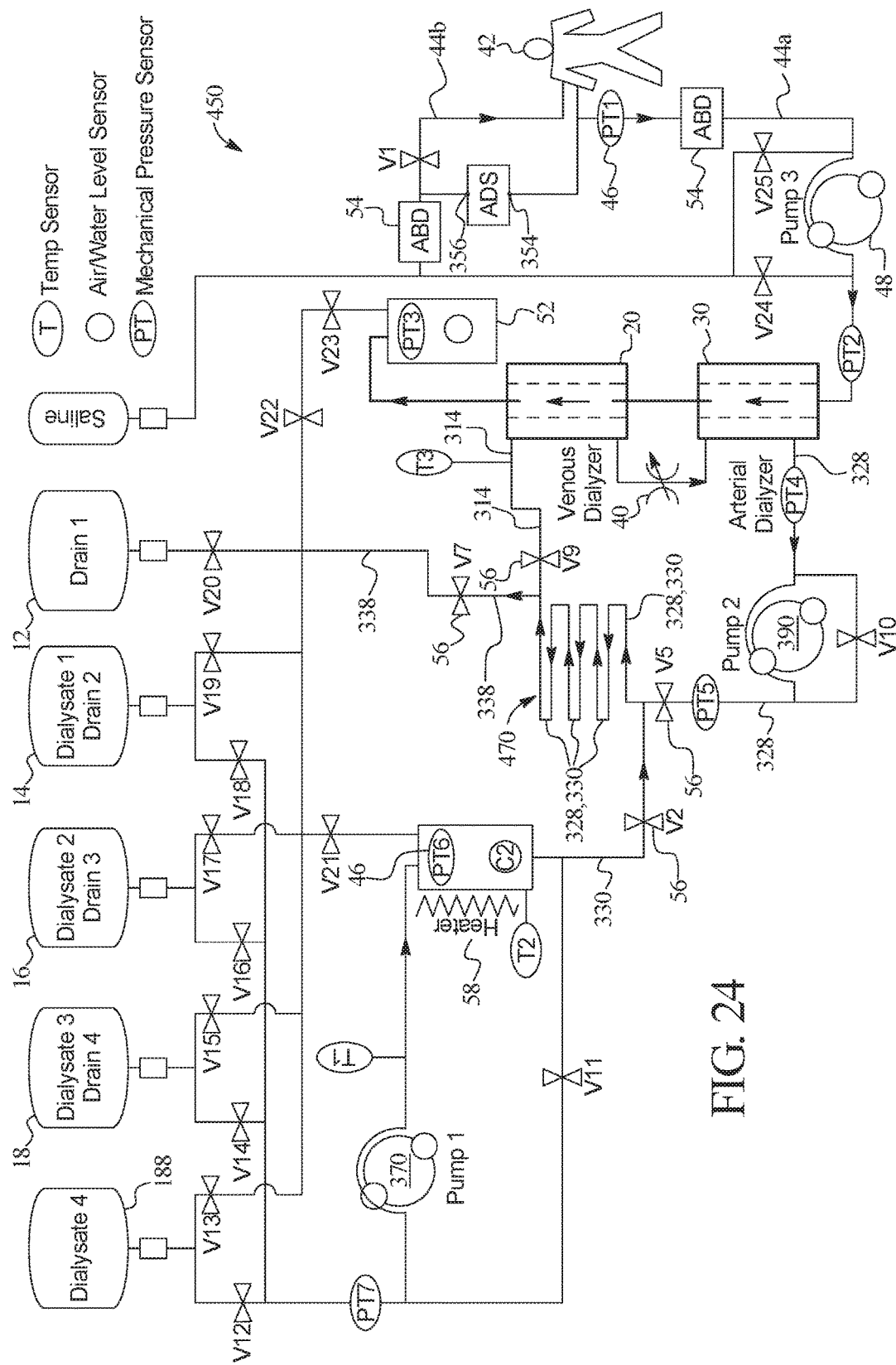
FIG. 24 is a schematic flow diagram illustrating one embodiment for controlling the volume of fluid exchanged with the patient and the volume of ultrafiltrate removed from the patient employing a single tortuous path.

Referring now to FIG. 24, a further alternative flow balancing device is illustrated by system 450. System 450 employs a single tortuous path 470. System 450 includes many of the same components described above, such as drain bag 12, supply bags 14 to 18, fresh dialysate pump 370, heater 58, spent dialysate pump 390 and blood pump 48. System 450 is shown in use with the ECHD dual dialyzers 20 and 30, separated by a variable restriction 40. It should be appreciated that system 450 may be operated with any of the modalities described herein. Other components with like element numbers are also shown.

The primary difference between system 450 and the previous single balance device systems is the use of a tortuous path 470 as opposed to a confined volume that is divided by a separator, such as a membrane or moving ball or piston. The advantage of system 450 is that to place tortuous path 470 in a cassette is relatively simple compared with either the volumetric membrane pumps or the balance chambers and tubes described above, which each require a flexible sheeting or membrane to be sonically welded, chemically adhered or otherwise fused to a rigid plastic cassette.

Tortuous path 470 as seen in FIG. 24 includes a combination of ultrafiltrate line 328 and dialysate input line 330. Fluid line 328,330 is sized to provide as best a bulk transport of fluid as possible, while attempting to minimize pressure drop. That is, a tortuous path 470 in an embodiment is a U-shaped, V-shaped or rectangular-shaped channel in the cassette, which is relatively long and thin or of a small diameter or cross section. The goal of tortuous path 470 is to allow one bulk infusion of fluid, such as fresh dialysate, to move a bulk of fluid already existing in the flow path to a desired place, such as spent dialysate to drain.

A drawback of tortuous path 470 of system 450 is the potential for fresh dialysate and spent dialysate to mix within the tortuous path as opposed to moving as bulk fluids. The configuration of the path is refined so that such mixing is minimized and occurs as much as possible only at the interface between the fresh and used dialysate, leaving the middle of the bulk of either fluid relatively unmixed and consistent. To this end, measures may be taken to maintain the flow of both fluids in either a laminar or turbulent state as desired to minimize mixing. For the online systems described herein especially, tortuous path 470 offers a viable solution, wherein the cost and complexity of a cassette or volumetric control system is reduced.

To perform the fill to dialyzer or patient cycle in system 450, fresh dialysate is pumped via dialysate pump 370 through line 330 and valve V2 up to closed valves V7 and V9. Next, valves V5 and V9 are opened, while valves V2 and V7 are closed. Spent dialysate pump 390 pulls effluent dialysate from arterial dialyzer 30 through line 328, valve V5, tortuous path line 328, 330 and up to valve V9. That bulk transport of fluid pushes the fresh dialysate residing within tortuous path line 328, 330 through valve V9, through fill line 314 and into venous dialyzer 20 or venous line 44b.

After the fill cycle takes place, tortuous path line 328, 330 is filled with effluent or spent dialysate. The drain cycle may then take place. Here, valves V5 and V9 are closed, while valves V2 and V7 are opened. Fresh dialysate pump 370 pumps fresh, heated dialysate through valve V2, line 330, through tortuous path line 328, 330 and up to the point of valve V9 or V7. That bulk transport of fluid in turn pushes spent dialysate through drain line 338 and valve V7 into one of the drain bags.

The ultrafiltrate cycle takes place as follows. With the tortuous path line 328, 330 filled with ultrafiltrate, valves V5 and V7 are opened, while valves V2 and V9 are closed. Spent dialysate pump 390 pulls fluid from arterial dialyzer 30 through line 328, valve V5 to fill tortuous path line 328, 330. That amount of fluid is then moved through valve V7, line 338, to drain. Because the amount of fluid moved to drain is matched at least substantially by effluent or spent dialysate, the patient experiences a net loss or ultrafiltration of fluid.

To provide a bolus of fluid to the patient, with the tortuous path line 328, 330 full of fresh or effluent fluid, valves V5 and V7 are closed, while valves V2 and V9 are opened. Fresh dialysate pump 370 pumps fresh dialysate through line 330 and fills tortuous path line 328, 330. A same volume or substantially the same volume of fluid flows through valve V9, fill line 314 and into venous dialyzer 20. Because the patient or dialyzer has received an amount of fluid without a corresponding amount of fluid being withdrawn from arterial dialyzer 30, patient 42 experiences a net gain or bolus of fluid.

Ultrafiltrate Control—Dual Balance Chambers

Figure 25:
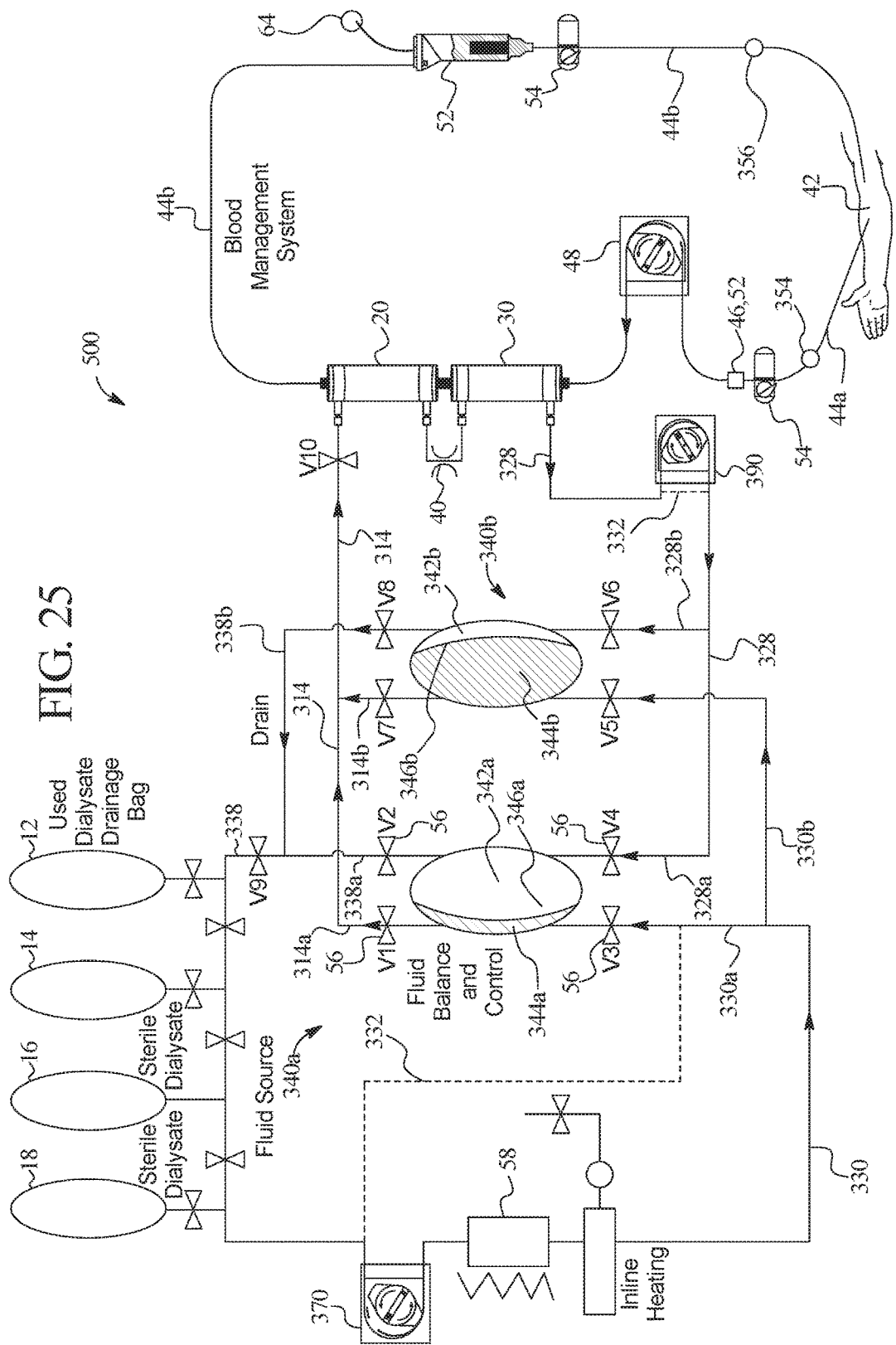
FIGS. 25 and 26 are schematic flow diagrams illustrating various features and advantages associated with an ultrafiltrate control method and apparatus that employs dual balance chambers.

One potential problem with the single balancing device embodiments just previously described is pulsatile flow. The single balancing device systems can compensate the pulsatile nature of the flow somewhat by slowing the flowrate of fresh fluid to the dialyzer relative to the flowrate of fluid from the dialyzer. Other solutions are provided by system 500 of FIG. 25 and other dual balance device systems shown below. These systems provide two balance chambers, two balance tubes or two tortuous paths that operate in parallel and at alternating cycles so that flow is delivered to the dialyzer or patient as it is being removed from the dialyzer or hemofilter. System 500 includes many of the same components described above, which are shown with like numbers that do not need to be re-described. Further, system 500 is shown in operation with the ECHD dual high flux dialyzers 20 and 30 and variable restriction 40. It should be abundantly apparent however from the previous descriptions that system 500 can operate with any of the modalities described herein.

System 500 includes first and second balance chambers 340a and 340b, which are each the same in one embodiment as balance chamber 340 described above in connection with FIGS. 17 to 22. Balance chambers 340a and 340b may be referred to herein collectively as a flow equalizer.

In the illustrated embodiment, dialysate pumps 370 and 390 are peristaltic pumps. They may alternatively be membrane pumps or other types of pumps described herein. Fresh dialysate pump 370 is shown upstream of heater 58, which is different from the single balance device configurations. Either configuration is possible for either of the single and double balance device systems. Further, each of the valves used in system 500 may be configured in a cassette or be any type of valve as discussed herein.

In a first exchange cycle, one of the balance chambers 340a or 340b fills with fresh solution and at the same time delivers an equal volume of spent dialysate to drain. In that same first cycle, the other balance chamber 340a or 340b fills with effluent dialysate and at the same time pushes a like volume of fresh dialysate to the dialyzer 20 or the patient according to the modality. Then, in a second cycle, the balance chambers 340a and 340b alternate functions so that the balance chamber that previously delivered fresh dialysate to the patient now delivers spent dialysate to drain, while the balance chamber that previously delivered spent dialysate to drain now delivers fresh dialysate to the dialyzer or patient.

Based on the foregoing description of the operation of balance chamber 340 in connection with FIGS. 17 to 22, it is not necessary to repeat the valve description for each of the balance chambers 340a and 340b of system 500. One important aspect to distinguish, however, is that there is a short dwell time at the end of each exchange cycle when all valves are closed to ensure that the two balance chambers 340a and 340b are in sync for the next cycle.

The flow equalizer or balance chambers 340a and 340b are used differently than in other systems employing a flow equalizer from the standpoint that there is not a separate UF removal device in system 500. That is, in other systems employing a flow equalizer or dual balance chambers, the balance chambers are dedicated to removing an amount of fluid from the dialyzer, while at the same time filling the dialyzer with a like amount of fluid. System 500, on the other hand, uses balance chambers 340a and 340b for that purpose and also to remove a net amount of fluid or ultrafiltrate from patient 42. The valve operation for removing a net loss or ultrafiltration of fluid from the patient includes opening valves V1, V2, V6, V7, and V9, while closing valves V3, V4, V5, V8 and V10. This valve configuration pushes effluent dialysate to drain by pushing the fresh dialysate from balance chamber 340b to balance chamber 340a.

The systems herein including system 500 having dual balancing chambers 340a and 340b enable an ultrafiltrate removal rate to vary over time, which is sometimes referred to as an ultrafiltrate profile. For example, if an ultrafiltrate cycle is typically performed after each five exchange cycles, one could change the rate at which ultrafiltrate is removed from the patient by increasing or decreasing the frequency of cycles. This could result, for example, in more fluid being removed during a first part of therapy than a second. In the present invention, the processor of the renal failure therapy machine may be configured to run an algorithm, which enables the patient to select a profile, a treatment time and an overall volume to be removed. The algorithm automatically calculates an ultrafiltrate frequency profile that achieves, according to the profile, an entered net cumulative ultrafiltrate volume over an entered treatment time. Those parameters may be entered through a patient data card or through a secure data connection.

System 500 can also provide a bolus of solution to the patient when needed. Valves V2, V3, V7, V8 and V10 are opened and valves V1, V4, V5, V6 and V9 are closed. Pump 370 is run forcing one balance chamber bolus of dialysate and/or substitution fluid to the dialyzer or patient.

In any of the embodiments described herein, it is important that the valves of the systems are checked to ensure that they open and close properly. In one embodiment, the valves are checked periodically throughout treatment using conductive sensing. That is, if fluid escapes from the system via a faulty valve or tear in a cassette membrane, conductive sensors that measure a flow of electricity across a liquid can send an alarm and trigger appropriate action. Further, with a cassette, temperature sensing may be employed, for example, by applying a thermistor, IR sensor or thermocouple on one side of the sheeting of the cassette. Here, the temperature sensor is attached to the blood therapy instrument and, for example, contacts the sheeting membrane so as to obtain a quick reading of the temperature of the dialysate.

Prime and Rinseback

Figure 26:
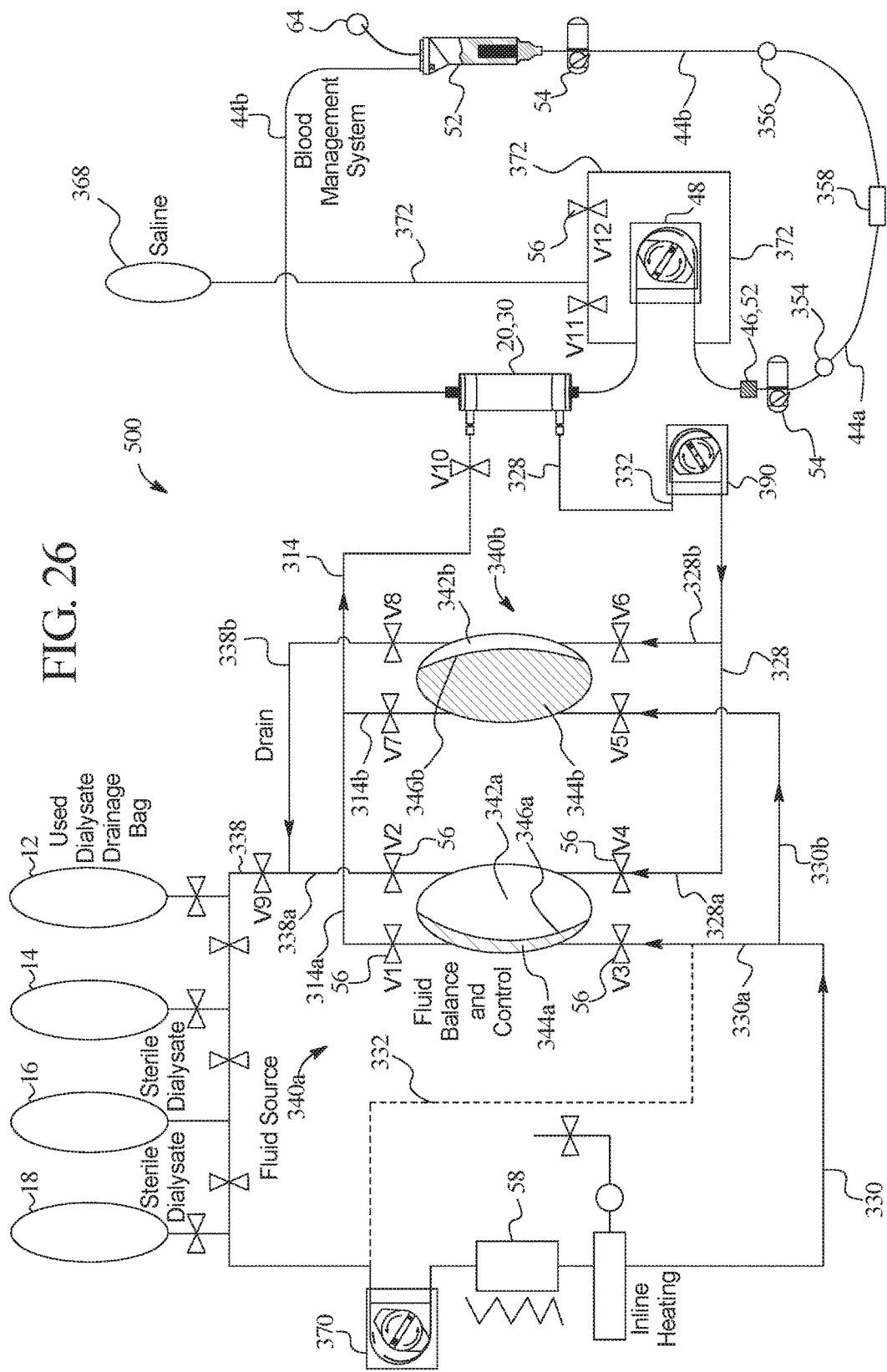

Referring now to FIG. 26, it is necessary to prime the extracorporeal circuits of the present invention with sterile solution prior to connecting patient access line 44*a* and venous access line 44*b* to the patient. To do so, the ends of the arterial and venous lines are connected together at connection 358. In one embodiment, fresh dialysate pump 370 and effluent dialysate pump 390 run and pump fluid through balance chambers 340*a* and 340*b* (or through any of the single or dual balance devices discussed herein) until dialysate or substitution fills the dialysate circuit. The blood therapy machine then enters a bolus mode. In one embodiment, blood pump 48 runs in reverse until venous drip chamber 52 fills with fluid. Excess air in the line and drip chamber vents through a transducer protector or vent 64 provided with or in communication with drip chamber 52. Transducer protector or vent 64 in one embodiment is a 0.2 micron hydrophobic membrane.

In the next step of this first priming method of the present invention, blood pump 48 runs in its operational direction until half the volume of the drip chamber is moved. Then, blood pump 48 runs in the reverse direction again until drip chamber 52 is again filled and vented. The pump then runs again in the normal operation direction enough to move half a drip chamber volume worth of fluid in the normal operating direction. In each cycle, dialysate or substitution fluid is back-filtered through dialyzer 20, 30 (or different filter for a different modality), adding to the total volume of fluid in the extracorporeal circuit over each cycle period. This first priming method cycles back and forth as described until the extracorporeal circuit is completely filled with dialysate or substitution fluid. It should be appreciated that this priming method applies to any of the modalities described herein, any of the pumping arrangements described herein and any of the volumetric control methods described herein.

In a second priming method, a separate saline or priming fluid bag 368 is connected to the extracorporeal circuit via saline line 372. In the illustrated embodiment, saline line 372 tees into the extracorporeal circuit at two places, upstream and downstream of blood pump 48. Valves V11 and V12 are positioned in saline line 372 so as to allow saline to flow selectively to one of or both of the teed connections upstream and downstream of blood pump 48. Arterial access line 44*a* is again connected to venous access line 44*b* via connection 358.

In the operation of the second priming method of the present invention, valve V11 located downstream of pump 48 is opened, enabling blood pump 48 to run in reverse and pump saline from bag 368, through saline line 372, through valve V11 through access line 44*a*, through connection 358, through access line 44*b*, and into drip chamber 52. Blood pump 48 pumps saline until drip chamber 52 is full and air is purged via vent 64. Next, valve V11 and air detector clamp 53 are closed and valve V12 is opened, enabling blood pump 48 to pull saline from bag 368 and push that volume of fluid in the normal operating direction downstream of pump 48, venting air through vent 64. This cycle continues until the extracorporeal circuit is fully primed. It should be appreciated that this second priming method is equally applicable to any of the modalities, pumping regimes, and volumetric control methods discussed herein.

Modifications to either of the first and second priming methods can also be made to provide a blood rinseback to patient 42. this is done at the end of therapy to return any blood in the extracorporeal line to the patient. The primary difference for blood rinseback is that access lines 44*a* and 44*b* are connected to patient 42 instead of to each other via connection 358. For example, using saline 368 or other suitable source, valve V11 is opened and pump 48 runs in reverse to rinseback blood to the pre-pump portion of arterial line 44*a*. An air detector 54 in that portion of arterial line 44*a* detects any air in the blood or saline and clamps the circuits if such air is detected. Pump 48 runs for an appropriate amount of time to ensure that blood has been fully rinsed back to the patient through the pre-pump portion of arterial line 44*a*.

Next, valve V11 closes and valve V12 opens, enabling pump 48 to pull saline from supply 368 and operate in the normal direction. Pump 48 pumps saline or other suitable fluid from source 368 through the remaining portion of arterial line 44*a*, through dialyzer 20, 30 (depending on modality) and through venous line 44*b* including drip chamber 52. The rinseback returns blood from those portions of the extracorporeal circuit to patient 42. In an embodiment, saline sensors on the arterial and venous lines 44*a* and 44*b*, respectably, cause an alarm if the extracorporeal circuit is not clear or transparent after a preset amount of rinseback. After blood is fully rinsed back to the patient, the patient is instructed to disconnect from the renal failure therapy system of the present invention.

The first priming method described above may also be adapted for blood rinseback. Here either dialysate or saline is back-filtered through the dialyzer or other modality filter. Blood pump 48 is run in the reverse and forward cycles described above in connection with the first priming method. Pump 48 may be run at a slower speed for blood rinseback so as to limit an amount of mixing between saline and blood. The saline or other solution needed to fully rinseback the blood to the patient is thereby minimized.

In an alternative method for priming system 500 or rinsing back blood to the patient, one of the line clamps 54 in the extracorporeal circuit is closed and saline or dialysate is pumped via one or both dialysate pumps 370 and 390 into the extracorporeal circuit until drip chamber 52 fills to a preset level, such as ¾ full. After the drip chamber 52 is filled to the preset level, the dialysate or saline infusion is stopped, and pumps 370 and 390 no longer pump fluid into the extracorporeal circuit. Then, line clamp 54 is opened. Blood pump 48 circulates the dialysate through the extracorporeal circuit. If needed, line clamp 54 may be clamped again to repeat the process.

In a further alternative prime or rinseback embodiment, saline bag 368, dialysate from a supply or drain bag, saline line 372, valve V12 and the portion of line 372 leading to the extracorporeal circuit between clamp 54 and blood pump 48 are used. Here, valve V11 in FIG. 26 is not needed. Dialysate or saline is pumped via one or more of the dialysate pumps 370 and 390 through dialyzer 20,30 with blood pump 48 running in the reverse direction and valve V12 closed so as to prime or rinseback the arterial line 44a. Then, valve V12 is opened and saline or dialysate is pulled from supply bag 368 with pump 48 running in the normal operating direction to prime or rinseback venous line 44b. This method uses dialysate or saline pumped through the dialysate circuit as well as a dialysate or saline source running directly to the extracorporeal circuit. This embodiment eliminates valve V11 shown in system 500.

It should be appreciated that each of the forgoing methods of prime and rinseback may be used in any of the forgoing modalities, pump configurations and volumetric control schemes. Further, those of skill in the art may be able to determine additional valving operations to achieve an effective prime and rinseback using the apparatuses and methods of the present invention.

Ultrafiltrate Control—Dual Balance Tube

While the present invention sets forth multiple embodiments for balancing devices, it is believed that the balancing tubes provide a good trade-off between ease of manufacturing, cost and effectiveness. The balancing chambers shown previously for example in FIGS. 25 and 26 are time-tested and proven to effectively meter and control ultrafiltrate in blood kidney failure therapies, such as hemodialysis. The sheeting and chambers associated with balance chambers, while certainly manufacturable, present a more complicated cassette than simply one having valve chambers, tubing for peristaltic pumps and tubes for the balance tubes of the present invention.

The tortuous path embodiment, while perhaps involving the simplest cassette, may not be as desirable with respect to efficient use of fresh dialysate (due to the tendency of the fresh and effluent dialysates to mix). Again, this potential drawback is not as much of a concern when dialysate is made online. The balance tubes may offer the best solution however for home use with fresh dialysate bags.

Referring to FIGS. 27A to 27D, different flow cycles pertinent to volumetric control of dialysate using dual balance tubes are illustrated. It should be appreciated that the layout of valves V1 to V10 with respect to balance tubes 360a and 360b is the same as the layout of valves V1 to V10 with respect dual balance chambers 340a and 340b in FIGS. 25 and 26. One can therefore readily visualize balance tube 360a being used in place of balance chamber 340a and balance tube 360b being used in place of balance chamber 340b in FIG. 25.

The cycle shown in FIG. 27A is a first dialysate exchange cycle. Here, valves V1, V4, V5, V8, V9, and V10 are open while valves V2, V3, V6 and V7 are closed. At the start of this cycle balance tube 360a is filled with fresh dialysate and separator 366a is located at least substantially at the end of spent portion 364a. Also, balance tube 360b is filled with effluent dialysate and separator 366b is located at least substantially at the end of fresh portion 362b of balance tube 360b. In this first cycle, fresh dialysate pump 370 pumps fresh dialysate through line 330, line 330b and valve V5 into fresh dialysate portion 362b of balance tube 360b. The force of fluid entering fresh portion 362b pushes separator 366b, which in turn pushes spent dialysate through open valve V8, line 338b, manifold 338 and valve V9 to one of the drain bags.

At the same time spent dialysate pump 330 pushes effluent dialysate from a dialyzer or hemofilter through manifold 328, line 328a, valve V4 and into the spent portion 364a of balance tube 360a. The force of fluid entering spent portion 364a of balance tube 360a causes separator 366a to move towards the fresh portion 362 of balance tube 360a. In turn, fresh dialysate is pushed through valve V1, line 314a, manifold 314 and valve V10 to a dialyzer or the extracorporeal circuit, depending on the modality used. It should be appreciated from the valving description of FIG. 27A that one of the balancing chambers is metering fresh fluid to the patient, while the other balancing chamber is metering spent fluid to drain.

Figure 27B:
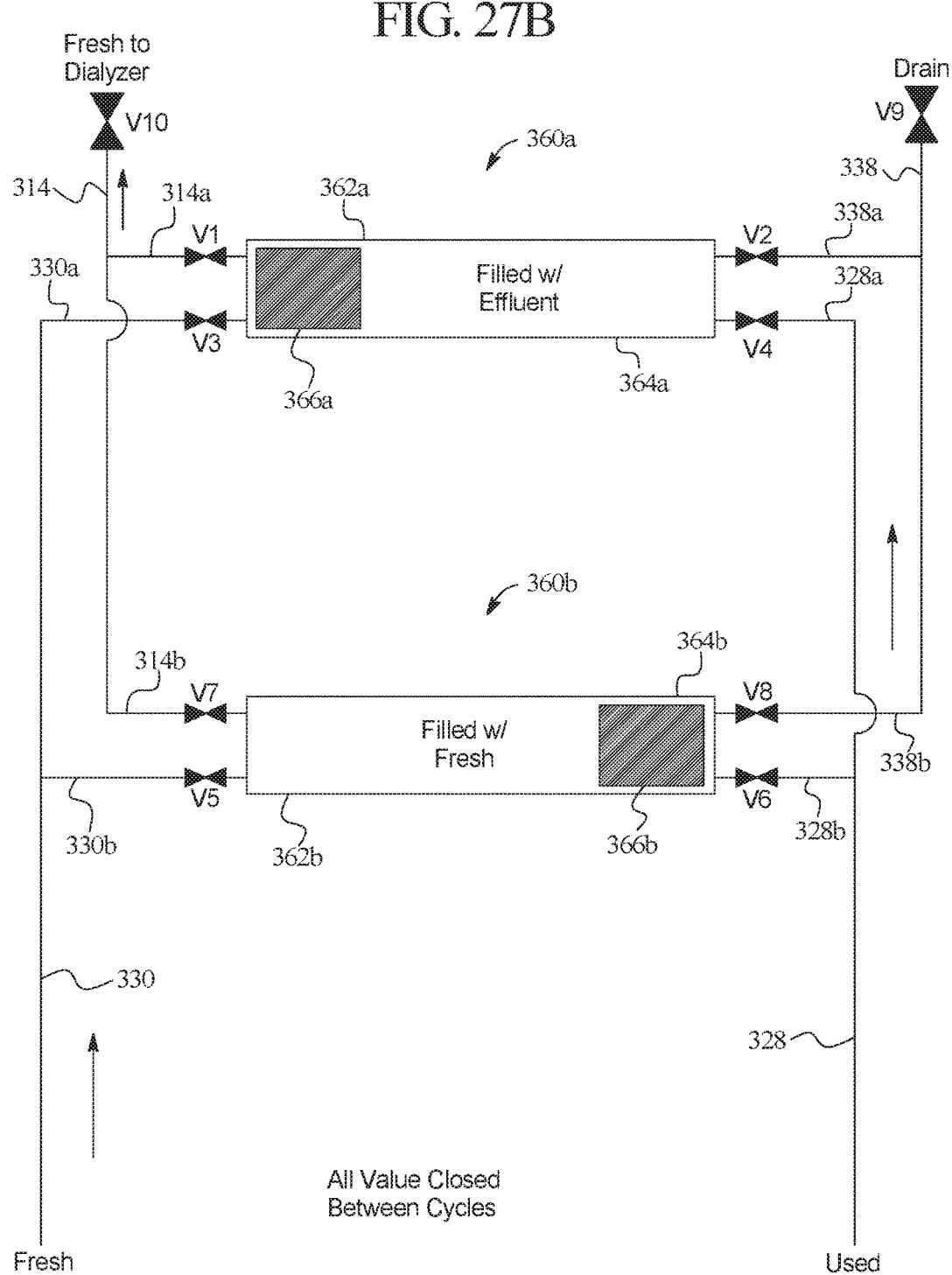

FIG. 27B shows separators 366a and 366b at the fresh end 362a and spent end 364b of balance tubes 360a and 360b, respectably (at the end of travel of the cycle shown in FIG. 27A). At this moment all valves V1 to V10 are closed. The all valves closed sequence ensures that balance tubes 360a and 360b and valves V1 to V10 are in sync for the next fluid transport cycle.

Referring now to FIG. 27C, an opposite fluid transport cycle of that shown in FIG. 27A is illustrated here beginning from the valve conditions shown in FIG. 27B, namely, with balance tube 360a filled with effluent dialysate and balance tube 360b filled with fresh dialysate. The opposite flow now occurs in which balance tube 360a meters spent fluid to drain, while balance tube 360b meters fresh fluid to the dialyzer or extracorporeal circuit. In this cycle, valves V2, V3, V6, V7, V9, and V10 are open, while valves V1, V4, V5 and V8 are closed. Fresh dialysate pump 370 pumps fresh dialysate through manifold 330, line 330a and valve v3 into the fresh portion 362a of balance tube 360a. Such action causes separator 366a to push spent dialysate through valve V2, line 338a, manifold 338 and valve V9 to drain. At the same time, spent dialysate pump 390 pumps spent dialysate from a dialyzer or hemofilter through manifold 328, line 328b, valve V6 and into the spent or effluent portion 364b of balance tube 360b. Such action causes separator 366b to push fresh dialysate through valve V7, line 314b, manifold 314 and valve V10 to the patient or dialyzer.

After the cycle of FIG. 27C is completed each of the valves closes with the balance tubes in the same state shown in FIG. 27A, so that the above three cycles shown in FIGS. 27A and 27C can be repeated. It should be appreciated that the all valves closed state of FIG. 27B occurs for a relatively short period of time, so that the flow of fluid to the patient or dialyzer and from the dialyzer or hemofilter is substantially non-pulsatile. Such non-pulsatile flow is advantageous versus the relatively pulsatile flow of the single balance device systems because (i) treatment is administered more efficiently and (ii) the fresh and spent pumping cycles may be carried out at the same speed reducing the risk of pulling too much fluid from the patient.

Figure 27D:
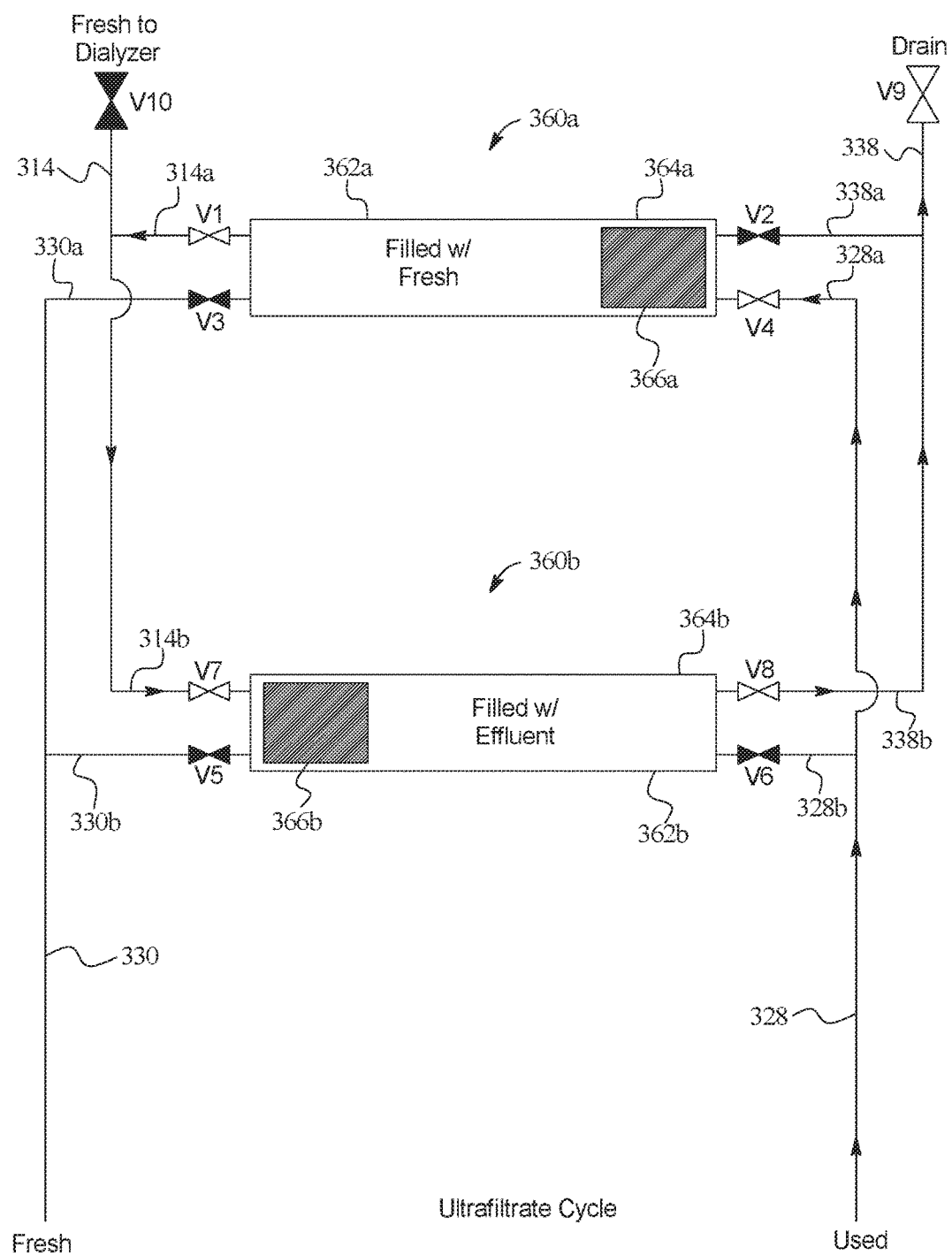

Referring now to FIG. 27D, one embodiment for performing ultrafiltration with the dual balance tubes 360a and 360b of the present invention is illustrated. It should be appreciated that the state of separators 366a and 366b and the fluids held within balance tubes 360a and 360b is the same as in FIG. 27A. Instead of performing the exchange cycle, however, the valve arrangement shown in FIG. 27D is employed. Here, valves V1, V4, and V7 to v9 are opened, while valves V2, V3, V5, V6 and V10 are closed. In the ultrafiltration cycle only used dialysate pump 390 is run. Pump 370 may stop or run through recirculation line 332. Pump 390 pumps effluent fluid through manifold 328, line 328a and valve V4 to push separator 366a from spent portion 364a of balance tube 360a towards fresh portion 362a of the tube. That action causes fresh dialysate through valve V1, line 314a, manifold 314, line 314b and valve V7 into balance tube 360b. Fluid entering balance tube 360 in turn pushes separator 366b, forcing effluent fluid through valve V8, line 338b and manifold 338 to drain through valve V9. The fluid sent to drain represents ultrafiltrate because during that cycle no corresponding amount of fluid is sent to the patient or dialyzer.

This ultrafiltrate cycle may be varied in frequency relative to the fluid exchange cycles to vary the rate of ultrafiltrate removal over time. It should be appreciated that a bolus of fluid may be given to the patient in a similar manner, with incoming fresh dialysate pushing effluent dialysate via a separator from one balance tube to the other, forcing the separator in the other balance tube to push fresh solution towards the dialyzer or extracorporeal circuit depending on modality. The patient or dialyzer gains fluid without a corresponding loss of fluid from the patient, resulting in a bolus of fluid.

Figure 28:
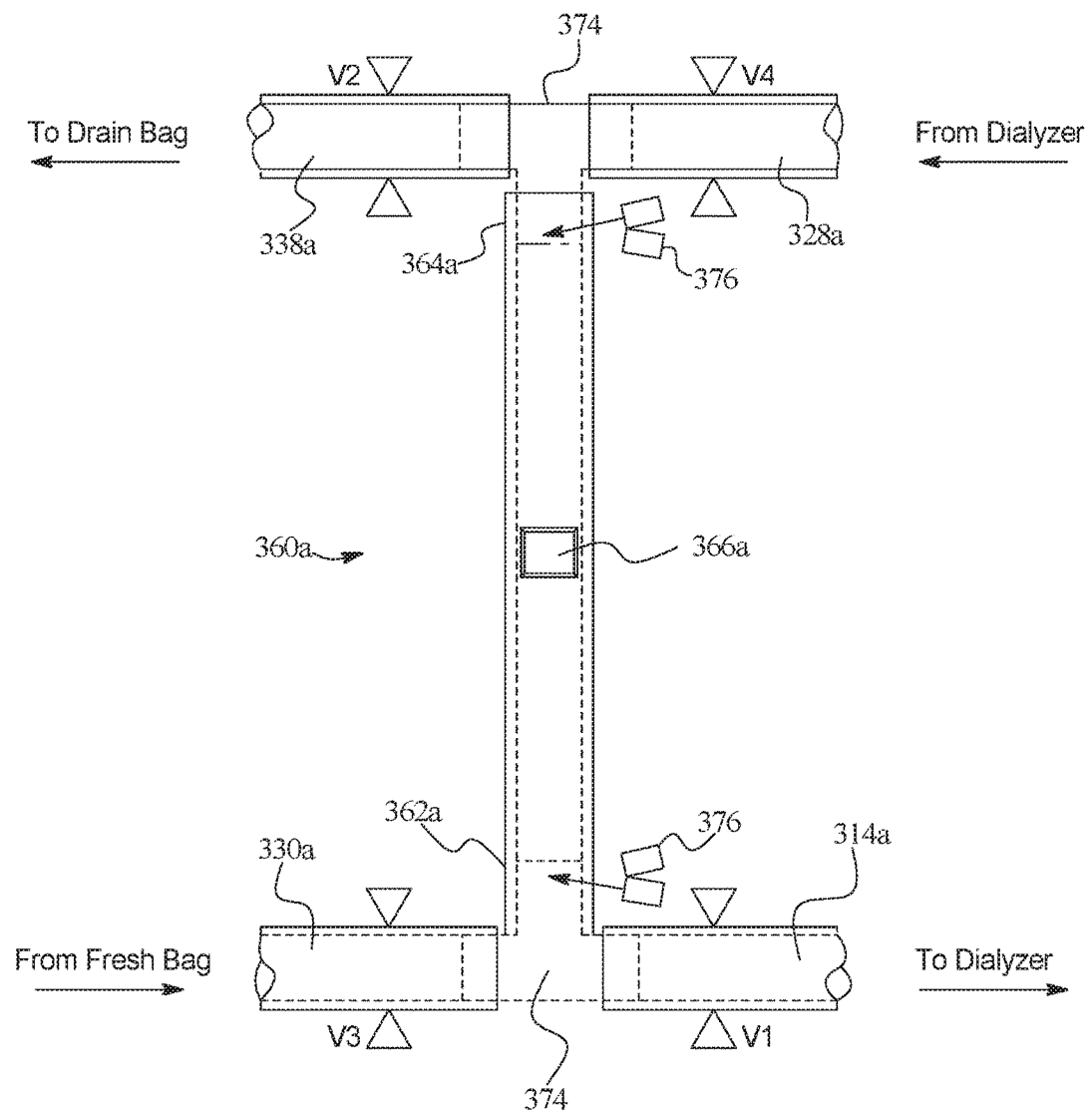
FIG. 28 illustrates one alternative valve arrangement for the balance tube volume control device of the present invention.

Referring now to FIG. 28, an alternative valve configuration for balance tube 360a of the present invention is illustrated. Here, a pair of tees 374 are mated or sealed to the ends 362a and 364a of balance tube 360a. Valves V1 to V4 are placed in the same configuration relative to the inlets and outlets of tube 360a shown in FIGS. 27A to 27D. Here, only one pathway to each end 362a and 364a of balance tube 360a is needed. As in FIGS. 27A to 27D, valve V2 controls whether effluent dialysate is delivered to the drain or the drain bag through line 338. Valve V4 controls whether effluent dialysate from the dialyzer or hemofilter enters balance tube 360a through line 328a. Valves V2 and V4 are both located at the spent dialysate end 364a of balance 360a. Valve V3 controls whether fresh dialysate from one of the supply bags enters balance tube 360a through line 330a. Valve V1 controls whether dialysate leaves balance tube 360a through line 314a. Valves V1 and V3 are both located at the fresh dialysate end 362a of balance 360a.

FIG. 28 also illustrates that a pair of sensors 376, such as optical sensors, are positioned in the instrument so as to detect and ensure that separator 366a has traveled to the appropriate end 362a or 364a of balance tube 360a. For example if fluid is expected to be received from the dialyzer through line 328a and V4, the logic in the renal failure therapy machine will expect to see a beam of light of the sensor 376 at end 362a broken and then reestablished once separator 366a passes sensor 376 and reaches the end of its stroke. If the beam of light is either not broken or not reestablished the machine knows that separator 366a has not traveled to its appropriate destination for the given cycle and sends an appropriate signal. Alternative sensors, such as proximity, capacitance, Hall Effect, ultrasound or others may be employed instead of the illustrated optical sensors 376. These sensors may also be employed to check valve function. Here, if separator 366a moves due to a valve being open when that valve is supposed to be closed, the valve is detected to have a leak.

Ultrafiltrate Control—Dual Tortuous Path

Figure 29:
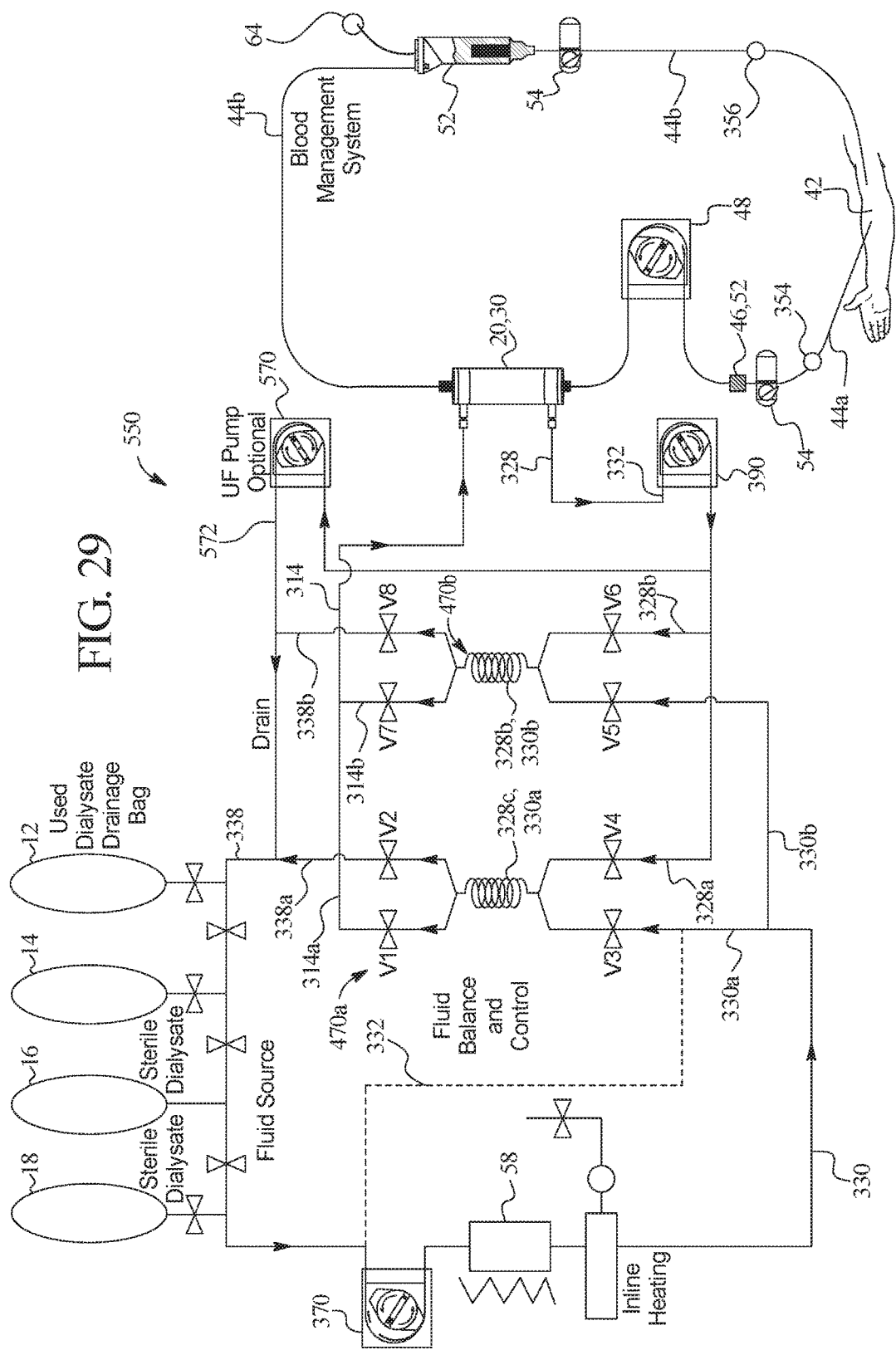
FIG. 29 is a schematic flow diagram illustrating yet another embodiment for controlling the volume of ultrafiltrate removed from the patient, which includes dual tortuous paths.

Referring now to FIG. 29, another dual balance device embodiment is illustrated. Here the balance chambers and balance tubes shown previously in FIGS. 25 to 28 are replaced by a pair of tortuous paths 470a and 470b. Tortuous paths 470a and 470b are placed in between valves V1 to V8 as seen also in FIGS. 25 and 26. Indeed, the operation of valves V1 to V8 in FIGS. 25, 26 and 29 operate identically to continuously send fluid to the patient, send spent fluid to drain and remove ultrafiltrate from the dialyzer or hemofilter. As before, the dual tortuous paths 470a and 470b may be implemented with any modality and with any of the different types of pumps described herein. To push fresh fluid to dialyzer 20, 30, tortuous path line 328a, 330a or line 328b, 330b is filled with fresh dialysate. Either valves V1 and V4 for tortuous path 470a or valves V6 and V7 for tortuous path 470b are opened. Pump 390 pumps spent dialysate through either line 328a, 330a or line 328b, 330b to push the corresponding bulk of fresh dialysate to the dialyzer. Then either valves V2 and V3 or valves V5 and V8 are opened to push spent fluid to drain.

In one preferred embodiment, the tortuous paths 470a and 470b are alternated so that one path delivers dialysate to the dialyzer during one cycle and the other tortuous path delivers dialysate to the dialyzer during the same cycle. The roles of paths 470a and 470b are then reversed. While one path is delivering dialysate to the dialyzer, the other is filling with fresh solution and delivering spent dialysate to drain. Each of the tortuous paths 470a and 470b is built to have a length and diameter that attempts to minimize the amount of mixing between fresh and spent fluids, so that the fluids tend to move in bulk to their desired destination.

To remove ultrafiltrate, fresh fluid from one line 328a, 330a or 328b, 330b can be moved to in turn displace spent fluid from the other line to drain. For example, valves V1 and V4 of tortuous path 470a may be opened so that spent dialysate enters line 328a, 330a and displaces fresh dialysate through open valve V7 into line 328b, 330b of tortuous path 470b. Valve V6 is opened and spent dialysate is moved through line 572 to drain. If needed, a valve may be added after dialysate pump 390 so that spent fluid does not flow back into pump 390 during the ultrafiltrate cycle.

As illustrated, a separate ultrafiltrate pump 570 may be added to system 550 or to any of the forgoing systems. Ultrafiltrate pump 570 enables tortuous paths 470a and 470b to operate continuously to send fluid to and take equal amounts of fluid from the dialyzer or hemofilter. The ultrafiltrate pump 570 removes dialysate through ultrafiltrate line 572 to one of the drain bags. It is believed that removing the ultrafiltrate function from the tortuous paths 470a and 470b may reduce mixing of the fresh and spent fluids. The additional ultrafiltrate pump 570 can also be run in reverse with pump 390 to provide a bolus of fluid to a patient in need same.

It should appreciated that any of the dual balancing device systems described herein can employ the ADS contacts 354 and 356 and associated electronics to detect when one of the access lines 44a or 44b is inadvertently disconnected from the patient during treatment. Further, any system can employ one of more of the various pressure reliefs 332 shown in FIGS. 25, 26 and 29 and described previously. Furthermore, the heater may be placed before or after fresh dialysate pump 370. Again the pumps may be of any of the varieties described herein. Moreover, any of the dual balance device systems may be used with any of the fluid preparation modules described above as well as the recirculation loops. The systems may also employ noninvasive temperature measuring devices to measure the temperature of fluid within a disposable cassette.

Ultrafiltrate Control—Weight Scales

Figure 30:
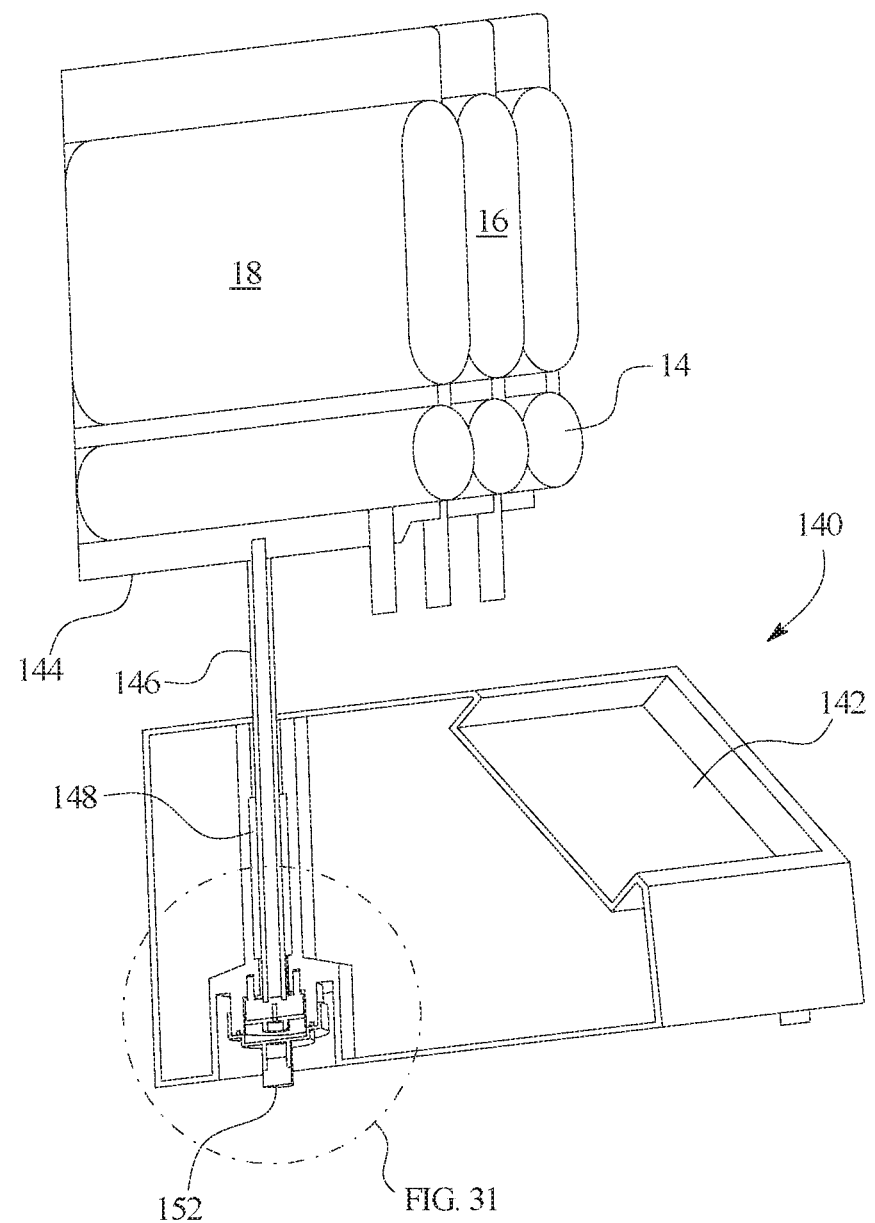
FIGS. 30 and 31 illustrate yet a further alternative embodiment for controlling the amount of fluid that has been exchanged with and the amount of ultrafiltrate removed from the patient, which includes a weight measurement system.
Figure 31:
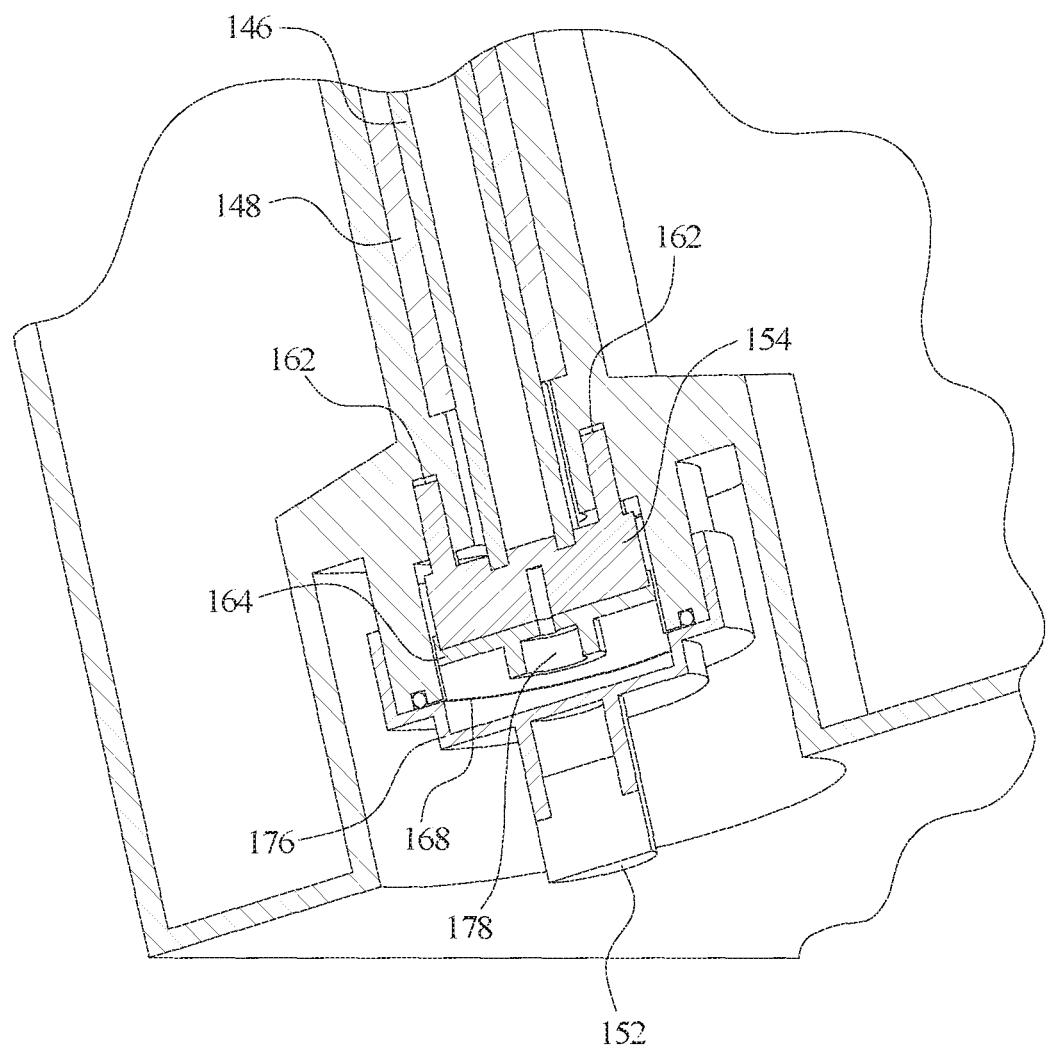

Referring now to FIGS. 30 and 31, a further alternative method of controlling the amount of dialysate exchanged and ultrafiltrate removed is to do so by measuring the weight of fluid within supply and drain bags 12 to 18. For convenience only supply/drain bags 14, 16, and 18 are shown in FIG. 30. It is well known to use weight to control a renal failure therapy process. A single scale can be employed that accounts for both fresh fluid lost and spent fluid gained. Here, because a net volume of fluid is removed or ultrafiltered from the patient, the system expects to see an increase in weight over time. Alternatively, a first scale for the fresh bags and a second scale for the drain bags are used. Two signals are produced and summed to determine the amount of ultrafiltrate accumulated for any give point in time. The system of FIGS. 30 and 31 uses a single scale, however, the dual scale approach may be used instead.

The import of FIGS. 30 and 31 is to show one apparatus by which a scale or weight measuring device may be implemented into the various systems described herein. In FIG. 30, a blood treatment machine 140 is illustrated. In the illustrated embodiment, blood machine 140 accepts a cassette at cassette loading portion 142, which is on a front, angled part of machine 140. Other embodiments of a machine that can accept a disposable cassette and employ a scale are shown below in FIGS. 35 to 39. Bags 14, 16 and 18 are loaded onto stand 144. Stand 144 is coupled to a shaft 146.

FIG. 31 shows an enlarged view of the cutaway in FIG. 30 and that shaft 146, stand 144 and the bags are supported by a foot 152 that rests on a table of wherever machine 140 is placed for treatment. Shaft 146 is movable linearly within a linear bearing 148. A cap 154 having a plurality of anti-rotation pins 162 is fitted to the end of movable shaft 146. Pins 162 reside within mating slots or grooves defined in the housing of machine 140. Pins 162 and the mating slots or grooves enable shaft 146 to move linearly but not rotationally with respect to machine 140.

A seat 164 seals one end of a rolling diaphragm 168 between the seat and cap 154. A housing 176 coupled to foot 152 and the machine frame seals the other end of rolling diaphragm 168 between housing 176 and the frame of machine 140. Housing 176, rolling diaphragm 168 and seat 164 form a closed volume chamber. The rolling diaphragm enables the volume to remain closed and also enables shaft 146 to fluctuate up and down due to the varying weight within the supply end drain bags. The rolling diaphragm 168 may be made of any suitable deformable but impermeable material, such as rubber or plastic sheeting. The volume of air within the closed volume chamber pressurizes due to the weight of the bags 14 to 18 and supporting apparatus. The amount of pressure indicates or varies with the amount of liquid in bags 14 to 18.

A pressure sensor, which may be any suitable type of sensor (not illustrated), is provided for example within opening 178 defined by seat 164. The pressure sensor senses the amount of pressure within the closed volume chamber. The sensor sends a signal to a processor or a controller within machine 140, which processes that signal and determines the corresponding weight in bags 14 to 18.

The weight control system is desirable because it removes the need for the volumetric control devices described above. The cassette for machine 140 is much simpler, including mainly valve flow paths. One disadvantage of the weight system is that it requires the patient to load the bags properly onto stand 144. The stand and assembly described in connection with FIGS. 30 and 31 may also add weight and size to the overall device. The home renal failure therapy machine of the present invention is desirably small and light, so that a person can travel or maneuver the device easily within or outside of the home.

ECHD Filter

Figure 32:
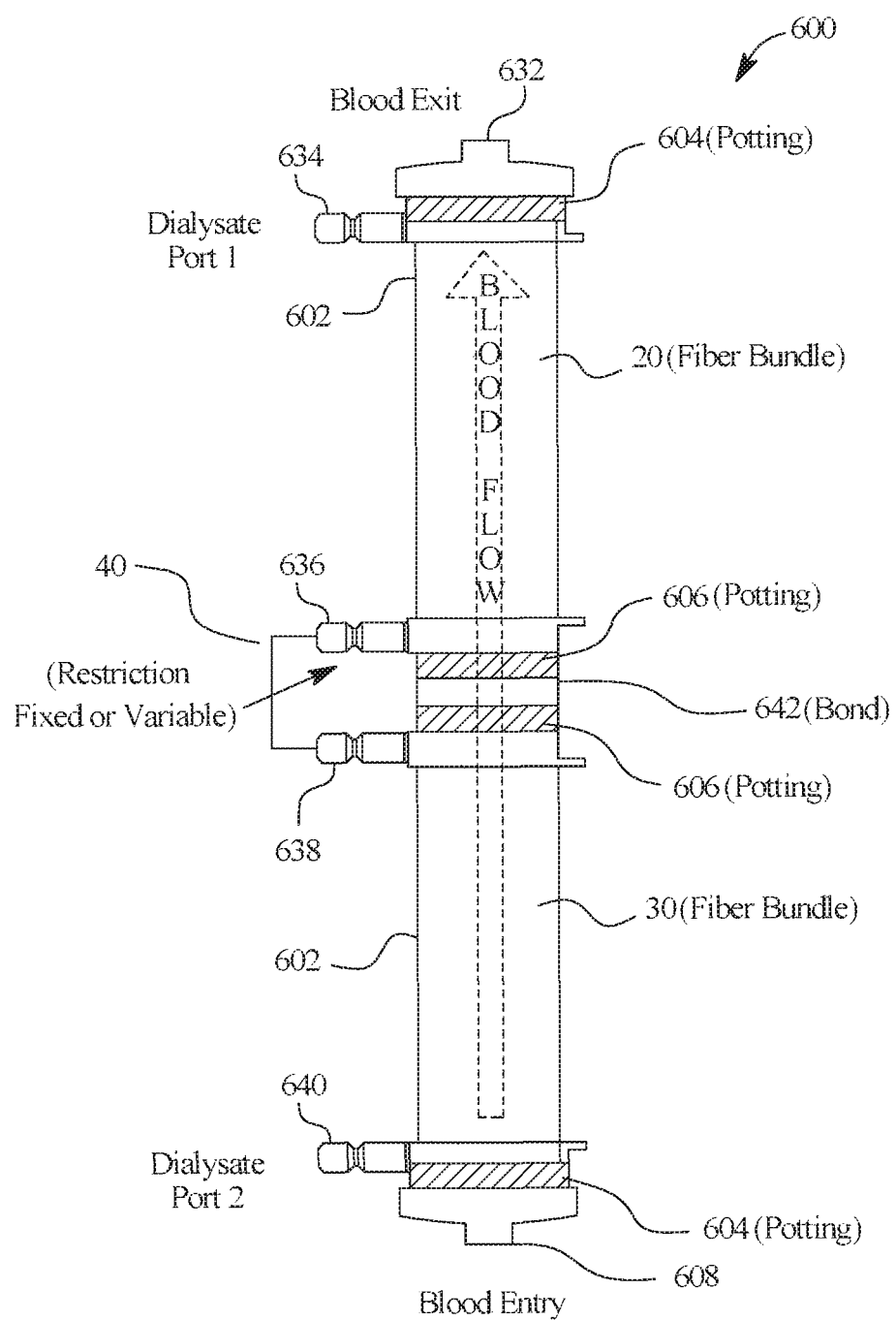
FIG. 32 is an elevation view of one embodiment of an enhanced convection of hemodialysis filter of the present invention.

Referring now to FIG. 32, one embodiment for an ECHD filter is illustrated by filter 600. As incorporated above, one suitable ECHD filter is described in U.S. Pat. No. 5,730,712, assigned to the assignee of the present invention. Filter 600 like the filter described in the patent is provided in a single unit. Filter 600 however differs from the one in the patent in that it allows for operation with a variable restriction 40.

Filter 600 includes a housing 602 corresponding to venous dialyzer 20 and a housing 602 corresponding to arterial dialyzer 30. Housing 602 may be made of any suitable material, such as a cylindrical, rigid plastic. Fibrous, semi-permeable membranes are loaded within the venous section 20 and the arterial section 30. Those membranes are potted at the outside ends of housings 602 via a potting 604 according to any method known to those of skill in the art. The membranes are potted at the inside ends of each of the venous 20 and arterial 30 sections of filter 600 via a potting 606.

A blood entry cap 608 is fixed in a sealed manner to housing 602 so that blood may enter cap 608 via a blood tube, be dispersed within the cap and enter the inside of the hollow semi-permeable fiber membranes of arterial section 30. At the same time, blood is blocked from entering housing 602 on the outside of hollow fiber membranes via potting 604.

Blood travels through filter 600 via the arrow shown in FIG. 32. That is, blood travels upward through the arterial portion 30 of filter 600 and out internal potting 606 of the arterial portion 30. Blood then enters intermediate chamber 642. The intermediate chamber 642 is a band or outer tube that is secured sealingly to the internal ends of housings 602.

Blood then enters the second set of hollow semi-permeable membranes housed within venous portion 20 of filter 600. The blood enters those fibers and is prevented from entering housing 602 of venous portion 20 outside the fibers via internal potting 606 at the internal end of housing 602 of venous portion 20. Blood flows through the venous portion of the membranes, through an outer potting 604 and into a blood exit cap 632. Blood exit cap 632 in turn couples sealingly to a tube that carries the blood away from filter 600 within the extracorporeal circuit.

Housing 602 of venous portion 20 includes a dialysate entry port 634 and a dialysate exit port 636. Likewise, housing 602 of arterial portion 30 includes a dialysate inlet port 638 and a dialysate exit and ultrafiltrate port 640. Ports 634, 636, 638 and 640 may be of any suitable type for mating sealingly with a medical fluid tubing. Port 634 receives dialysate from the dialysate supply. Port 640 enables dialysate and ultrafiltrate from the patient to be pulled out of filter 600. The effluent dialysate stream exists filter 600 via port 640.

Variable restriction 40 is placed in fluid communication with ports 636 and 638. The restriction may be made more or less restrictive so as to backfilter greater or lesser amounts of fresh dialysate into the hollow fiber membranes located in housing 602 of venous portion 20. As described above, the clearance of filter 600 is convective and diffusive. Filter 600 achieves one desired goal of the present invention, namely, to provide an overall effective treatment of small, middle and large molecules of a patient's waste via both convective and diffusive clearance modes. Housings 602, caps 632, 608, the potting material, the porous fibers and the ports may be made of any suitable materials.

Apparatus for Providing Variable Flow Restriction

Figure 33:
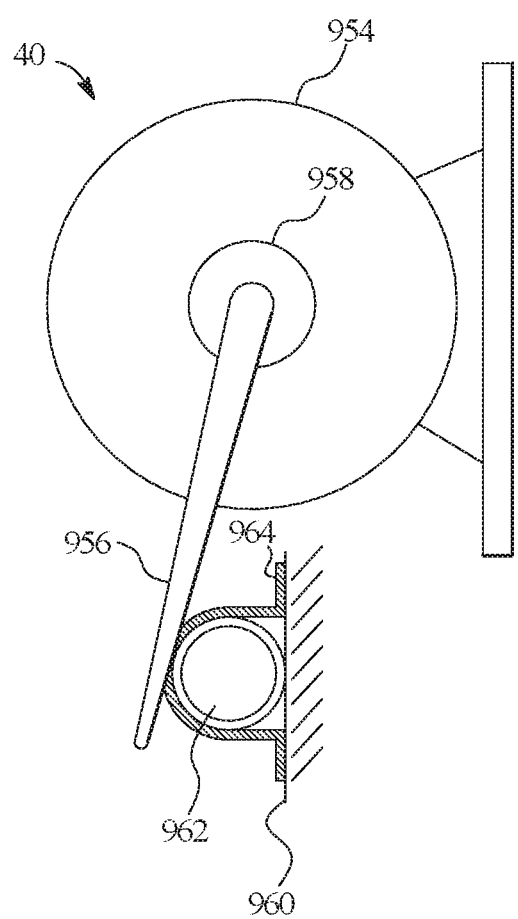
FIG. 33 is a schematic view of one embodiment for the variable flow restriction located between the dual dialyzers of the present invention.

Referring now to FIG. 33, one embodiment for variable flow restriction 40 is illustrated. While it is contended that there are likely many different ways to provide a repeatable and accurate variable flow restriction, variable restriction 40 of FIG. 33 provides one suitable configuration. System 40 includes a stepper motor 954, which is coupled to a lever arm 956 via a coupler 958. Stepper motors are known in the art as highly accurate and repeatable positioning devices that can receive signals from a microprocessor that commands stepper motor 954 to turn a precise distance, and perhaps at a desired acceleration and velocity. In FIG. 33, stepper motor 954 is used primarily to position lever arm 956 to a precise position with respect to a fixed surface 960.

A tube section 962 shown also in FIGS. 1, 4, 5, 9, 12 and 14, connects dialysate flow between dialyzers 20 and 30. FIG. 33 illustrates that section 962 is held in place against surface 960 via bracket 964. Lever arm 956 as seen in FIG. 33 is currently in a position that enables full flow through tube section 962. That is, in the configuration illustrated in FIG. 33, very little dialysate would backflow through the membranes of one of the dialyzers 20 or 30. As lever arm 956 is rotated in a counterclockwise direction as seen in FIG. 33, tube section 962 deforms and increasingly decreases in cross-sectional area, causing the amount of restriction in device 40 to continuously increase. Indeed, lever arm 956 could be rotated to a point that would virtually restrict all flow through tube section 962, forcing virtually all of the therapy fluid to enter the extracorporeal circuit 50 through the membranes of one of the dialyzers 20 or 30.

Importantly, stepper motor 954 is accurate and repeatable. That is, stepper motor 954 can be commanded to rotate lever arm 956 to virtually the same position time and time again. Because tube section 962 is held in the same position via bracket 964 relative to lever arm 956 and fixed surface 960, lever arm 956 accurately and repeatedly creates the same amount of restriction through line 962 when the arm 956 travels to the same commanded position. The programmable nature of stepper motor 954 also enables restriction 40 to have virtually any desired restriction profile that varies over the duration of therapy as desired by the patient, physician or other operator. Such variable restriction profiles are described above and can be stored as programs within a memory device of the controller of the systems described herein, such that one of the variable restriction profiles can be called upon and implemented as desired.

Interfacing Between Cassette, Blood Treatment Machine and Solution Bags

Figure 34:
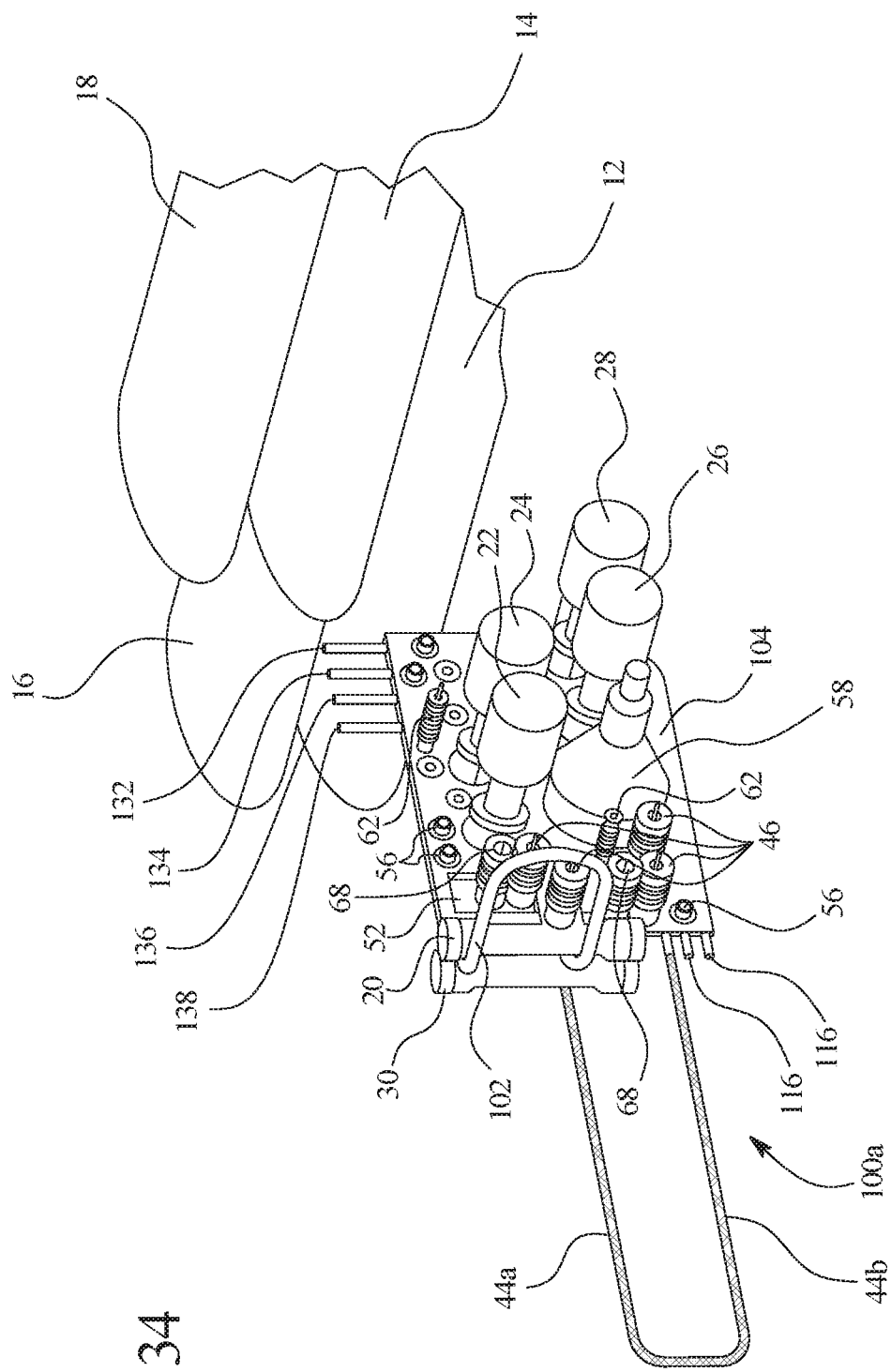
FIG. 34 is a perspective view showing the cassette operably configured with flow actuation components of the dialysis systems of the present invention.

Referring now to FIG. 34, cassette 100a (shown above in FIGS. 2 and 3) is shown in an operable position interfaced with a number of the flow devices that are located inside of the blood treatment machine. Cassette 100a as illustrated includes a housing 104. Attached to housing 104 are a number of flow components, which are provided either in part or completely on or in cassette 100a. As illustrated, dialyzers 20 and 30 are attached to housing 104. The tubing 102 extends so as to be able to loop around a pump head portion of blood peristaltic pump and connects fluidly to housing 104 of cassette 100a. The arterial and venous patient lines 44a and 44b respectively also are attached to or communicate with cassette 100a. As illustrated in FIG. 34, patient access lines 44a and 44b are initially connected together to preserve the sterilization of air within those lines. A number of sensors, such as pressure sensors 46 are further integrated with cassette 100a.

For reference, drain container 12 and solution bags 14 to 18 are shown in one possible proximal position to cassette 100a in FIG. 34. Bags 12 to 18 connect via tubes (not illustrated) to bag ports 132 to 138, respectively, extending from housing 104 of cassette 100a. Ports 132 to 138 are also shown in FIGS. 2 and 3. FIGS. 2 and 3 also show a number of additional ports. For example, ports 106 connect to dialyzers 20 and 30. Ports 108 connected to peristaltic pump 102 shown in FIGS. 2 and 12. FIGS. 2, 3 and 12 also show a number of additional ports 116, which are connected to filters 20, 30 as noted in connection with FIGS. 2 and 3. Additional ports, such as ports 116, and valve portions 156 can be added to cassette 100a to operate and communicate with sorbent cartridge 222 of FIGS. 5 to 8.

FIG. 34 also illustrates a number of the devices that are housed inside the blood treatment machine. For example, FIG. 34 illustrates a number of valves 56, which are operably connected to cassette valve positions 156 shown in FIG. 2. The fluids at all time flow through the sterile cassette 100a, which is disposable. The mechanics and electronics of valves 56, on the other hand, are placed inside the machine and reused. In a similar manner, heater 58 couples operably to fluid heating portion 158 of cassette 100a shown in FIG. 2. FIG. 34 also shows drip chambers 52 (referring collectively to chambers 52a to 52c, e.g.) as well as temperature sensors 62 operable with cassette 100a. Further, infusion pump actuators of pumps 22 and 24, shown in FIG. 12, are coupled operably to pump chambers 122 and 124 as seen in FIG. 2. Likewise, ultrafiltrate pump actuators or pumps 26 and 28 are coupled operably to pump chambers 126 and 128 shown in FIG. 2.

Figure 35:
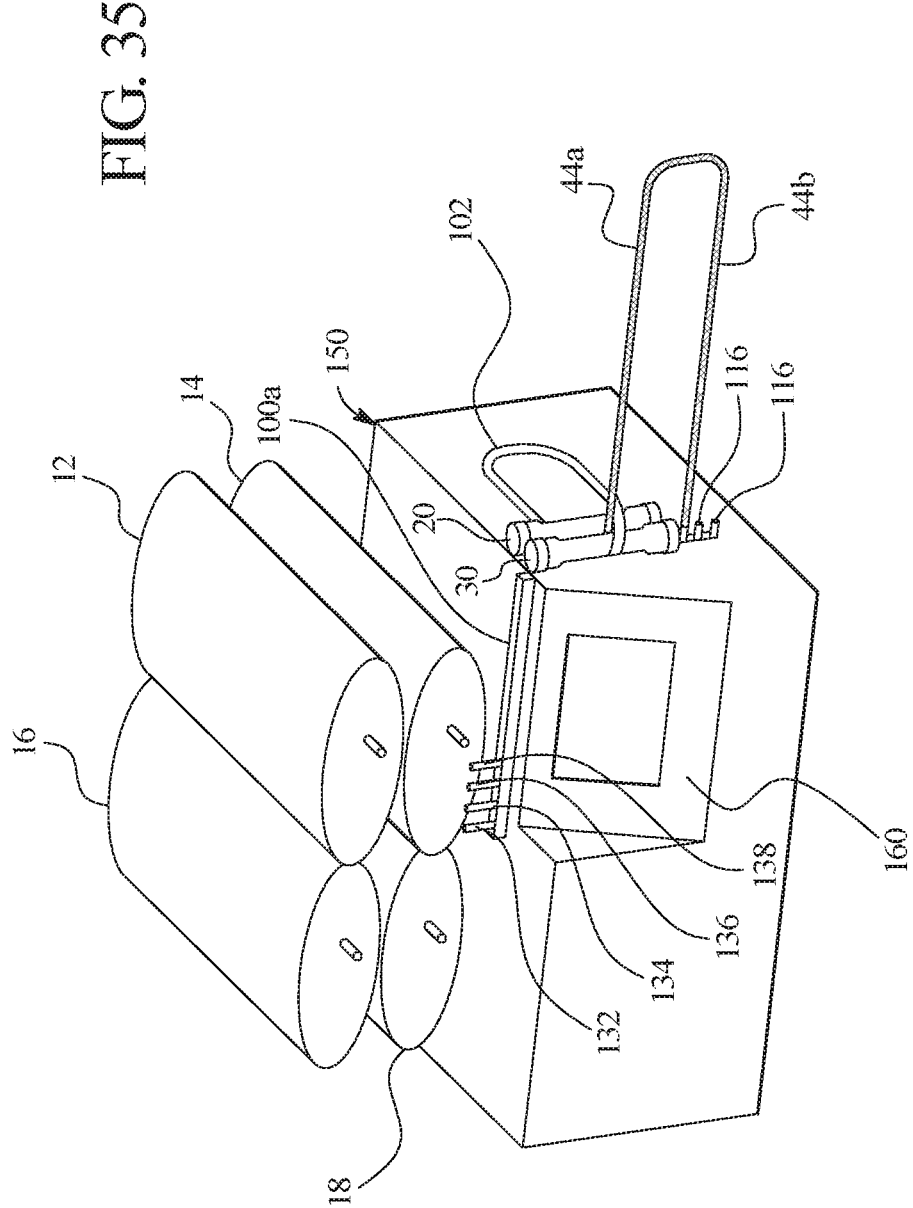
FIG. 35 is a perspective view of one embodiment for operably coupling the solution bags to the renal failure therapy machine of the present invention.

Referring now to FIG. 35, the flow devices of FIG. 34 are shown this time housed inside blood treatment machine 150. Blood treatment machine 150 is a machine that performs any of the systems and therapies described herein. FIG. 35 illustrates that in one embodiment, drain bag 12 and solution bags 14 to 18 are stored in operation in a two-by-two arrangement on top of machine 150. Machine 150 also shows the relative placement of cassette 100 within machine 150. In particular, bag ports 132 to 138 extend upwardly from the top of the machine in relatively close proximity to bags 12 to 18. Ports 116 (e.g., attaching to the dialyzers or hemofilters, the sorbent cartridge or attaching drip chambers 52, etc.) extend from the side of machine 150.

FIG. 35 also illustrates that peristaltic pump blood line 102 extends outside machine 150 and mates with the pumping head portion of the peristaltic pump 48, which is housed mainly inside machine 150, but which has a rotating head that is located outside machine 150 to receive tube 102. Cassette 100a slides almost entirely inside machine 150, leaving dialyzers 20 and 30, peristaltic line 102, patient access lines 44a and 44b and ports 116 outside of machine 150.

Machine 150 includes a graphical user interface 160 that enables the patient 42, nurse or other operator, to begin therapy, monitor therapy, receive status messages from the therapy, as well as collect data for post-therapy analysis of the patient's treatment and status. Graphical user interface ("GUI") 160 allows patient 42 or other operator to select the desired therapy and to adjust the desired or necessary fluid loss or UF volume for each treatment. GUI 160 receives prescription entries via the packetized or checked data packets via memory card, flash memory, modem, internet connection, or other suitable local area or wide area mode of data communication. The electronic and software architecture running GUI 160 is redundant in one preferred embodiment, so that monitoring and controlling any critical function is executed through separate hardware and software.

GUI 160 in one embodiment includes a touch screen that enables the patient 42 or operator to enter desired parameters. In an alternative embodiment, GUI 160 uses electromechanical devices, membrane switches, voice activation, memory cards, or any combination of the above-described input devices. In one embodiment, GUI 160 is run via multiple processors, such as a supervisory/delegate processor system. A separate processor is provided for monitoring and checking that the critical functions of the machine are being performed correctly. That is, while one processor is dedicated to controlling the flow devices of the system to achieve the desired therapy, another processor is provided to check that the hardware processor and the associated flow devices are operating properly.

Figure 36:
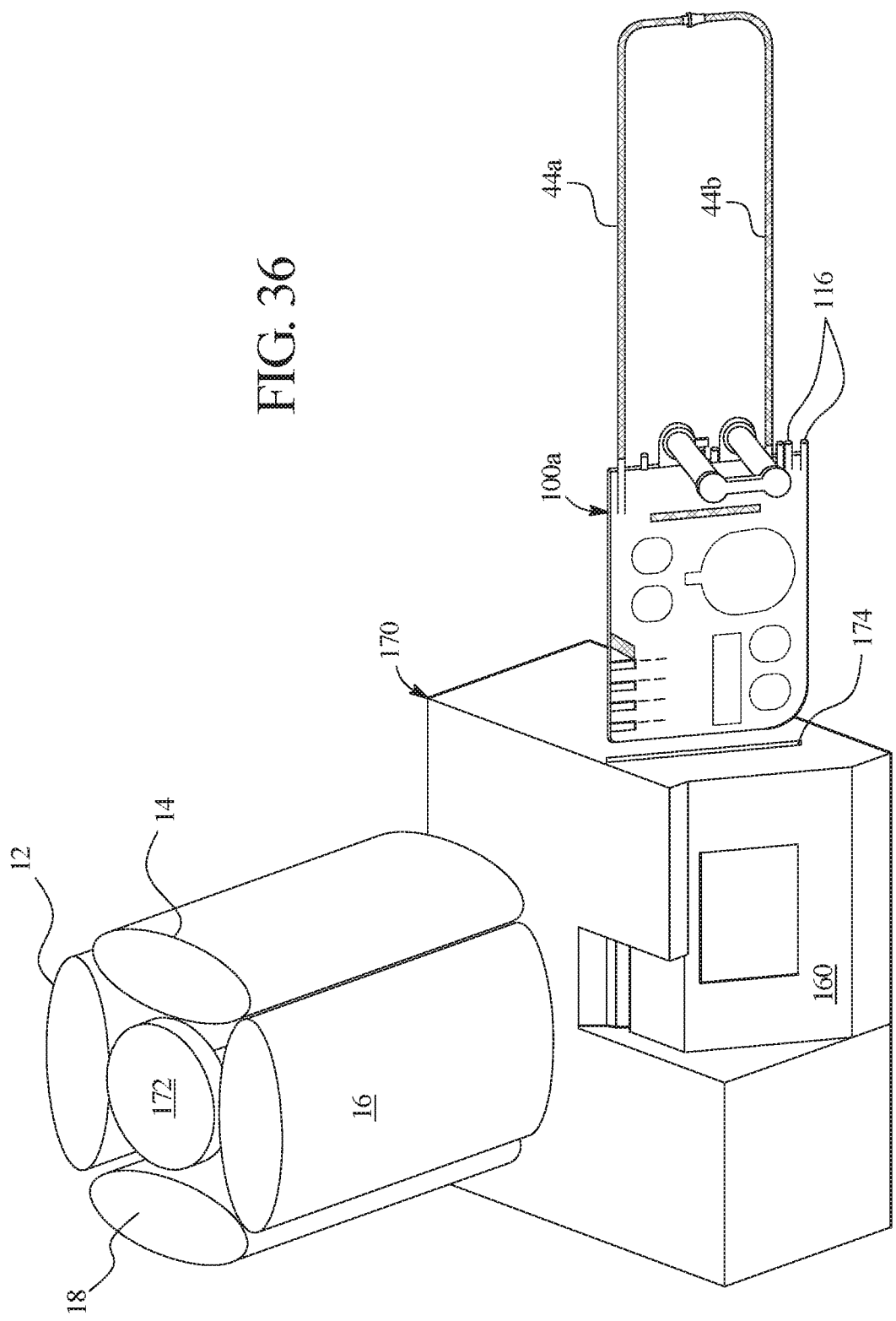
FIGS. 36 and 37 are perspective views of embodiments for coupling the solution bags to the renal failure therapy machine, which also show one embodiment for enabling the machine to receive the cassette of the present invention.
Figure 37:
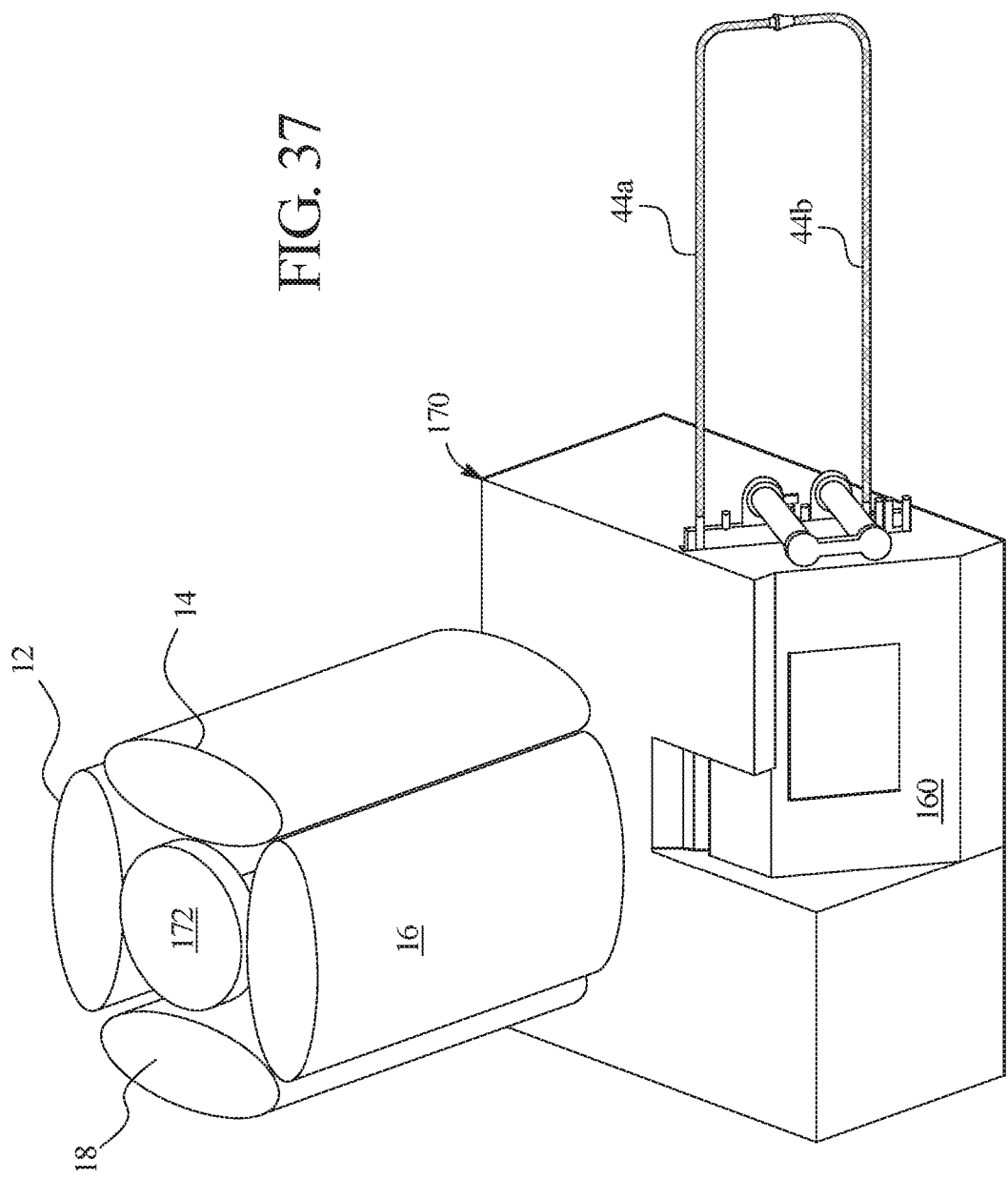

FIGS. 36 and 37 illustrate an alternative blood treatment machine 170, which differs from machine 150 primarily in the arrangement of drawing bag 12 and solution bags 14 to 18. In particular, machine 170 uses a carousel-type arrangement 172 that enables containers 12 to 18 to hang vertically.

FIG. 36 illustrates cassette 100a removed from machine 170. Machine 170 defines slot 174 shown in FIG. 36, which enables cassette 100a to be inserted into machine 170, as illustrated by FIG. 37. As illustrated, machine 170 employs GUI 160 described above in connection with FIG. 35. FIGS. 35 to 37 illustrate that it is possible to configure the support of solution bags 12 to 18 in multiple ways.

Referring now to FIGS. 38 to 41, an alternative blood treatment machine 180 employs linear tubing pumps to move one or both the dialysate and blood instead of the pumps described above for such fluid transport. Indeed, it is possible to use any one of a multitude of different types of pumping technologies for either the dialysate flow path or the patient's blood circuit. For example, as shown in FIG. 34, peristaltic pumps, such as pump 48, used earlier for the blood circuit can be used instead of the volumetric pumps 22 to 28 described above for the dialysate flow path. The peristaltic pumps, like pump 48, are located mainly in the blood therapy machine and receive tubes outside the machine, similar to tube 102, but which pump dialysate or therapy fluid.

Figure 38:
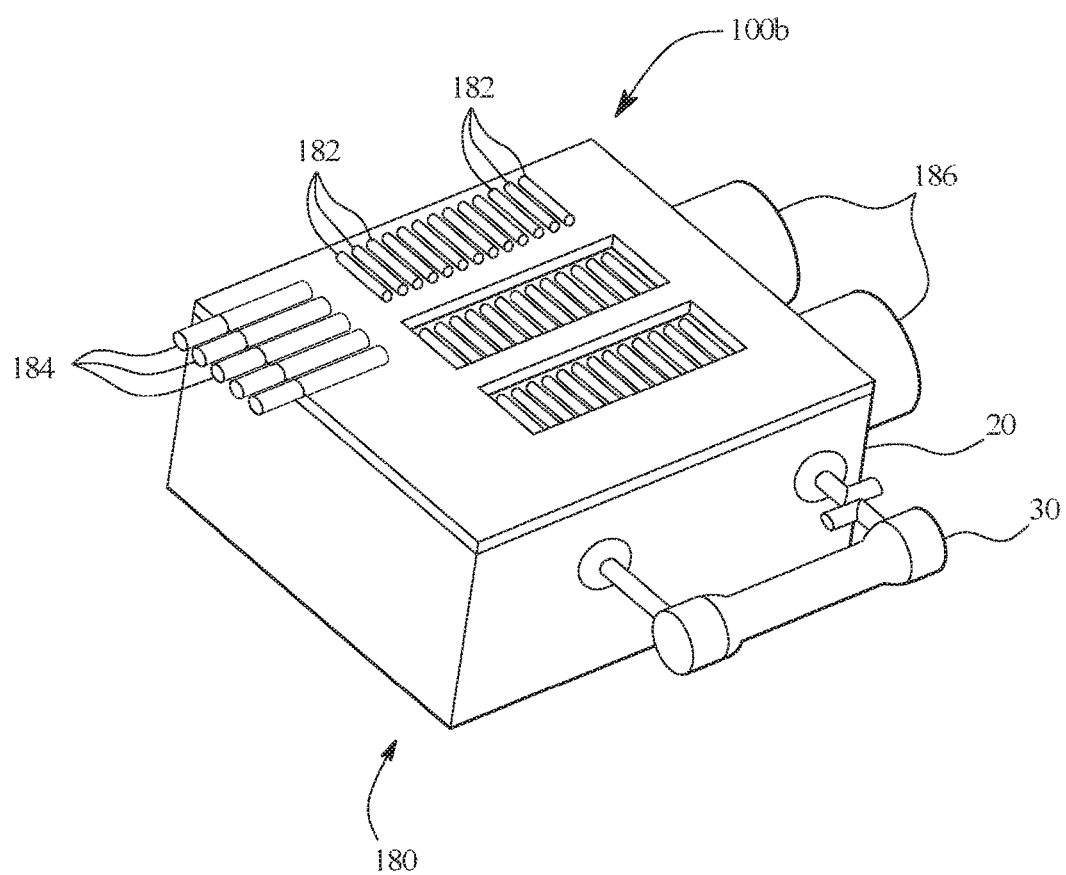
FIG. 38 is a perspective view of an alternative embodiment for pumping therapy fluid employing linear tubing pumps.

Machine 180 of FIG. 38 illustrates a similar type of alternative, which uses a series of adjacently placed round driver fingers 182 that run generally perpendicular to dialysate or therapy flow tubes, which are located within alternative cassette 190. Linear fingers 182 compress dialysate tubes 184 sequentially in a manner similar to the rollers in a peristaltic pump to compress and move fluid within flexible dialysate tubes 184 of cassette 100b through such tubes and to the desired destination for the fluid. High flux dialyzers 20 and 30 connect to alternative cassette 100b as described above and in one embodiment extend from one side of machine 180 as illustrated. One or more motors 186 are provided to rotate cams that drive linear fingers 182 according to the prescribed sequence.

Figure 39:
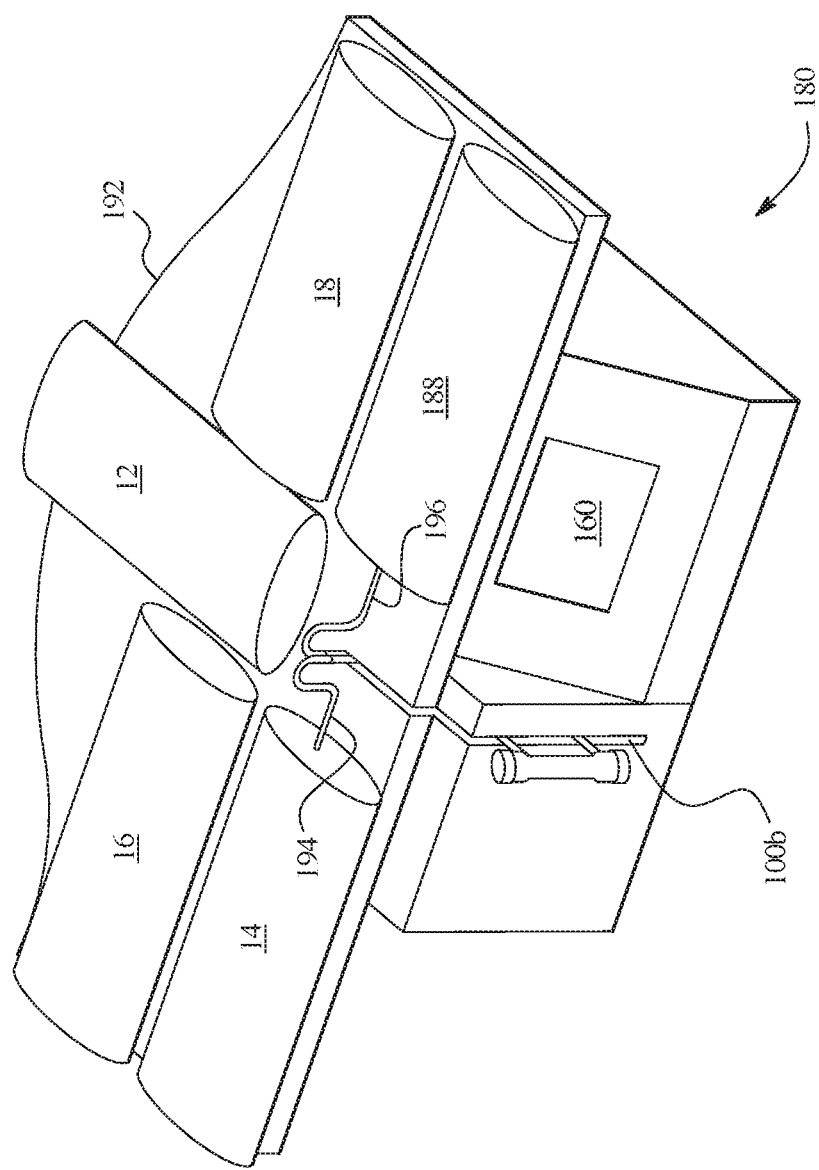
FIG. 39 is a perspective view of one embodiment for operably coupling the solution bags to a system using linear tubing pumps.

Referring now to FIG. 39, one embodiment of the linear tubing system is illustrated. Here, drain bag 12 and a plurality of solution bags 14, 16, 18 and 188 are supported by a tabletop 192. Tubing connections, such as via tubes 194 and 196, are made between the alternative cassette 100b and the bags 12 to 18 and 188. Cassette 100b is positioned into a slot 198 defined by machine 180. Machine 180 also includes GUI 160 described above.

Figure 40:
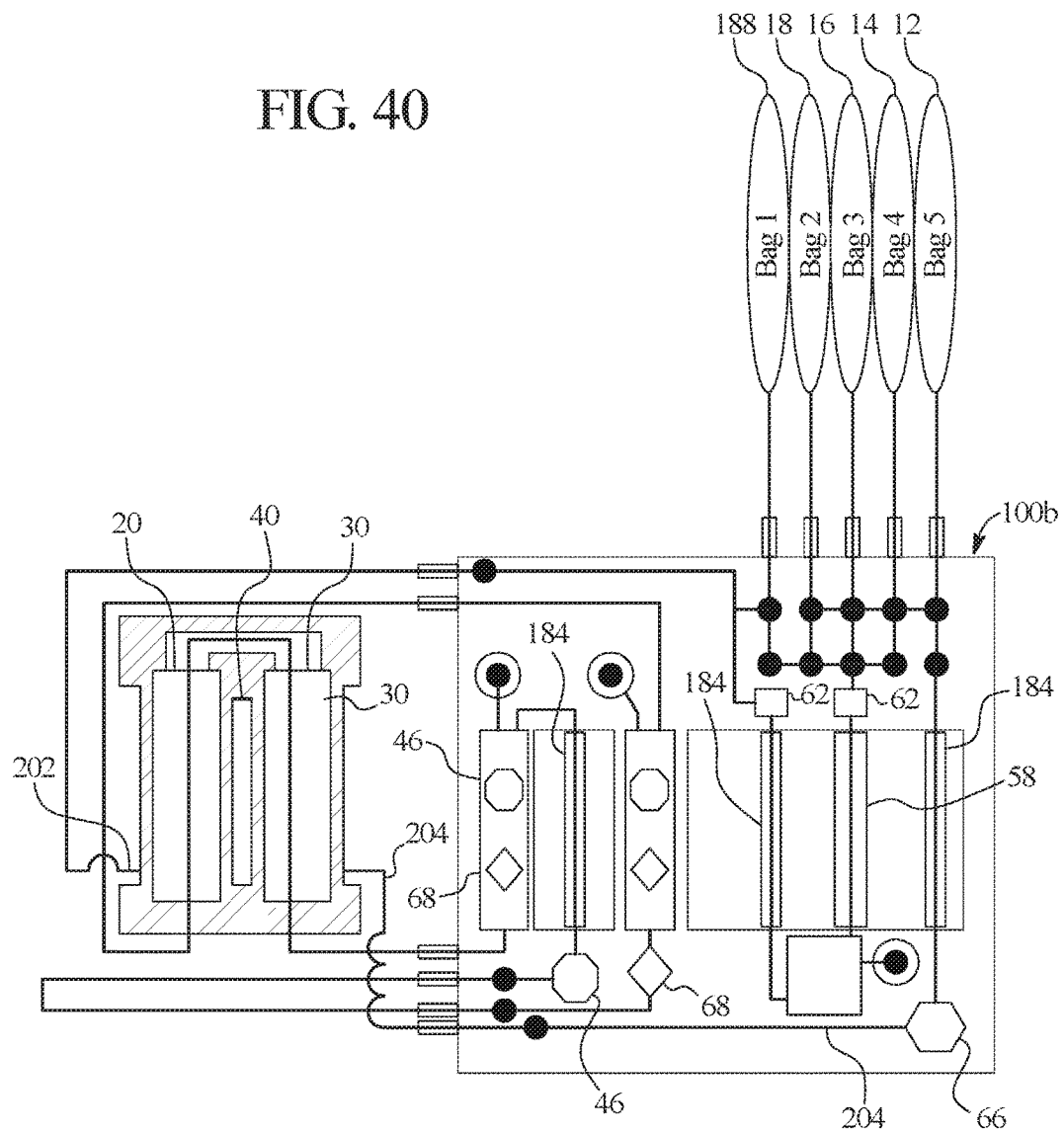
FIG. 40 is a schematic diagram showing one embodiment of a cassette of the present invention, which operates linear tubing pumps of the present invention.
Figure 41:
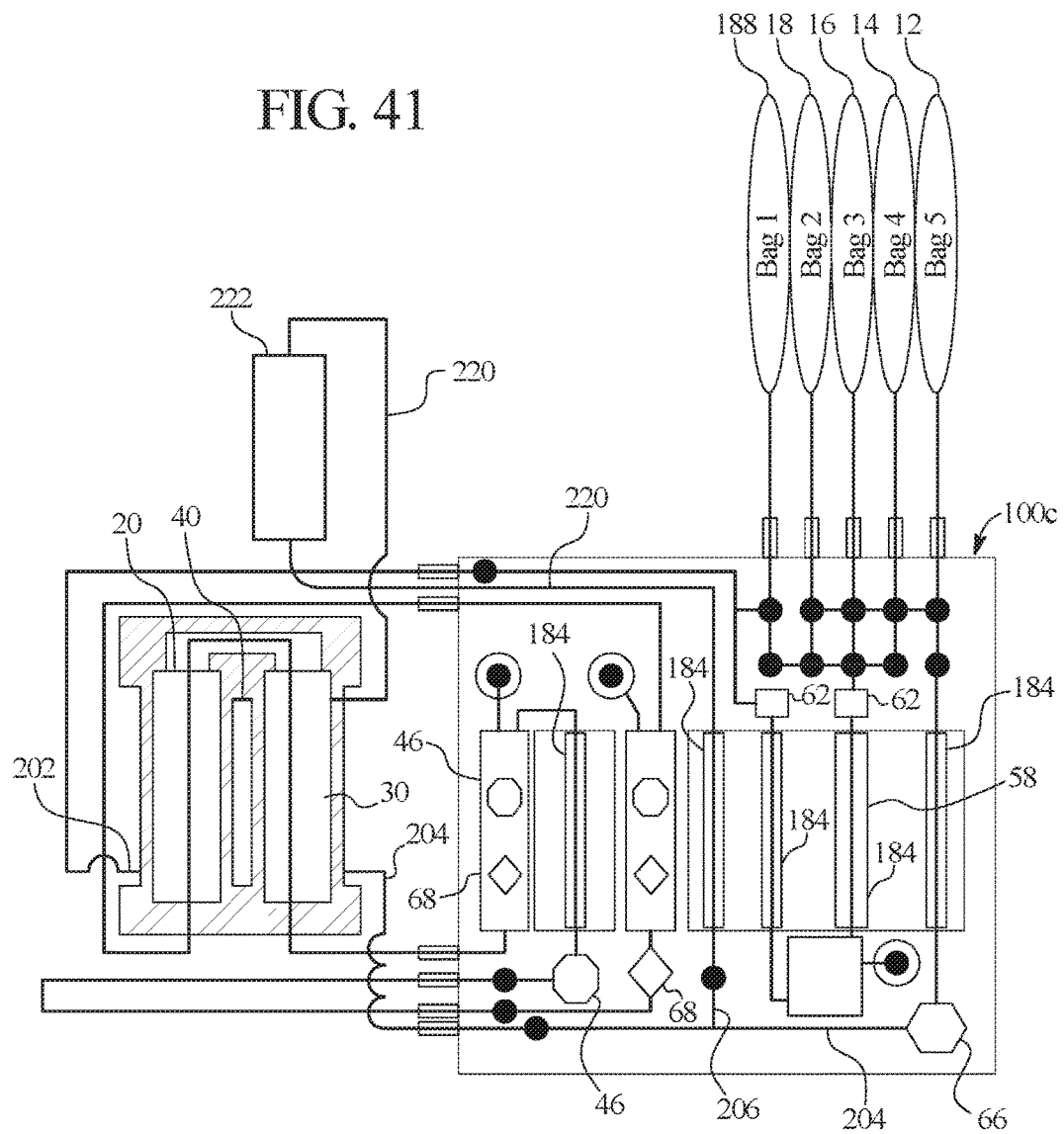
FIG. 41 is a schematic illustration of another embodiment of a cassette of the present invention, which operates with linear tubing pumps.

Referring now to FIGS. 40 and 41, cassette 100b and an alternative cassette 100c illustrate schematically and respectively various embodiments for configuring the cassettes of the present invention to operate with linear tubing pumps. Cassettes 100b and 100c both operate with drain bag 12 and solution bags 14 to 18 and 188. Both cassettes 100b and 100c include a number of sensors, such as blood leak detector 66, a plurality of pressure sensors 46 and a plurality of air/water level sensors 68. Both cassettes 100b and 100c operate with externally mounted high flux dialyzers 20 and 30 as discussed above. A restriction 40 is placed in the dialysate path between the arterial and venous dialyzers.

Cassettes 100b and 100c both include linear tubing portions 184 shown above in FIG. 38. FIGS. 40 and 41 illustrate one advantage of the linear tubing pumps of the present invention, namely, that the driver fingers 182 associated with machine 180 are operable with linear tubing portions 184 of cassette 100b/100c for both the blood and dialysate flow paths, eliminating the need for having two types of pumping systems.

Cassette 100c of FIG. 41 includes an additional linear tubing portion 184 that is connected fluidly with recirculation line 220, which leads to an activated charcoal or sorbent cartridge 222. Recirculation line 220 also extends from cartridge 222 into the dialysate input and of high flux dialyzer 30. The flow of dialysate to venous dialyzer 20 and from arterial dialyzer 30 is monitored in connection with the linear tubing pumps in one embodiment via a flow measuring device that measures flow at the input line 202 into venous dialyzer 20, which senses how much fresh dialysate is supplied from bags 14, 16, 18 and 188. A flow measuring device also measures the flow leaving arterial dialyzer 30 via line 204 that leads via the leak detector 166 to drain bag 12. FIG. 41 shows a branch line 206 which selectively allows a portion of the spent dialysate or UF to be shunted via recirculation line 220 to charcoal or sorbent cartridge 222 and then back into arterial dialyzer 30.

Inductive Heater

Figure 42:
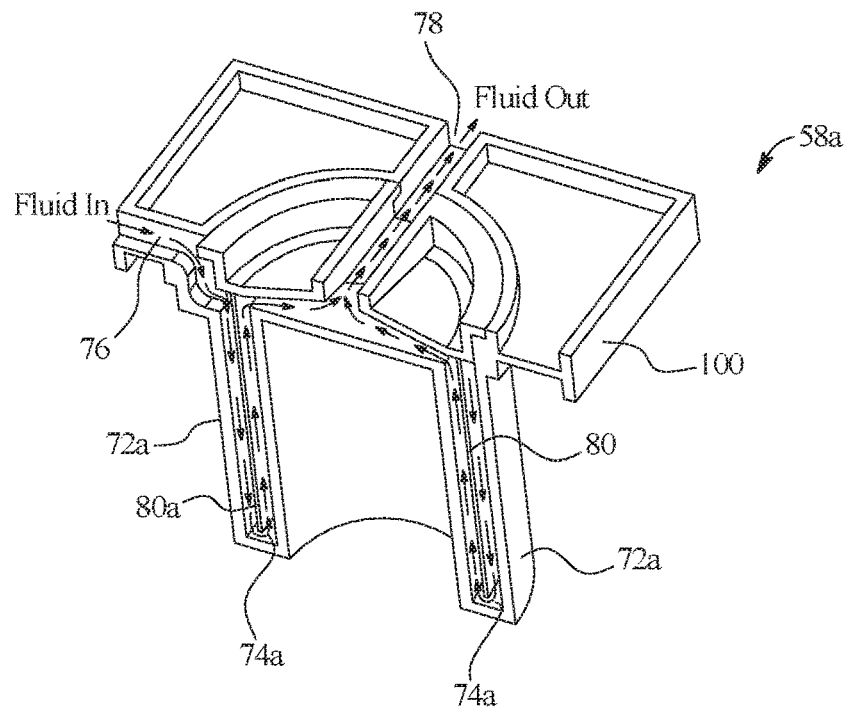
FIGS. 42 and 43 are sectioned perspective views of different alternative implementations of one embodiment of a fluid heater of the present invention.
Figure 43:
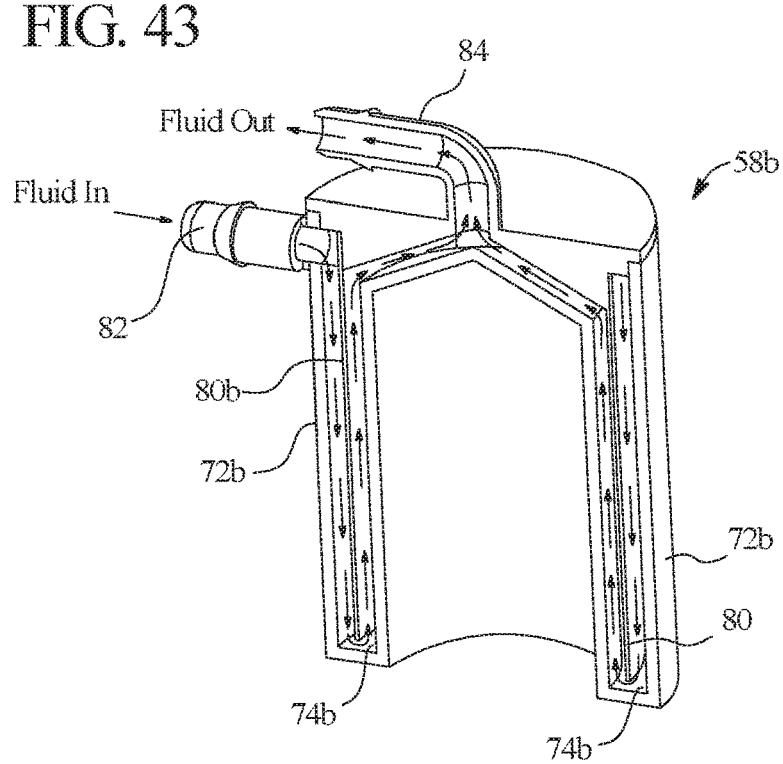

Referring now to FIGS. 42 and 43, two embodiments for the heater 58 of the present invention are illustrated by heaters 58a and 58b, respectively. As discussed, heater 58 may be any suitable type of medical fluid heater such as a plate heater, infrared or other type of radiant heater, convective heater, or any combination thereof. Heater 58a, is an inductive heater or heater with an inductive coil. Inductive heater 58a is configured integrally or connected fixedly to a disposable cassette, such as cassette 100. Inductive heater

58b, on the other hand, connects to the disposable cassette 100 via a pair of tubes and is located apart from the main body of cassette 100.

As seen in FIG. 42, a portion of cassette 100 is shown. Cassette 100 defines fluid flow path 76 and fluid flow path 78. In the illustrated embodiment, fluid flow path 76 is the inlet to inductive heater 58a. Fluid flow path 78 is the outlet of fluid heater 58a. That is, a fresh dialysate pump can pump fluid to flow path 76 and into a fluid chamber 74a defined by heater housing 72a. The heated fluid then flows from fluid chamber 74a through flow channel 78 for example to a dialyzer or volumetric balancing device.

Regarding inline heater 58b, fluid flows via a dialysate pump through a tube (not illustrated) connected sealingly to inlet port 82. Fluid flows out of heater 58b to the disposable cassette through a tube (not illustrated) connected sealingly to outlet port 84 and a similar port located on the main body of the disposable cassette.

Heaters 58a and 58b each include a heating element or inductive coil 80. Heater element 80 is inserted into each of the fluid flow channels 74a and 74b. In an embodiment, heater element 80 is substantially cylindrical and when placed within the substantially cylindrical housings 72a and 72b, respectively, creates an annular fluid flow path that flows longitudinally down the outside of heater element 80 and up the inside of heater element 80 before leaving heater 58a or 58b. Heater elements 80 can be corrugated or otherwise have fin-like structures to increase the surface area of the heating element with respect to the fluid flowing through heaters 58a and 58b.

In an embodiment, heater element 80 is a or acts as a shorted secondary coil of a transformer. The closed or looped element does not allow energy to dissipate electrically, instead is converted to heat. A transformer located in the machine includes a primary coil. The primary coil can be powered by an AC high frequency supplier.

The fluid heaters 58a and 58b incorporate one or more temperature sensors located so that the temperature of the liquid flowing through the heater can be monitored. The temperature sensors in one embodiment are infrared temperature sensors. Heater element 80 in an embodiment is made of a non-corrosive metal, such as stainless steel.

In operation, cold or room temperature dialysate is pumped into the induction heaters 58a or 58b along the outside of heater element 80, around the bottom of heater element 80 and then along the inside of heater element 80, finally exiting the heater. In an embodiment, the disposable cassette, such as cassette 100 is inserted such that the heating cavity defined by housing 72a is as positioned directly on the primary coil located within the renal therapy machine. When energized, the primary coil magnetically induces a current into the shorted coil 80, causing the element 80 and surrounding fluid to heat. The primary coil serves a secondary purpose of centering and steadying the cassette within the renal failure therapy machine.

In one implementation, the surface area of the element 80 may be around or less than ten square inches to heat dialysate from five degrees Celsius to thirty-seven degrees Celsius at a flow rate of approximate 150 milliliters per minute. The heater may have a dimension of about 1 inch (25.4 mm) in diameter by 1.5 inches (38.1 mm). Other sizes, shapes and/or multiple coils 80 may be used alternatively.

Cassette with Balance Chambers

Figure 44:
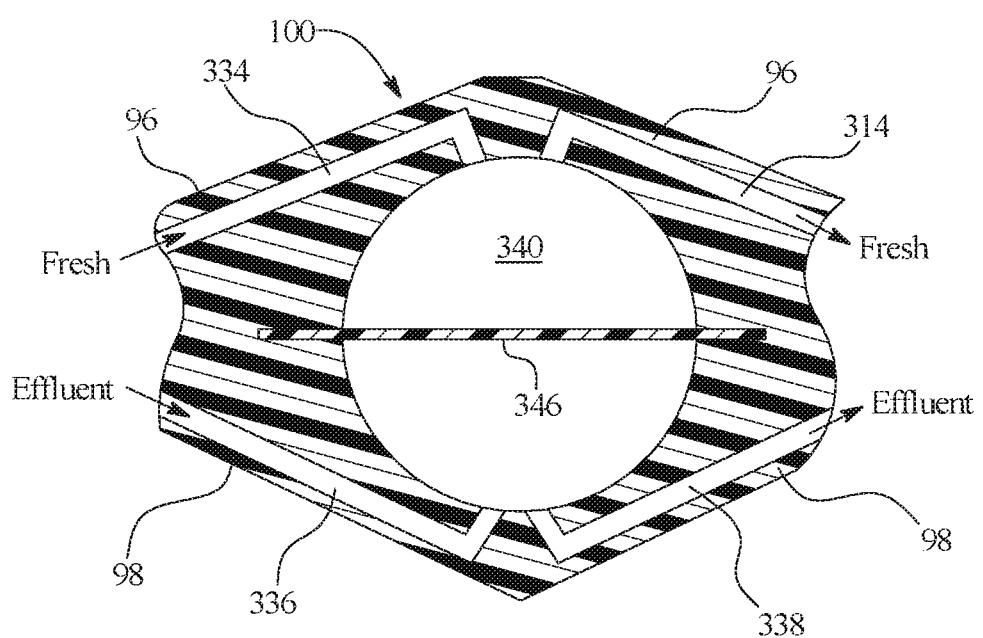
FIG. 44 is a cutaway section view illustrating one embodiment for incorporating a balance chamber into a disposable cassette.

Referring now to FIG. 44, a portion of cassette 100 shown in cross-section illustrates one embodiment for providing a cassette-based balance chamber 340 of the present invention. Cassette 100 (including each of the cassettes 100a to 100c) includes an upper portion 96, a lower portion 98 and a flexible sheeting 346. In an embodiment, portions 96 and 98 are made of a suitable rigid plastic. In an embodiment, flexible membrane or diaphragm 346 is made of a suitable plastic or rubber material, such as PVC, non DEHP PVC, Krayton polypropylene mixture or similar materials.

The sheeting 346 is welded or bonded to one half 96 or 98. Excess sheeting is trimmed. The two portions 96 and 98 are then bonded at a mating interface between the portions. This captures the sheeting 346 between portions 96 and 98. Portions 96 and 98 are configured so that the welding of sheeting 346 is constrained between portions 96 and 98. Portions 96 and 98 thereby sandwich the flexible membrane or diaphragm 346 of the cassette.

Using the same nomenclature from FIGS. 17 to 21 for the inlet and outlet flow paths to balance chamber 340, upper portion 96, which receives and dispenses fresh dialysate, defines an inlet flow path 334 and an outlet fresh fluid flow path 314. Likewise, lower portion 98, which receives and dispenses effluent dialysate defines and inlet effluent path 336 and an outlet effluent 338. Those fluid paths are in fluid communication with the like numbered fluid lines shown in FIGS. 17 to 21.

When balance chamber 340 is full of fresh fluid, a valve located upstream of the balance chamber and fresh fluid path 334 is closed. To push dialysate to the patient or dialyzer, a valve communicating with inlet effluent line 336 is opened as is a valve communicating with fresh dialysate delivery line 314. That valve configuration enables pressurized effluent fluid to push membrane or diaphragm 346 away from the opening of effluent inlet 336 and towards the top of chamber 340, thereby dispelling fresh dialysate within chamber 340 to a dialyzer or patient.

Balance chamber 340 may be oriented horizontally as shown or vertically. If vertically, the inlets are preferably located below the outlets to better enable air to escape from the fluid. Also, the ports may be combined to a single port for each chamber, similar to the alternative valve configuration of FIG. 38 for the balance tube. The single ports may be located closer to or directly adjacent to the interface between portions 96 or 98 as desired.

In another embodiment (not illustrated) the portion of cassette 100 that provides a balance chamber does not include upper and lower rigid portions 96 and 98. Instead that portion of cassette 100 includes three-ply or three separate flexible membranes. When the cassette is loaded into the renal failure therapy machine, the machine pulls a vacuum on the two outer membranes, causing the outer membranes to be sucked against the machine walls defining the balance chamber. This configuration reduces the amount of rigid plastic needed and is believed to be simpler and cheaper to produce. In an alternative configuration, the pressures in the balance chamber cavities push the sheeting to conform to the cavities, negating the need for a vacuum. The outer plies may have ports formed integrally with or connected sealingly to the plies to mate with inlet and outlet dialysate lines.

Balance Tube

Figure 45:
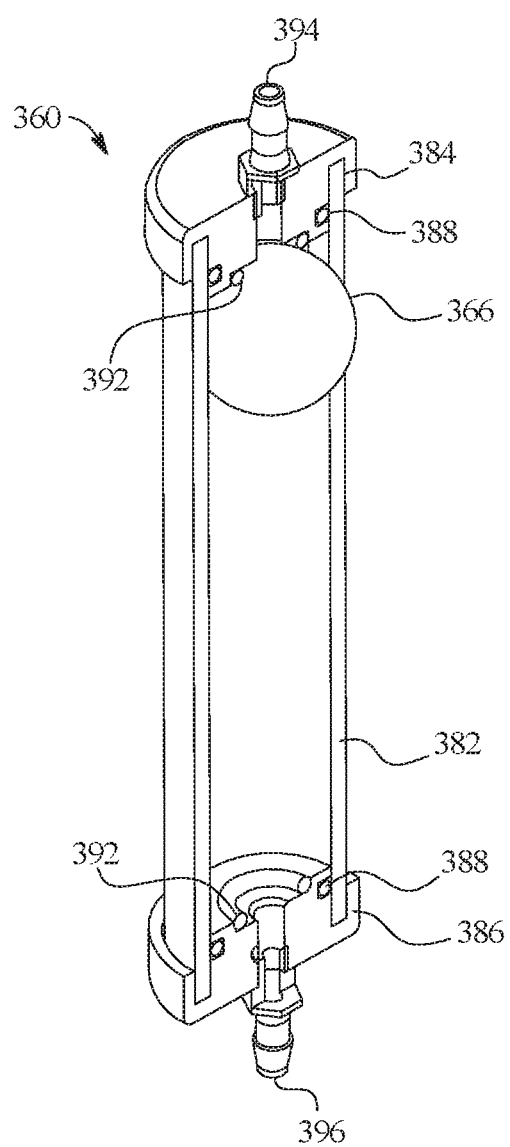
FIG. 45 is a perspective cutaway view of one embodiment of the balance tube of the present invention.

Referring now to FIG. 45, one embodiment of the balance tube 360 is illustrated. As discussed above and using like nomenclature, balance tube 360 includes a separator 366, which functions similar to the flexible membrane 346 of balance chamber 340. In the illustrated embodiment, separator 366 is a ball or spherical object that moves snuggly within a cylindrical housing 382. A pair of caps 384 and 386 are provided on either end of cylindrical housing 382. Caps 384 and 386 seal to cylindrical tubing 382 via outer O-rings 388. Separator or ball 366 seals to caps 384 and 386 via inner O-rings 392. In an alternative embodiment, caps 384 and 386 are permanently or hermetically sealed to cylindrical tube 382. Ports 394 and 396 are formed integrally with or are attached to caps 384 and 386, respectively. Ports 394 and 396 seal to mating tubes via any mechanism known to those with skill in the art.

In an embodiment, cylindrical tube 382 is translucent or transparent, so that an optical sensor can detect if ball or separator 366 has properly reached the end of travel. Ultrasonic or other types of sensors may be used alternatively. The assembly could be made of two pieces of injection molded plastic that mate in the center of the tubes with the separator 366 installed prior to mating. Mating may be done by solvent bond, ultrasound or other techniques known to one of skill in the art. Tube 382 may also be a simple extrusion with molded end caps applied by a secondary operation.

Ball or separator 366 is sized to fit snuggly but smoothly within the interior of cylinder 382. A small amount of mixing between fresh and effluent fluid may occur without substantially affecting the performance of the system. In an alternative embodiment, a cylindrical piston type separator is provided. In either case, separator 366 may have additional sealing apparatus, such as wipers or deformable flanges that help to enhance the sliding or rolling seal as the case may be.

Each of the components shown in FIG. 45 for balance tube 360 may be made of plastic or other suitable material. In an embodiment, balance tube 360 is a disposable item, which may be formed integrally with cassette 100 or attached to the cassette via tubing, similar to heaters 58a and 58b of FIGS. 42 and 43. It is important to note that the O-rings and fittings are not be necessary if injection molded caps or assemblies are used. In addition, sensors such as ultrasonic or optical sensors, for the positioning of the separator can eliminate a need for sealing at the end of the tube.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention is claimed as follows:

1. A method for priming a hemodialysis treatment comprising:
   providing a disposable cassette including at least a portion of a dialysate circuit and at least a portion of a blood circuit;
   placing a dialyzer in fluid communication with the dialysate circuit via a to-dialyzer dialysate line and a from-dialyzer dialysate line;
   placing the dialyzer in fluid communication with the blood circuit via an arterial blood line and a venous blood line;
   placing a source of dialysis fluid in fluid communication with the dialyzer;
   priming the dialysate circuit with dialysis fluid from the source while both the to-dialyzer dialysate line and the from-dialyzer dialysate line are connected at their dialyzer ends to the dialyzer; and
   priming the blood circuit with dialysis fluid from the source by actuating at least one valve provided by the disposable cassette.

2. The method of claim 1, wherein priming the blood circuit includes reversing a blood pump at least one time.

3. The method of claim 2, which includes reversing the blood pump after a drip chamber is filled with fluid.

4. The method of claim 1, wherein priming the blood circuit includes connecting patient ends of the arterial blood line and the venous blood line together.

5. The method of claim 1, which includes actuating at least one valve in the blood circuit to prime the blood circuit.

6. The method of claim 1, wherein priming the blood circuit includes directing the dialysis fluid at one time in a first direction away from the dialyzer and at another time in a second direction towards the dialyzer.

7. The method of claim 1, wherein priming the blood circuit includes directing the dialysis fluid at one time in a treatment operation direction and at another time in a reverse of the treatment operation direction.

8. The method of claim 1, wherein priming the blood circuit includes pumping the dialysis fluid through the dialyzer.

9. A dialysis machine configured and arranged to perform the method of claim 1.

10. A method for priming a hemodialysis treatment comprising:
    providing a sorbent cartridge for cleaning used dialysis fluid returning from a dialyzer;
    preparing a batch of dialysis fluid in a quantity commensurate with being recycled through the sorbent cartridge multiple times;
    priming a dialysate circuit in fluid communication with the dialyzer using the batch of dialysis fluid, while both a to-dialyzer dialysate line and a from-dialyzer dialysate line are connected at their dialyzer ends to the dialyzer; and
    priming a blood circuit in fluid communication with the dialyzer using the batch of dialysis fluid.

11. The method of claim 10, wherein preparing the batch of dialysis fluid includes mixing water and concentrate.

12. The method of claim 10, wherein priming the blood circuit includes pumping dialysis fluid from the batch of dialysis fluid through the dialyzer.

13. The method of claim 10, wherein priming the blood circuit includes connecting patient ends of an arterial blood line connected to the blood circuit and a venous blood line connected to the blood circuit together.

14. A dialysis machine configured and arranged to perform the method of claim 10.

15. A dialysis system comprising:
    a dialyzer;
    a disposable cassette including at least a portion of a dialysate circuit and at least a portion of a blood circuit, the dialysate circuit in fluid communication with the dialyzer via a to-dialyzer dialysate line and a from-dialyzer dialysate line, the blood circuit in fluid communication with the dialyzer via an arterial blood line and a venous blood line;
    a source of dialysis fluid in fluid communication with the dialyzer;
    at least one dialysis fluid pump configured to pump dialysis fluid from the source of dialysis fluid through the dialysate circuit;

at least one blood pump configured to pump blood from a patient through the blood circuit; and at least one processor configured to operate a sequence in which (i) the dialysate circuit is primed with dialysis fluid from the source of dialysis fluid while both the to-dialyzer dialysate line and the from-dialyzer dialysate line are connected at their dialyzer ends to the dialyzer; and (ii) the blood circuit is primed with dialysis fluid from the source of dialysis fluid by actuating at least one valve provided by the disposable cassette.

16. The dialysis system of claim 15, wherein the source of dialysis fluid includes regenerated dialysis fluid from a sorbent cartridge.

17. The dialysis system of claim 15, wherein the at least one processor reverses the at least one blood pump at least one time to prime the blood circuit.

18. The dialysis system of claim 15, wherein the at least one valve is located in the portion of the blood circuit included in the disposable cassette.

19. The dialysis system of claim 15, wherein the at least one valve is in fluid communication with the arterial blood line.

20. The dialysis system of claim 15, wherein the at least one processor is configured to prime the blood circuit with patient ends of the arterial blood line and the venous blood line connected together.

* * * * *